(12) United States Patent
Winther et al.

(10) Patent No.: US 9,340,824 B2
(45) Date of Patent: May 17, 2016

(54) IMMUNOHISTOCHEMISTRY DETECTION METHOD

(71) Applicant: Dako Denmark A/S, Minneapolis, MN (US)

(72) Inventors: Lars Winther, Smørum (DK); Jesper Lohse, Københaven (DK); Susanne Gabs, Stenlille (DK); Kenneth Heesche Petersen, Smørum (DK)

(73) Assignee: DAKO Denmark A/S, Glostrup (DK)

( * ) Notice: Subject to any disclaimer, the term of this patent is extended or adjusted under 35 U.S.C. 154(b) by 208 days.

(21) Appl. No.: 14/251,934

(22) Filed: Apr. 14, 2014

(65) Prior Publication Data

US 2014/0315204 A1 Oct. 23, 2014

Related U.S. Application Data

(62) Division of application No. 11/993,528, filed as application No. PCT/IB2006/003130 on Jun. 30, 2006, now Pat. No. 8,741,566.

(60) Provisional application No. 60/695,408, filed on Jul. 1, 2005, provisional application No. 60/695,409, filed on Jul. 1, 2005, provisional application No. 60/695,410, filed on Jul. 1, 2005.

(51) Int. Cl.
*C07H 21/04* (2006.01)
*C12Q 1/68* (2006.01)
(Continued)

(52) U.S. Cl.
CPC .......... *C12Q 1/6804* (2013.01); *A61K 47/4823* (2013.01); *A61K 47/48538* (2013.01);
(Continued)

(58) Field of Classification Search
CPC ............... C12Q 1/6804; C12Q 1/6876; A61K 47/4823; A61K 47/48538; A61K 47/48715; A61K 49/0041; A61K 49/0043; A61K 49/0056; C07H 19/06; C07H 19/10; C07H 19/16; C07H 19/20; C07H 21/00; C08G 69/02; C07C 231/02; C07C 233/36; G01N 33/5306
USPC .................... 536/24; 435/6.1, 6.11
See application file for complete search history.

(56) References Cited

U.S. PATENT DOCUMENTS 5,594,118 A 1/1997 Urdea et al.
5,648,506 A 7/1997 Desai et al.
(Continued)

FOREIGN PATENT DOCUMENTS

WO WO00/68434 11/2000
WO WO02/068695 9/2002
(Continued)

OTHER PUBLICATIONS

Hansen. Nucleoside and Nucleotides, 18(1), 5-9 (1999).
(Continued)

*Primary Examiner* — Robert T Crow
*Assistant Examiner* — Joseph G Dauner

(57) ABSTRACT

The invention provides compositions and methods for the detection of targets in a sample; in particular, an immunohistochemistry (IHC) sample. Probes and detectable labels may be provided in multiple layers in order to increase the flexibility of a detection system, and to allow for amplification to enhance the signal from a target. The layers may be created by incorporating probes and detectable labels into larger molecular units that interact through nucleic acids base-pairing, including peptide-nucleic acid (PNA) base-pairing. Optional non-natural bases allow for degenerate base pairing schemes. The compositions and methods are compatible with immunohistochemistry (IHC), but also could be used in immunocytochemistry (ICC), in situ hybridization (ISH), flow cytometry, enzyme immuno-assays (EIA), enzyme linked immuno-assays (ELISA), blotting methods (e.g. Western, Southern, and Northern), labeling inside electrophoresis systems or on surfaces or arrays, and precipitation, among other general detection assay formats. The invention is also compatible with many different types of targets, probes, and detectable labels.

26 Claims, 24 Drawing Sheets

Target 1 (antigen)   Target 2 (antigen)   Target 3 (nucleic acid sequence)

(51) Int. Cl.
| | |
|---|---|
| A61K 47/48 | (2006.01) |
| A61K 49/00 | (2006.01) |
| C07H 19/06 | (2006.01) |
| C07H 19/10 | (2006.01) |
| C07H 19/16 | (2006.01) |
| C07H 19/20 | (2006.01) |
| C07H 21/00 | (2006.01) |
| C08G 69/02 | (2006.01) |
| C07C 231/02 | (2006.01) |
| C07C 233/36 | (2006.01) |
| G01N 33/53 | (2006.01) |

(52) U.S. Cl.
 CPC ....... *A61K47/48715* (2013.01); *A61K 49/0041* (2013.01); *A61K 49/0043* (2013.01); *A61K 49/0056* (2013.01); *C07C 231/02* (2013.01); *C07C 233/36* (2013.01); *C07H 19/06* (2013.01); *C07H 19/10* (2013.01); *C07H 19/16* (2013.01); *C07H 19/20* (2013.01); *C07H 21/00* (2013.01); *C08G 69/02* (2013.01); *C12Q 1/6876* (2013.01); *G01N 33/5306* (2013.01)

(56) References Cited

U.S. PATENT DOCUMENTS

| | | | |
|---|---|---|---|
| 5,656,731 | A | 8/1997 | Urdea |
| 5,681,702 | A | 10/1997 | Collins et al. |
| 6,245,513 | B1 | 6/2001 | Lane et al. |
| 6,294,331 | B1 | 9/2001 | Ried et al. |
| 6,451,588 | B1 | 9/2002 | Egholm et al. |
| 6,737,236 | B1 | 5/2004 | Pieken et al. |
| 2002/0197630 | A1 | 12/2002 | Knapp et al. |
| 2004/0072202 | A1 | 4/2004 | McGall et al. |
| 2006/0014191 | A1 | 1/2006 | Lao et al. |

FOREIGN PATENT DOCUMENTS

| | | |
|---|---|---|
| WO | WO03/083440 | 10/2003 |
| WO | WO 03083440 A2 | 10/2003 |

OTHER PUBLICATIONS

Qian e tal., "Recent Developments in Signal Amplification Methods for In Situ Hybridization", Diagnostic Molecular Pathology, 2003, pp. 1-13, vol. 12, No. 1.
Collins et al., "A branched DNA signal amplification assay for quantification of nucleic acid targets below 100 molecules/ml", Nucleic Acids Research, 1994, pp. 2979-2984, vol. 25, No. 15.
Andras et al., "Strategies for Signal Amplification in Nucleic Acid Detection", Molecular Biology, 2001, pp. 29-44, vol. 19.
Campas et al., "DNA biochip arraying, detection and amplification strategies", Trends in Analytical Chemistry, 2004, pp. 49-62, vol. 23, No. 1.
Goodchild, "Conjugates of Oligonucleotides and Modified Olignucleotides: A Review of Their Synthesis and Properties", Bioconjugate Chemistry, May/Jun. 1990, pp. 165-187, vol. 1, No. 3.
Zalipsky, "Functionalized Poly(ethylene glycol) for Preparation of Biologically Relevant Conjugates", Bioconjugate Chem., 1995, pp. 150-165, vol. 6.
A.N. Player, "Single-copy Gene Detection Using Branched DNA (bDNA) In Situ Hybridization,"J. Histochemistry Cytochemistry 49(5): 603-611 (2001).
M. Yonezawa et al., "DNA Display of Biologically Active Proteins for In Vitro Protein Selection," J. Biochem. 135: 285-288 (2004).
Restriction Requirement mailed Dec. 6, 2011, for U.S. Appl. No. 11/993,571 (11 pages).
Office Action, mailed Feb. 7, 2012, for U.S. Appl. No. 11/993,571 (25 pages).
International Search Report and Written Opinion, mailed May 7, 2007, for Application No. PCT/IB2006/003130, filed Jun. 30, 2006.
International Search Report and Written Opinion, mailed Jun. 11, 2007, for Application No. PCT/IB2006/003123, filed Jun. 30, 2006.
Greenwald et a. J. Med. Chem. 2004. 47: 726-734.
Ratcliffe et al. Mod. Pathol. 1997. 10(12): 1247-1252.

Figure 1a | Figure 1b | Figure 1c
Recognition Unit 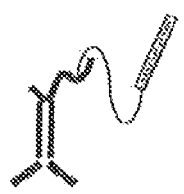
Adaptor Unit 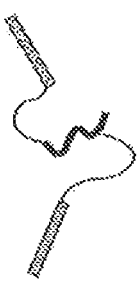
Detection Unit 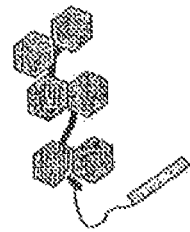

Figure 7a
Figure 7b
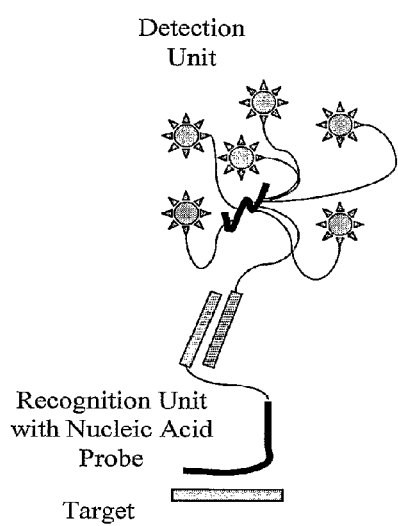
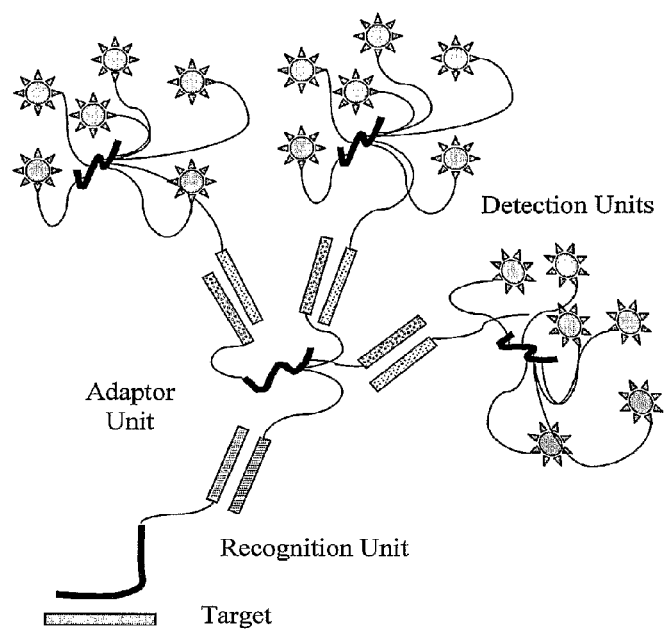

Target 1  Target 2  Target 3
(antigen) (antigen) (nucleic acid sequence)

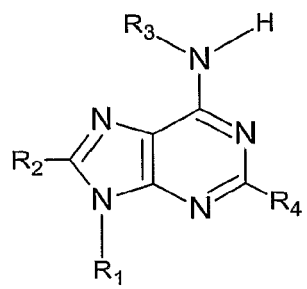
Figure 18a, Adenine, A
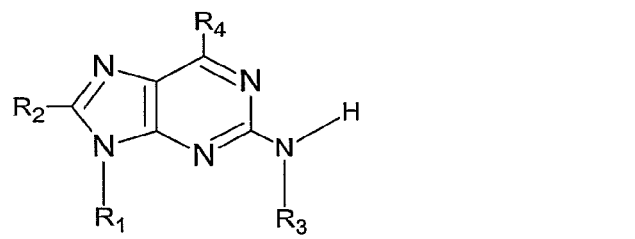
Figure 18b, isoAdenine, isoA
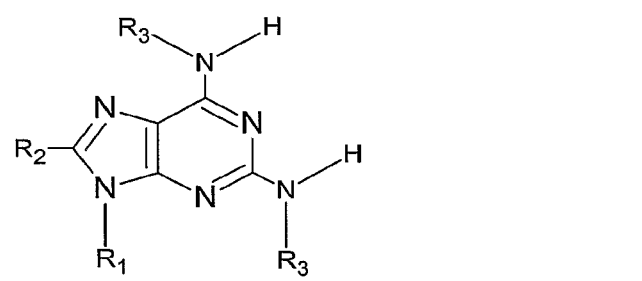
Figure 18c, Diaminopurine, D

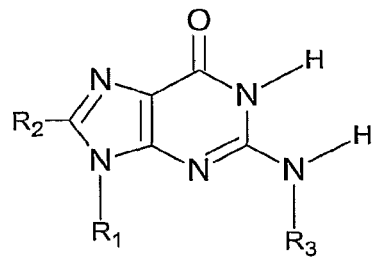
Figure 18d, Guanine, G
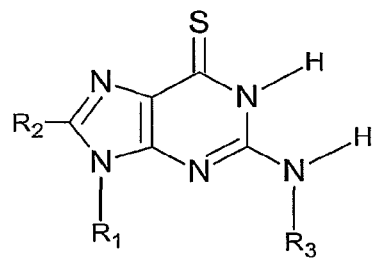
Figure 18e, ThioGuanine, Gs
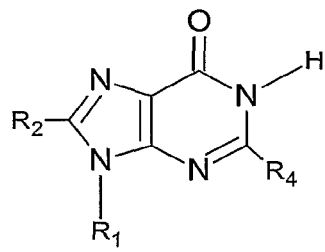
Figure 18f, Inosine, I
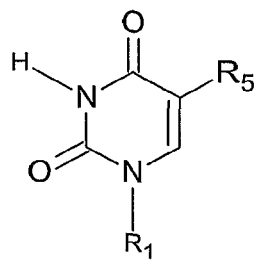
Figure 18g, Uracil, U

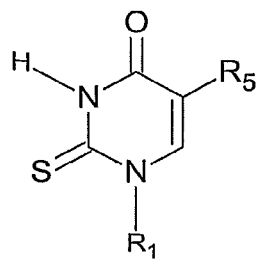
Figure 18h, 2-ThioUracil, U2s
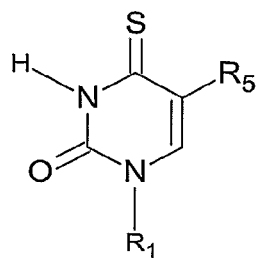
Figure 18i, 4-ThioUracil, U4s
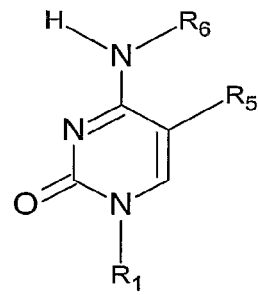
Figure 18j, Cytosine, C
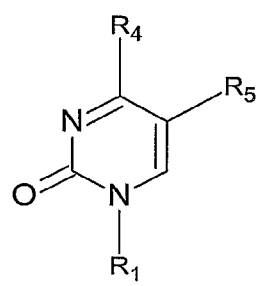
Figure 18k, 2-oxo-Pyrimidine, Py-2o

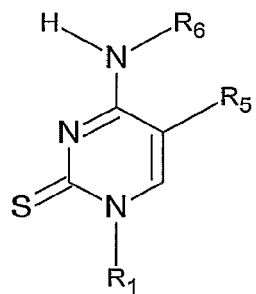
Figure 18l, ThioCytosine, Cs
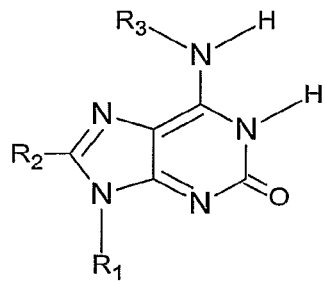
Figure 18m, isoGuanine, isoG
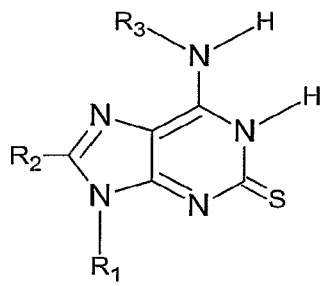
Figure 18n, isothioGuanine, isoGs
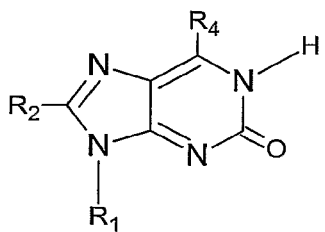
Figure 18o, 2-oxoPurine, Pu-2o

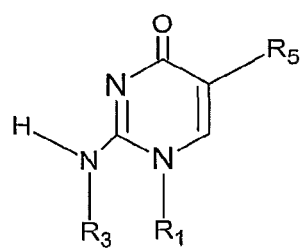
Figure 18p, isoCytosine, isoC
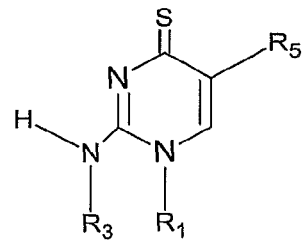
Figure 18q, isothioCytosine, isoCs
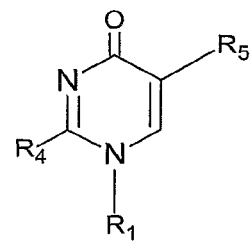
Figure 18r, 4-oxoPyrimidine, Py-4o

Figure 19

| | Adenines | 6-aminopurines | 2,6-diaminopurines | Guanines | Inosines | 6-Thioguanines | isoguanines | iso-2-thioguanines | 2-oxo-purines | Uracils | 2-thioxouracils | 4-thioxouracils | cytosine | 2-thioxocytosine | 2-oxo-pyrimidines | isocytosine | iso-4-thioxocytosine | 4-oxo-pyrimidines |
|---|---|---|---|---|---|---|---|---|---|---|---|---|---|---|---|---|---|---|
| Adenines | | | | | | | | | | 2 | 2 | | | | | | | |
| 6-aminopurines | | | | | | | | | | 2 | | | | | | | | |
| 2,6-diaminopurines | | | | | | | | | | 3 | | 2 | | | | | | |
| Guanines | | | | | | | | | | | | | 3 | | | | | |
| Inosines | | | | | | | | | | | | | 2 | 2 | | | | |
| 6-Thioguanines | | | | | | | | | | | | | 2 | | 1 | | | 2 |
| isoguanines | | | | | | | | | | | | | | | | 3 | 2 | |
| iso-2-thioguanines | | | | | | | | | | | | | | | | 2 | 2 | |
| 2-oxo-purines | | | | | | | | | | | | | | | | 1 | | |
| Uracils | 2 | 2 | 3 | | | | | | | | | | | | | | | |
| 2-thioxouracils | 2 | | | | | | | | | | | | | | | | | |
| 4-thioxouracils | | | 2 | | | | | | | | | | | | | | | |
| cytosine | | | | 3 | 2 | 2 | | | | | | | | | | | | |
| 2-thioxocytosine | | | | | 2 | | | | | | | | | | | | | |
| 2-oxo-pyrimidines | | | | | | 1 | | | | | | | | | | | | |
| isocytosine | | | | | | | 3 | 2 | 1 | | | | | | | | | |
| iso-4-thioxocytosine | | | | | | | 2 | 2 | | | | | | | | | | |
| 4-oxo-pyrimidines | | | | | | 2 | | | | | | | | | | | | |

IMMUNOHISTOCHEMISTRY DETECTION METHOD

REFERENCE TO RELATED APPLICATIONS

This application is a divisional of U.S. application Ser. No. 11/993,528, which entered the national stage Dec. 21, 2007, and completed the national stage entry requirements on Mar. 17, 2010, and which issued as U.S. Pat. No. 8,741,566 on Jun. 3, 2014. U.S. application Ser. No. 11/933,528 is a national stage filing under 35 U.S.C. §371 of International Application No. PCT/IB2006/003130, filed Jun. 30, 2006, and designating the United States of America. International Application No. PCT/IB2006/003130 is based on and claims the benefit of priority from expired United States Provisional Application Nos. 60/695,408, 60/695,409, and 60/695,410, each of which was filed Jul. 1, 2001 . All of these applications are incorporated herein by reference.

BACKGROUND AND SUMMARY OF THE INVENTION

This international application claims priority to three U.S. Provisional Patent Application Nos. 60/695,408; 60/695,409; and 60/695,410; each of which was filed on Jul. 1, 2005. All of those applications are incorporated herein by reference.

The invention provides compositions and methods for the detection of targets in a sample, including an immunohistochemistry (IHC) sample. Probes and detectable labels may be provided in multiple layers in order to increase the flexibility of a detection system, and to enhance the signal from a target. The compositions and methods are compatible with a variety of detection systems, and with many different types of targets, probes, and detectable labels.

Detection of a target in a sample may ordinarily be achieved by contacting the target with a probe that specifically recognizes it. The probe may be linked, either directly or indirectly to a detectable label, such as a fluorophore or radioactive tag, which provides a signal representing the target.

Some detection systems also provide ways of enhancing the signal from the target. For example, the label's signal may be enhanced by increasing the number of detectable labels used to detect each target, or by instrumentation that may amplify the signal. Alternatively, if the target is an antigen, a multiple-antibody system may amplify the detection signal. For instance, the target may first be bound by a primary antibody, which, in turn, is capable of binding many secondary antibodies or even tertiary antibodies, which, in their turn, bind to the probe. This method, thus, increases the number of probes that recognize each antigen target by adding extra layers of molecular interactions between the probe and target.

The secondary antibody technique is widely used, but may be limited due to, for example i) the availability of the secondary antibodies; ii) unwanted cross reactivity between closely related species, e.g. rat, mouse; iii) the size of antibodies reduces the penetration of the reagents. Furthermore, conjugation of antibodies to other antibodies, enzymes, color labels, etc. Is somewhat unique for every antibody due to biological variations. Fab or Fab2 fragments of IgG have been used to overcome the size and non-specific binding problems, but such secondary antibody based visualization systems still remain limited to staining of one, two or three different targets. Amplification of the signal from individual targets is both laborious and complex due to the above-mentioned technical limitations. Further, currently used antibody-based amplification methods may only be of practical use with certain types of targets and detectable labels. In contrast, the Instant invention uses the flexibility of nucleic acid hybridization to provide a general set of compositions and methods that may be used to detect one or many targets in a sample and amplify their signals.

The instant methods and compositions may also provide for increased flexibility as compared to, for example, capture assays or sandwich assays, such as those described in U.S. Pat. No. 4,868,105, for example, that rely on one type of binding interaction such as a hapten-protein or primary antibody-secondary antibody interaction. The ability to design a variety of nucleic acid analog hybridization pairs, for instance, may dramatically increase the ways in which the probe and detectable label may interact.

In some embodiments of the invention, compositions and methods may separate the probe and the detectable label such that they may be comprised on different units within a detection system. See, for example, FIG. 1a and 1c. The units may then interact through specific hybridization of nucleic acid analog segments. The units may be designed such that a given probe may interact with a variety of different detectable labels, depending upon the needs of the assay. The units may also be designed to include multiple interacting nucleic acid analog segments, either to increase the affinity between the units, or to amplify a signal. Further, adaptor units may be included that provide, for example, one or more additional molecular layers between the probe and the detectable label. See FIG. 1b. In some embodiments, the adaptor units may allow for even greater mixing and matching of probes and labels as well as additional amplification of a signal. The components of the instant compositions may also be designed to be of similar chemical compositions so that they may be prepared simply using standardized conjugation schemes.

Due to the relative ease with which nucleic acid hybridization schemes may be planned, the methods and compositions of the invention may also be used to detect more than one target within a sample. For instance, multiple targets in a sample are not always expressed in equal amounts. Thus, there may be a differential need for amplification. The instant invention is also useful in normalizing the detection of two or more targets in a system.

The system may also be designed such that one unit specifically hybridizes to more than one other unit. For instance, the various units of the invention may be designed such that one unit hybridizes to several other units, for example, by providing multiple nucleic acid analog segments on the same unit. Alternatively, certain nucleic acid analogs may allow for degenerate hybridization schemes such that one nucleic acid analog segment may specifically hybridize to more than one other nucleic acid analog segment, creating a "master key" unit. (See the international application entitled "New Nucleic Acid Base Pairs" submitted herewith, for an example of such segments.) This unique feature increases the flexibility of the instant compositions and methods even further.

Moreover, the instant compositions and methods are compatible with a large variety of samples and are adaptable to a large number of targets, probes, and detectable labels. The present invention is useful in immunohistochemistry applications (IHC), but can be applied to other detection methods as well. Other detection that may be compatible with this invention include, for example, immunocytochemistry (ICC), in situ hybridization (ISH), flow cytometry, enzyme immunoassays (EIA), enzyme linked immuno-assays (ELISA), blotting methods (e.g. Western, Southern, and Northern), labeling inside electrophoresis systems or on surfaces or arrays, and precipitation, among others. Such detection formats, for example, are useful in research as well as in diagnosing diseases or conditions. Further, if multiple targets are detected, such systems may be useful in analyzing expression patterns of genes or levels of proteins within a sample.

It is to be understood that both the foregoing general description and the following detailed description are exemplary and explanatory only and are not restrictive of the invention, as claimed. Additional objects and advantages of the invention will be set forth in part in the description which follows, and in part will be obvious from the description, or may be learned by practice of the invention.

BRIEF DESCRIPTION OF THE DRAWINGS

The accompanying drawings, which are incorporated in and constitute a part of this specification, illustrate one several non-limiting embodiments of the invention.

FIG. 1a illustrates an exemplary recognition unit according to the invention, comprising a nucleic acid analog segment (shaded bar), a linker (thin line), a polymer (thick line), and an antibody probe (upside-down Y shape).

FIG. 1b illustrates an exemplary optional adaptor unit according to the invention, comprising two nucleic acid analog segments (shaded bars), linkers (thin lines), and a polymer (thick line).

FIG. 1c illustrates an exemplary detection unit according to the invention, comprising detectable labels (shaded octagons), polymers (thick lines), a linker (thin line), and a nucleic acid analog segment (shaded bar).

In FIG. 6a, a target antigen is recognized by a recognition unit comprising a primary antibody as probe and two nucleic acid analog segments. The nucleic acid analog segments specifically hybridize to two detection units comprising detectable labels (shaded circles). In FIG. 6b, the recognition unit comprises a secondary antibody as probe, which recognizes a primary antibody bound to the target. In FIGS. 6a and 6b, further nucleic acid analog segments on the detection units shown in different shading may serve to specifically hybridize to other detection units, for example, to further amplify the signal.

FIGS. 7a and 7b show two exemplary embodiments according to the invention for detection of nucleic acid segments. FIG. 7a illustrates a two-layer system in which a target nucleic acid segment is recognized by a recognition unit comprising a nucleic acid or nucleic acid analog as probe and a nucleic acid analog segment that specifically hybridizes to a detection unit. The detection unit comprises multiple fluorophores (flower shapes) conjugated to a polymer (thick line) via several linkers (thin lines). FIG. 7b illustrates a three-layer system in which the recognition unit specifically hybridizes to an adaptor unit comprising several nucleic acid analog segments, which in turn, serve to link several detection units to the recognition unit and the target in order to further enhance the signal from the target.

FIG. 8a shows an exemplary two-layer system such that the recognition unit comprises three different nucleic acid analog segments. FIG. 8b shows an exemplary three-layer system with an alternative recognition unit comprising three different nucleic acid analog segments, each attached to the probe via different linkers. These arrangements allow a single recognition unit to specifically hybridize to several different adaptor units as well as many different detection units, allowing for different methods of enhancing the signal.

FIG. 18 (a-r): Examples of non-natural bases that may be used in the nucleic acid analog segments of the invention, and their names and symbols. Where:

R1 denotes the attachment point to the backbone

R2 is, for example, substituents in the 8-position of purines: such as hydrogen, halogens, or other small substituents i.e., methyl, ethyl.

R3 is, for example, substituents on hydrogen bonding exocyclic amino groups on bases other than cytosine: such as hydrogen, methyl, ethyl, acetyl.

R4 is, for example, substituents that face a carbonyl in place of an aminogroup: such as hydrogen, fluorine and chlorine.

R5 is, for example, substituents in the 5-position of pyrimidines: for example, fluorofors, hydrogen, halogens, and substituted and unsubstituted groups of C1-C20. This position, for example, allows bulky substituents, if desired.

R6 is, for example, substituents on the hydrogen bonding excocylic amino group of cytosine. This position also allows bulky substituents, for example, alkyl, acyl, and substituted and unsubstituted groups of C1-C20.

FIG. 19 shows interactions between each of the 18 bases shown in FIG. 1: 3 refers to three hydrogen bonds being present between the bases; 2 refers to two hydrogen bonds being present between the bases; 1 is the presence of one hydrogen bond; and X is a repulsion or no H bonding between the pairs. There are 3 three bond base pairs, 12 two bond base pairs, and 2 single bond base pairs. As may be seen from the figure and the text below, these pairing schemes may be used to expand the normal genetic code and thus may allow nucleic acid analog segments to specifically hybridize to more than one other nucleic acid analog segment within the instant recognition, adaptor, and detection units of the invention.

Figure 20:
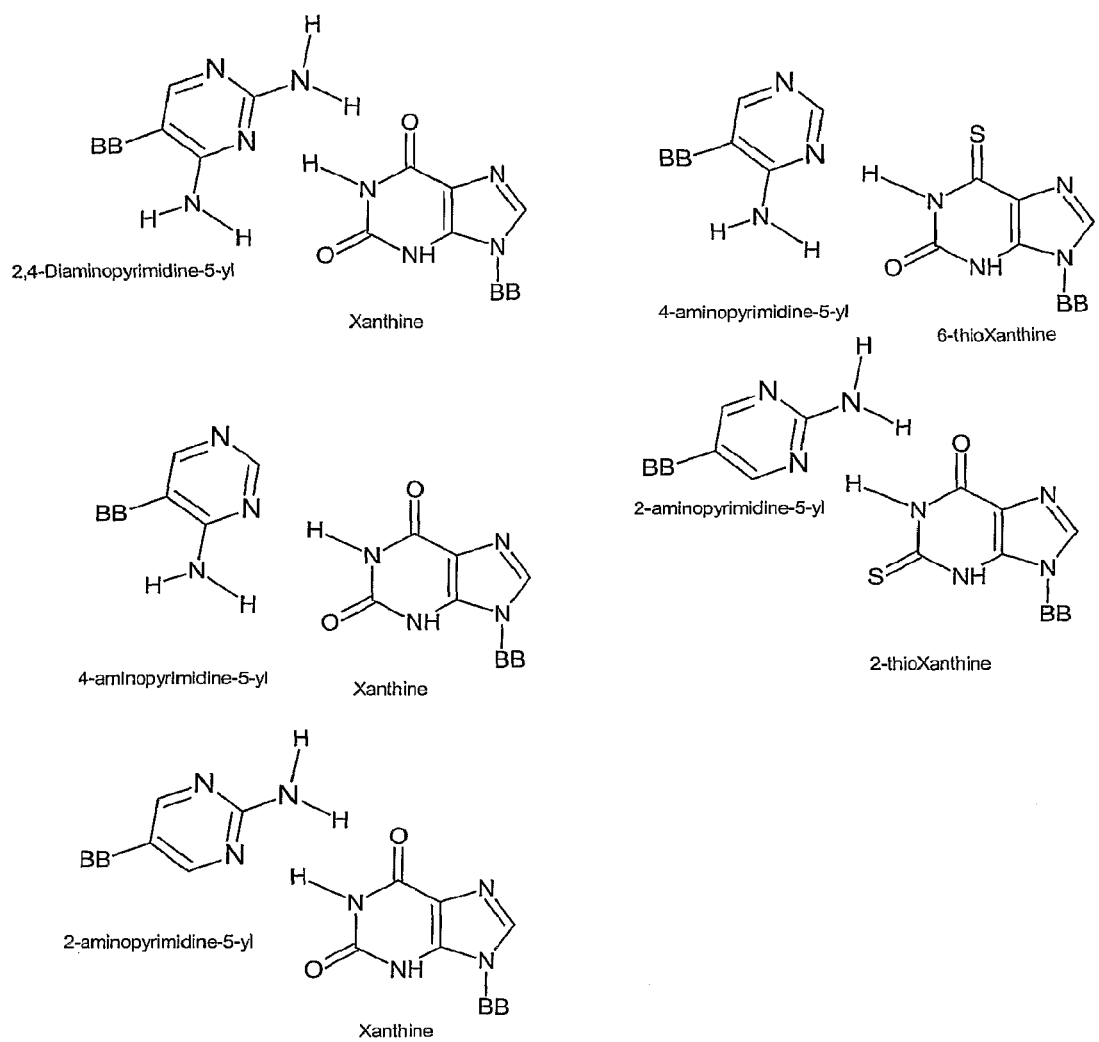

FIG. 20 depicts yet other non-natural bases and base-pairings that may be used in the inventive compositions and methods.

See U.S. Provisional Application No. 60/695,409, and a related co-pending International Application entitled "New Nucleic Acid Base Pairs" for additional information on these non-natural pairing schemes both of which are hereby incorporated by reference herein.

DETAILED DESCRIPTION OF THE INVENTION

A. Definitions

Sample, as used herein, refers to any composition potentially containing a target.

Target, as used herein, refers to any substance present in a sample that is capable of detection.

According to this invention, a recognition unit, is a substance that recognizes at least one target in a sample. In some embodiments, the recognition unit comprises a probe, which, as defined herein, comprises any substance that is capable of recognizing a target. In some embodiments of this invention, a recognition unit also comprises at least one nucleic acid analog segment. In some embodiments, the recognition unit may also comprise at least one polymer and/or at least one linker.

The terms recognize, recognition, or recognizing, etc., as used herein, mean an event in which one substance, such as a probe or recognition unit comprising a probe, directly or indirectly interacts with a target in any way such that the interaction with the target may be detected by a detection unit. In some nonlimiting examples, a probe may react with a target, or directly bind to a target, or indirectly react with or bind to a target by directly binding to another substance that in turn directly binds to or reacts with a target.

As used herein, a detection unit refers to a substance comprising at least one detectable label, and capable of binding directly to a recognition unit or indirectly to a recognition unit through an optional adaptor unit. In some embodiments of this invention, a detection unit also comprises at least one nucleic acid analog segment. In some embodiments, the detection unit may also comprise at least one polymer and/or at least one linker.

An adaptor unit, as used herein, means a substance that is capable of linking a recognition unit to a detection unit. In some embodiments of this invention, an adaptor unit comprises at least two nucleic acid analog segments. In some embodiments, the adaptor unit may also comprise at least one polymer and/or at least one linker.

The terms specifically hybridizes, specific hybridization, and the like, as used in this application, mean the formation of hydrogen bonds between two or more nucleic acid segments or nucleic acid analog segments under at least low stringency conditions. Non-limiting examples of the formation of hydrogen bonds between the segments include the formation of Watson-Crick, wobble, and Hoogsteen base-pair geometries, such as to form double strands.

A primary binding agent as used herein, refers to a substance that binds directly to a target in a sample.

A secondary binding agent, as used herein, refers to a substance which binds directly to a primary binding agent.

A tertiary binding agent, as used herein, refers to a substance which specifically binds a secondary binding agent.

Antibody, as used herein, means an immunoglobulin or a fragment thereof, and encompasses any polypeptide comprising an antigen-binding site regardless of the source, method of production, and other characteristics.

An antigen, as used herein, refers to any substance recognized by an antibody.

According to this invention, a detectable label is any molecule or functional group that allows for the detection of the presence of the target in the sample.

As used herein, the terms base and nucleobase refer to any purine-like or pyrimidine-like molecule that may be comprised in a nucleic acid segment or nucleic acid analog segment.

As used herein, a nucleic acid segment refers to a nucleobase sequence comprising any oligomer, polymer, or polymer segment, having a backbone formed solely from RNA or DNA nucleosides and comprising only the bases adenine (A), cytosine (C), guanine (G), thymine (T), and uracil (U), wherein an oligomer means a sequence of two or more nucleobases.

A non-natural base, as used herein, means any nucleobase other than: Adenine, A; Guanine, G; Urasil, U; Thymine, T; Cytosine, C.

A non-natural backbone unit includes any type of backbone unit to which a nucleobase may be attached that is not a ribose-phosphate (RNA) or a deoxyribose-phosphate (DNA) backbone unit.

As used herein, a nucleic acid analog segment means any oligomer, polymer, or polymer segment, comprising at least one monomer that comprises a non-natural base and/or a non-natural backbone unit.

As used herein, all numbers are approximate, and may be varied to account for errors in measurement and rounding of significant digits.

B. Compositions

1. Recognition, Detection, and Adaptor Units

Certain embodiments of this invention provide compositions useful for detecting at least one target in a sample. In some embodiments, the invention provides for a composition comprising a recognition unit and a detection unit wherein:
  a) each unit comprises at least one nucleic acid analog segment;
  b) at least one nucleic acid analog segment of the recognition unit specifically hybridizes to at least one nucleic acid analog segment of the detection unit;
  c) the recognition unit further comprises at least one probe which recognizes at least one target in a sample;
  d) the detection unit further comprises at least one detectable label; and
  e) the nucleic acid analog segments on the recognition unit and detection unit that specifically hybridize to other nucleic acid analog segments on the recognition unit and detection unit do not specifically hybridize to the probe, detectable label, or target.

FIG. 1a and 1c, for example, illustrate exemplary recognition units and detection units, while other non-limiting examples are provided in FIGS. 2-17 and elsewhere in the application as a whole.

Other embodiments of the invention provide for a composition comprising at least one recognition unit, at least one detection unit, and at least one adaptor unit, wherein:
  a) each unit comprises at least one nucleic acid analog segment;
  b) at least one nucleic acid analog segment of the recognition unit specifically hybridizes to at least one nucleic acid analog segment of the adaptor unit and at least one nucleic acid analog segment of the adaptor unit specifically hybridizes to at least one nucleic acid analog segment of the detection unit;
  c) the recognition unit further comprises at least one probe which recognizes at least one target in a sample;
  d) the detection unit further comprises at least one detectable label; and
  e) the nucleic acid analog segments on the recognition unit, adaptor unit, and detection unit that specifically hybridize to other nucleic acid analog segments on the recognition unit, adaptor unit, and detection unit do not specifically hybridize to the probe, detectable label, or target.

Adaptor units may serve to link recognition units and detection units together. FIG. 1b depicts an exemplary adaptor unit according to the invention, while other examples are illustrated in FIGS. 3, 5-12, and 14-17, and throughout the application as a whole.

In some embodiments, an adaptor unit has two nucleic acid analog segments, one to hybridize specifically to a recognition unit and another to hybridize specifically to a detection unit. In other embodiments, an adaptor unit has more than two nucleic acid analog segments, either multiple segments of the same sequence or multiple different sequences. In some embodiments, the adaptor units may further be used to link one type of recognition unit to more than one different detection unit, or vice versa. For example, in some embodiments, adaptors may function as "master keys" to connect one recognition unit to several different detector units, for instance, detection units with different kinds of detectable labels. Alternatively, adaptor units may link one detector unit to several different kinds of recognition units, and thus to several different kinds of probes. In other embodiments, adaptor units may also serve to enhance the signal from recognition of a target. For instance, an adaptor unit with several copies of the same nucleic acid analog segment may specifically hybridize to several detector units, thus increasing the number of detectable labels linked to a given target in a sample.

In certain embodiments, two or more of the recognition, adaptor, and detection units may be pre-hybridized prior to bringing the composition into contact with the sample.

2. Nucleic Acid Analog Segments

The nucleic acid analog segments present on the recognition, detection, and optional adaptor units may comprise at least one non-natural base and/or a non-natural backbone unit within the segment as a whole. Such non-natural units thus include, but are not limited to, for example, PNA's or phosphorothioate or 2'O-methyl nucleosides comprising the one of the natural bases A, C, G, T, or U, and, for example, natural RNA or DNA nucleosides comprising non-natural base such as 4-thio-Uracil or Inosine.

Non-natural bases may include, for example, purine-like and pyrimidine-like molecules, such as those that may interact using Watson-Crick-type, wobble, or Hoogsteen-type pairing interactions. Examples include generally any nucleobase referred to elsewhere as "non-natural" or as an "analog."

Examples include: halogen-substituted bases, alkyl-substituted bases, hydroxy-substituted bases, and thiol-substituted bases, as well as 5-propynyl-uracil, 2-thio-5-propynyl-uracil, 5-methylcytosine, isoguanine, isocytosine, pseudoisocytosine, 4-thiouracil, 2-thiouracil and 2-thiothymine, inosine, 2-aminopurine, N9-(2-amino-6-chloropurine), N9-(2,6-dlaminopurine), hypoxanthine, N9-(7-deaza-guanine), N9-(7-deaza-8-aza-guanine) and N8-(7-deaza-8-aza-adenine).

Yet other examples include bases in which one amino group with a hydrogen is substituted with a halogen (small "h" below), such as 2-amino-6-"h"-purines, 6-amino-2-"h"-purines, 6-oxo-2-"h"-purines, 2-oxo-4-"h"-pyrimidines, 2-oxo-6-"h"-purines, 4-oxo-2-"h"-pyrimidines. Those will form two hydrogen bond base pairs with non-thiolated and thiolated bases; respectively, 2,4 dioxo and 4-oxo-2-thioxo pyrimidines, 2,4 dioxo and 2-oxo-4-thioxo pyrimidines, 4-amino-2-oxo and 4-amino-2-thioxo pyrimidines, 6-oxo-2-amino and 6-thioxo-2-amino purines, 2-amino-4-oxo and 2-amino-4-thioxo pyrimidines, and 6-oxo-2-amino and 6-thioxo-2-amino purines.

For example, some specific embodiments of non-natural bases are the structures shown in FIG. 18 with the following substituents, which are described in the examples that follow.

| Base (Symbol) | R2 | R3 | R4 | R5 | R6 |
|---|---|---|---|---|---|
| A | H or $CH_3$ | H | H | | |
| IsoA | H or $CH_3$ | H | H | | |
| D | H or $CH_3$ | H | | | |
| G | H or $CH_3$ | H | | | |
| Gs | H or $CH_3$ | H | | | |
| I | H or $CH_3$ | | H | | |
| U | | | | H or $CH_3$ | |
| U2s | | | | H or $CH_3$ | |
| U4s | | | | H or $CH_3$ | |
| C | | | | H or $CH_3$ | H |
| Py-2o | | | H or $CH_3$ | H or $CH_3$ | |
| Cs | | | | H or $CH_3$ | H |
| isoG | H or $CH_3$ | H | | | |

| Base (Symbol) | R2 | R3 | R4 | R5 | R6 |
|---|---|---|---|---|---|
| isoGs | H or $CH_3$ | H | | | |
| Pu-2o | H or $CH_3$ | | H | | |
| isoC | | H | | H or $CH_3$ | |
| isoCs | | H | | H or $CH_3$ | |
| Py-4o | | | H or $CH_3$ | H or $CH_3$ | |
| A | H or $CH_3$ | H | $CH_3$ | | |
| isoA | H or $CH_3$ | H | $CH_3$ | | |
| D | H or $CH_3$ | $CH_3$ | | | |
| G | H or $CH_3$ | $CH_3$ | | | |
| Gs | H or $CH_3$ | $CH_3$ | | | |
| I | H or $CH_3$ | | $CH_3$ | | |
| U | | | | H or $CH_3$ | |
| U2s | | | | H or $CH_3$ | |
| U4s | | | | H or $CH_3$ | |
| C | | | | H or $CH_3$ | CH3 |
| Py-2o | | | H or CH3 | H or $CH_3$ | |
| Cs | | | | H or $CH_3$ | CH3 |
| isoG | H or $CH_3$ | $CH_3$ | | | |
| isoGs | H or $CH_3$ | $CH_3$ | | | |
| Pu-2o | H or $CH_3$ | | $CH_3$ | | |
| isoC | | $CH_3$ | | H or $CH_3$ | |
| isoCs | | $CH_3$ | | H or $CH_3$ | |
| Py-4o | | | H or $CH_3$ | H or $CH_3$ | |

In other examples, one or more of the H or CH3 are independently substituted with a halogen such as Cl or F. Other example non-natural bases and base-pairs are shown in FIG. 20 herein. $R_1$ or "BB" in the structures of FIGS. 18-20 may serve as a point of attachment to a backbone group, such as PNA, DNA, RNA, etc.

In some embodiments, the following types of base pairs are used: one or more of Us:A, T:D, C:G, and P:Gs. In some embodiments, T:A and P:G are used. Still other examples are illustrated in FIGS. 2(A) and 2(B) of Buchardt et al. (U.S. Pat. No. 6,357,163).

Nucleic acid analog segments also include any oligomer, polymer, or polymer segment, comprising at least one monomer with a non-natural backbone unit: in other words, any backbone unit that is not a phosphoribo (RNA) or a phosphodeoxyribo (DNA) unit. Such non-natural backbone units include, but are not limited to, for example PNA's or phosphorothioate or 2'O-methyl backbones. For example, in some embodiments, one or more phosphate oxygens may be replaced by another molecule, such as sulfur. In other embodiments, a different sugar or a sugar analog may be used, for example, one in which a sugar oxygen is replaced by hydrogen or an amine, or an O-methyl. In yet other embodiments, nucleic acid analog segments comprise synthetic molecules that can bind to a nucleic acid or nucleic acid analog. For example, a nucleic acid analog may be comprised of peptide nucleic acids (PNAs), locked nucleic acids (LNAs), or any derivatized form of a nucleic acid. Such backbone units may be attached to any base, including the natural bases A, C, G, T, and U, and non-natural bases.

As used herein, "peptide nucleic acid" or "PNA" means any oligomer or polymer comprising at least one or more PNA subunits (residues), including, but not limited to, any of the oligomer or polymer segments referred to or claimed as peptide nucleic acids in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470 6,201,103, 6,228,982 and 6,357,163; all of which are herein incorporated by reference.

The term PNA also applies to any oligomer or polymer segment comprising one or more subunits of the nucleic acid mimics described in the following publications: Lagriffoul et al., *Bioorganic & Medicinal Chemistry Letters*, 4: 1081-1082 (1994); Petersen et al., *Bioorganic & Medicinal Chemistry Letters*, 6: 793-796 (1996); Diderichsen et al., *Tett. Lett.* 37: 475-478 (1996); Fujii et al., *Bioorg. Med. Chem. Lett.* 7: 637-627 (1997); Jordan et al., *Bioorg. Med. Chem. Lett.* 7: 687-690 (1997); Krotz et al., *Tett. Lett.* 36:6941-6944 (1995); Lagriffoul et al., *Bioorg. Med. Chem. Lett.* 4: 1081-1082 (1994); Diederichsen, U., *Bioorganic & Medicinal Chemistry Letters*, 7:1743-1746 (1997); Lowe et al., *J. Chem. Soc. Perkin Trans.* 1, (1997) 1: 539-546; Lowe et al., *J. Chem. Soc. Perkin Trans.* 11: 547-554 (1997); Lowe et al., *J. Chem. Soc. Perkin Trans.* 1 1:5 55-560 (1997); Howarth et al., *J. Org. Chem.* 62:5441-5450 (1997); Altmann, K-H et al., *Bioorganic & Medicinal Chemistry Letters*, 7:1119-1122 (1997); Diederichsen, U., *Bioorganic & Med. Chem. Lett.*, 8:165-168 (1998); Diederichsen et al., *Angew. Chem. Int. Ed.*, 37.302-305 (1998); Cantin et al., *Tett. Lett.*, 38:4211-4214 (1997); Ciapetti et al., *Tetrahedron*, 53:1167-1176 (1997); Lagriffoule et al., *Chem. Eur. J.*, 3: 912-919 (1997); Kumar et al., *Organic Letters* 3(9): 1269-1272 (2001); and the Peptide-Based Nucleic Acid Mimics (PENAMs) of Shah et al. as disclosed in WO96/04000.

As used herein, the term "locked nucleic acid" or "LNA" means an oligomer or polymer comprising at least one or more LNA subunits. As used herein, the term "LNA subunit" means a ribonucleotide containing a methylene bridge that connects the 2'-oxygen of the ribose with the 4'-carbon. See generally, Kurreck, *Eur. J. Biochem.*, 270:1628-44 (2003).

Nucleic acid segments may be synthesized chemically or produced recombinantly in cells (see e.g. Sambrook et al. (1989) *Molecular Cloning: A Laboratory Manual*, 2nd ed. Cold Spring Harbor Press). Methods of making PNAs and LNAs are also known in the art (see e.g. Nielson, 2001, *Current Opinion in Biotechnology* 12:16; Sorenson et al. 2003, *Chem. Commun.* 7(17):2130).

In certain embodiments, one or more of the recognition, adaptor, and detection units according to the invention comprise more than one nucleic acid analog segment. The two segments may have the same or different sequences.

Interactions between nucleic acid analog segments according to this invention may serve to link a recognition unit to a detector unit, either directly, or through the at least one optional adaptor unit. Different nucleic acid analog segments may hybridize, for instance, using Watson-Crick-type, wobble, or Hoogsteen-type base-pairing. Accordingly, the nucleic acid analog segments comprise sequences which allow for hybridization to take place at a desired stringency.

In some embodiments, the nucleic acid analog segments may pair specifically with more that one other nucleic acid analog segment, thereby providing degeneracy to the recognition, detection and/or adaptor units. See, for example, the International Application submitted herewith entitled "New Nucleic Acid Base Pairs," and see the examples below.

This forms the basis for creating systems in which one nucleic acid analog segment may function as a "master-key" with the ability to hybridize to many partners, where each partner may also hybridize to separate nucleic acid analog segments. In that way, for example, a very versatile and flexible detection system may be constructed in some embodiments that allows the user to choose between visualizing several targets via different detectable labels and detection units, or via only one detectable label and detection unit.

3. Detectable Labels

A detectable label according to the invention may include any molecule which may be detected directly or indirectly so as to reveal the presence of a target in the sample. In some embodiments of the invention, a direct detectable label is used. Direct detectable labels may be detected per se without the need for additional molecules. Examples include fluorescent dyes, radioactive substances, and metal particles. In other embodiments of the invention, indirect detectable labels are used, which require the employment of one or more additional molecules. Examples include enzymes that affect a color change in a suitable substrate, as well as any molecule that may be specifically recognized by another substance carrying a label or react with a substance carrying a label. Other examples of indirect detectable labels thus include antibodies, antigens, nucleic acids and nucleic acid analogs, ligands, substrates, and haptens.

Examples of detectable labels which may be used in the invention include fluorophores, chromophores, electrochemiluminescent labels, bioluminescent labels, polymers, polymer particles, bead or other solid surfaces, gold or other metal particles or heavy atoms, spin labels, radioisotopes, enzyme substrates, haptens, antigens, Quantum Dots, aminohexyl, pyrene, nucleic acids or nucleic acid analogs, or proteins, such as receptors, peptide ligands or substrates, enzymes, and antibodies (including antibody fragments).

Some detectable labels according to this invention comprise "color labels," in which the target is detected by the presence of a color, or a change in color in the sample. Examples of "color labels" are chromophores, fluorophores, chemiluminescent compounds, electrochemiluminescent labels, bioluminescent labels, and enzymes that catalyze a color change in a substrate. In some embodiments, more than one type of color may be used, for instance, by attaching distinguishable color labels to a single detection unit or by using more than one detection unit, each carrying a different and distinguishable color label.

"Fluorophores" as described herein are molecules that emit detectable electro-magnetic radiation upon excitation with electro-magnetic radiation at one or more wavelengths. A large variety of fluorophores are known in the art and are developed by chemists for use as detectable molecular labels and can be conjugated to the linkers of the present invention. Examples include fluorescein or its derivatives, such as fluorescein-5-isothiocyanate (FITC), 5-(and 6)-carboxyfluorescein, 5- or 6-earboxyfluorescein, 6-(fiuorescein)-5-(and 6)-carboxamido hexanoic acid, fluorescein isothlocyanate, rhodamine or its derivatives such as tetramethylrhodamine and tetramethylrhodamine-5-(and-6)-isothiocyanate (TRITC). Other example fluorophores that could be conjugated to the instant linkers include: coumarin dyes such as (diethyl-amino)coumarin or 7-amino-4-methylcoumarin-3-acetic acid, succinimidyl ester (AMCA); sulforhodamine 101 sulfonyl chloride (TexasRed™ or TexasRed™ sulfonyl chloride; 5-(and-6)-carboxyrhodamine 101, succinimidyl ester, also known as 5-(and-6)-carboxy-X-rhodamine, succinimidyl ester (CXR); lissamine or lissamine derivatives such as lissamine rhodamine B sulfonyl Chloride (LisR); 5-(and-6)-carboxyfluorescein, succinimidyl ester (CFI); fluorescein-5-isothiocyanate (FITC); 7-diethylaminocoumarin-3-carboxylic acid, succinimidyl ester (DECCA); 5-(and-6)-carboxytetramethylrhodamine, succinimidyl ester (CTMR); 7-hydroxycoumarin-3-carboxylic acid, succinimidyl ester (HCCA); 6->fluorescein-5-(and-6)-carboxamidolhexanoic acid (FCHA); N-(4,4-difluoro-5,7-dimethyl-4-bora-3a,4a-diaza-3-indacenepropionic acid, succinimidyl ester; also known as 5,7-dimethylBODIPY™ propionic acid, succinimidyl ester (DMBP); "activated fluorescein derivative" (FAP), available from Molecular Probes, Inc.; eosin-5-isothiocyanate (EITC); erythrosin-5-Isothiocyanate (ErITC); and Cascade™ Blue acetylazide (CBAA) (the O-acetylazide derivative of 1-hydroxy-3,6,8-pyrenetrisulfonic acid). Yet other potential fluorophores useful in this invention include fluorescent proteins such as green fluorescent protein and its analogs or derivatives, fluorescent amino acids such as tyrosine and tryptophan and their analogs, fluorescent nucleosides, and other fluorescent molecules such as Cy2, Cy3, Cy 3.5, Cy5, Cy5.5, Cy 7, IR dyes, Dyomics dyes, phyeoerythrine, Oregon green 488, pacific blue, rhodamine green, and Alexa dyes. Yet other examples of fluorescent labels which may be used in the invention include and conjugates of R-phycoerythrin or aliiophycoerythrin, inorganic fluorescent labels such as particles based on semiconductor material like coated CdSe nanocrystallites.

A number of the fluorophores above, as well as others, are available commercially, from companies such as Molecular Probes, Inc. (Eugene, Oreg.), Pierce Chemical Co. (Rockford, Ill.), or Sigma-Aldrich Co. (St. Louis, Mo.).

Examples of polymer particles labels which may be used in the invention include micro particles, beads, or latex particles of polystyrene, PMMA or silica, which can be embedded with fluorescent dyes, or polymer micelles or capsules which contain dyes, enzymes or substrates.

Examples of metal particles which may be used in the invention include gold particles and coated gold particles, which can be converted by silver stains.

Examples of haptens that may be conjugated in some embodiments are fluorophores, myc, nitrotyrosine, biotin, avidin, strepavidin, 2,4-dinitrophenyl, digoxigenin, bromodeoxy uridine, sulfonate, acetylaminoflurene, mercury trintrophonol, and estradiol.

Examples of enzymes which may be used in the Invention comprise horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase and glucose oxidase (GO).

Examples of commonly used substrates for horse radish peroxidase (HRP) include 3,3'-diaminobenzidine (DAB), diaminobenzidine with nickel enhancement, 3-amino-9-ethyl!carbazole (AEC), Benzidine dihydrochloride (BDHC), Hanker-Yates reagent (HYR), Indophane blue (IB), tetramethylbenzidine (TMB), 4-chloro-1-naphtol (CN), α-naphtol pyronin (α-NP), o-dianisidine (OD), 5-bromo-4-chloro-3-indolylphosphate (BCIP), Nitro blue tetrazolium (NBT), 2-(p-iodophenyl)-3-p-nitrophenyl-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B1-phosphate/fast red TR(NABP/FR), Naphthol-AS-MX-phosphate/fast red TR(NAMP/FR), Naphthol-AS-B1-phosphate/fast red TR(NABP/FR), Naphthol-AS-MX-phosphate/fast red TR(NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b(beta)-d(delta)-galactopyranoside (BCIG).

Examples of luminescent labels which may be used in the invention include luminol, isoluminol, acridinlum esters, 1,2-dioxetanes and pyridopyridazines. Examples of electrochemiluminescent labels include ruthenium derivatives.

Examples of radioactive labels which may be used in the invention include radioactive isotopes of iodide, cobalt, selenium, hydrogen, carbon, sulfur and phosphorous.

In some embodiments the detection unit may comprise from 1 up to 500 detectable label molecules. In some embodiments, the detectable label is an enzyme, which may be conjugated to a polymer, such that the number of enzyme molecules conjugated to each polymer molecule is, for instance, 1 to 200, 2 to 50, or 2 to 25. In some embodiments, the detectable label is a gold particle, a radioactive isotope, or a color label, e.g. a low molecular weight fluorochrome, and the number of detectable labels conjugated to each polymer molecule is, for instance, 1 to 500, or for instance, 2 to 200. In some embodiments, the detectable label is a protein fluorochrome and the number of detectable labels conjugated to each polymer molecule is 1-50, 2-20. In some embodiments, the number of detectable label molecules conjugated to each polymer is 1-200, 2-50, 2-25, or is 10-20, 5-10, or 1-5.

The detectable label can be detected by numerous methods, including, for example, reflectance, transmittance, light scatter, optical rotation, and fluorescence or combinations hereof in the case of optical labels or by film, scintillation counting, or phosphorimaging in the case of radioactive labels. See, e.g., Larsson, 1988, *Immunocytochemistry: Theory and Practice*, (CRC Press, Boca Raton, Fla.); *Methods in Molecular Biology*, vol. 80 1998, John D. Pound (ed.) (Humana Press, Totowa, N.J.). In some embodiments, more than one detectable label is employed.

When more than one color label is used, the different colors may have different, distinguishable colors. In some embodiments both colors can be detected simultaneously, such as by fusion or juxtaposition of the signals, signal enhancement or quenching, or detection of multiple colors in the sample. The exact choice of detectable label or combinations of detectable labels may be based on personal preferences in combinations with restrictions of the sample type, sample preparation method, detection method and equipment, and optional contrasting labels used in the sample.

4. Probes

The instant invention is further compatible with a variety of types of probes, including molecules capable of recognizing a target in a sample either directly or indirectly through another binding agent. In some embodiments, recognition takes place through binding, while in other embodiments, recognition takes place through a chemical reaction or another change in the sample caused by the presence of the target and probe. In some embodiments, the recognition may be direct, such as through non-covalent or covalent binding or reaction between the probe and the target. In other embodiments, the recognition may be indirect, such as through a primary binding agent, or higher level binding agent. For example, in some embodiments, the probe may bind to a primary binding agent, which in turn binds to a target, or a probe may bind to a secondary binding agent, which binds to a primary binding agent, which binds to a target, and so on. In some embodiments, the probe comprises a nucleic acid segment, nucleic acid analog segment, protein (including, for instance, an antibody, receptor protein, or enzyme), ligand, receptor, substrate, or hapten.

5. Binding Agents

In certain embodiments, the invention comprises at least one binding agent, such as a primary binding agent which directly binds to a target in a sample. In embodiments comprising one or more binding agents, the probe may directly bind to one or more of the binding agents rather than to the target itself. In other embodiments, the primary binding agent is an antibody, i.e., a primary antibody. In other embodiments the primary binding agent is a nucleic acid segment or nucleic acid analog segment. In yet other embodiments the primary binding agent is a receptor, hapten, substrate, or a ligand.

Other embodiments of the invention further comprise a secondary binding agent. The secondary binding agent may be any molecule that binds the primary binding agent. For example, in some embodiments the primary binding agent is a primary antibody. In those embodiments, the secondary binding agent may comprise e.g. a secondary antibody, a Fc receptor or Clq, a protein from the classical pathway of the complement cascade. Depending on the primary binding agent, the secondary binding agent may be e.g an anti-hapten antibody, an MHC molecule, such as an MHC class I and MHC class II and non conventional MHC, a molecule having a specific binding partner, such as molecules involved in cellular signaling pathways or molecules having leucine zipper domains, e.g., fos/jun, myc, GCN4, molecules having SH1 or SH2 domains, such as Src or Grb-2. A secondary binding agent may also be comprised of a chimeric or a fusion protein, i.e., a protein engineered to combine the features of two or more specific binding partners. For instance, a leucine zipper could be engineered into an Fc region of an antibody or an SH2 domain could be engineered to be expressed in an Fc region of an antibody. The secondary binding agent may also comprise a hapten, such as fluorophores, myc, nitrotyrosine, biotin, avidin, strepavidin, 2,4-dinitrophenyl, digoxigenin, bromodeoxy uridine, sulfonate, acetylaminoflurene, mercury trintrophonol, and estradiol. The secondary binding agent may comprise a nucleic acid molecule that specifically hybridizes to a complementary nucleic acid molecule of the primary binding agent.

Yet other embodiments of the invention may comprise a tertiary binding agent that binds the secondary binding agent. The tertiary binding agent may comprise, for example, a tertiary antibody or a nucleic acid molecule or any of the specific binding partners described above for the secondary binding agent, so long as it specifically binds the secondary binding agent. Certain embodiments of the invention may further comprise additional forth, fifth, or even higher order, binding agents similar to the binding agents described above.

6. Antibodies as Detectable Labels, Binding Agents, and Probes

Antibodies may be used as detectable labels, binding agents, or probes, for example, in various embodiments of this invention. Some embodiments may comprise, for example, polyclonal, monoclonal, monospecific, polyspecific, humanized, single-chain, chimeric, synthetic, recombinant, hybrid, mutated, and CDR-grafted antibodies. Various techniques for producing antibodies and preparing recombinant antibody molecules are known in the art and have been described, see, e.g., Kohler and Milstein, (1975) *Nature* 256: 495; Harlow and Lane, *Antibodies: a Laboratory Manual*, (1988) (Cold Spring Harbor Press, Cold Spring Harbor, N.Y.). Antibodies used in the invention may be derived from any mammal species, e.g., rat, mouse, goat, guinea pig, donkey, rabbit, horse, lama, camel, or any avian species e.g., chicken, duck. The origin of the antibody is defined by the genomic sequence irrespective of the method of production.

The antibody may be of any isotype, e.g., IgG, IgM, IgA, IgD, IgE or any subclass, e.g., IgG1, IgG2, IgG3, IgG4. The skilled artisan will appreciate that antibodies produced recombinantly, or by other means, for use in the invention include any antibody fragment which can still bind antigen, e.g. an Fab, an $F(ab)_2$, Fv, scFv. in certain embodiments, the antibody, including an antibody fragment, may be recombinantly engineered to include a hapten, e.g, a peptide. In certain embodiments the hapten may be a myc tag (se FIG. 1N). Inclusion of a hapten in an antibody or antibody fragment facilitates subsequent binding of a binding agent, probe, or label Certain embodiments employ a primary antibody containing an antigen binding region which can specifically bind to an antigen target in a sample, such as an IHC sample. Thus, a primary antibody may act as either a primary binding agent or a probe in such embodiments, by directly recognizing the antigen target.

Some embodiments further employ a secondary antibody containing an antigen binding region which specifically binds to the primary antibody, e.g., the constant region of the primary antibody. In certain embodiments, the secondary antibody is conjugated to a polymer. In some embodiments, the polymer is conjugated with 2-20 secondary antibodies. In other embodiments, the polymer is conjugated with 2-10 secondary antibodies. In other embodiments, the polymer is conjugated with 1-5 tertiary antibodies, such as 1, 2, 3, 4, or 5. In some such embodiments, the secondary antibody acts as a secondary binding agent, while in other such embodiments, the secondary antibody acts as a probe, recognizing the target antigen indirectly through a primary antibody.

Some embodiments also employ a tertiary antibody containing an antigen binding region which specifically binds to the secondary antibody, e.g., a constant region of the secondary antibody, or a hapten linked to the secondary antibody or a polymer conjugated to the secondary antibody. In certain embodiments, the tertiary antibody is conjugated to a polymer. In some embodiments, the polymer is conjugated with 1-20 tertiary antibodies. In other embodiments, the polymer is conjugated with 1-5 tertiary antibodies, such as 1, 2, 3, 4, or 5. In some such embodiments, the tertiary antibody acts as a tertiary binding agent, while in other such embodiments, the tertiary antibody acts as a probe, recognizing the target antigen indirectly through a primary and a secondary antibody.

7. Hybridization of Nucleic Acids and Nucleic Acid Analog Segments

Two different nucleic acid analog segments on the recognition unit, detection unit, and/or adaptor unit may specifically hybridize. In some embodiments, the chosen hybridization conditions are "stringent conditions," meaning herein conditions for hybridization and washes under which nucleotide sequences that are significantly complementary to each other remain bound to each other. The conditions are such that sequences at least 70%, at least 80%, at least 85-90% complementary remain bound to each other. The percent complementary is determined as described in Altschui et al. (1997) *Nucleic Acids Res.* 25:3389-3402 (hereby incorporated by reference).

Specified conditions of stringency are known in the art and can be found in *Current Protocols in Molecular Biology*, John Wiley & Sons, Inc. (Ausubel et al. 1995 eds.), sections 2, 4, and 6 (hereby incorporated by reference). Additionally, specified stringent conditions are described in Sambrook et al. (1989) *Molecular Cloning: A Laboratory Manual*, 2nd ed. Cold Spring Harbor Press, chapters 7, 9, and 11 (hereby incorporated by reference).

In other embodiments, the chosen hybridization conditions are "high stringency conditions." An example of high stringency hybridization conditions is hybridization in 4× sodium chloride/sodium citrate (SSC) at 65-70° C. or hybridization in 4×SSC plus 50% formamide at 42-50° C., followed by one or more washes in 1×SSC, at 65-70° C. It will be understood that additional reagents may be added to hybridization and/or wash buffers, e.g., blocking agents (BSA or salmon sperm DNA), detergents (SDS), chelating agents (EDTA), Ficoll, PVP, etc.

In yet other embodiments, the chosen conditions are "moderately stringent conditions." Moderate stringency, as used herein, includes conditions that can be readily determined by those having ordinary skill in the art based on, for example, the length of the nucleic acid analog segment. Exemplified conditions are set forth by Sambrook et al. *Molecular Cloning: A Laboratory Manual,* 2d ed. Vol. 1, pp. 1.101-104, Cold Spring Harbor Laboratory Press (1989) (hereby incorporated by reference), and include use of a prewashing solution of 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

In some embodiments, the chosen conditions are "low stringency" conditions. Low stringency conditions may include, as used herein, conditions that can be readily determined by those having ordinary skill in the art based on, for example, the length of the nucleic acid analog segment. Low stringency may include, for example, pretreating the segment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% W/V dextran sulfate, and $5-20\times10^6$ CPM probe is used. Samples are incubated in hybridization mixture for 18-20 hours at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C.

These different sets of hybridization conditions may also be used when a nucleic acid segment or nucleic acid analog segment is used as a binding agent, a probe, or a detection label.

8. Polymers

One or more of the recognition unit, detection unit, and adaptor unit may also comprise at least one polymer. A "polymer," as used herein, may be any molecule that facilitates covalent or non-covalent attachment of one or more other components of a recognition unit, detection unit, and/or adaptor unit. For instance, the polymer may facilitate the attachment of one or more probes, nucleic acid analog segments, and or detectable labels. The polymer may be a soluble molecule or an insoluble molecule and may have any shape including a linear polymer, branched polymer, bead or other globular shaped polymer.

Examples of suitable polymers include polysaccharides such as dextrans, carboxy methyl dextran, dextran polyaldehyde, carboxymethyl dextran lactone, and cyclodextrins; pulluians, schizophyllan, scleroglucan, xanthan, gellan, O-ethylamino guaran, chitins and chitosans such as 6-O-carboxymethyl chitin and N-carboxymethyl chitosan; derivatized celloiosics such as carboxymethyl cellulose, carboxymethyl hydroxyethyl cellulose, hydroxyethyl cellulose, 6-amino-6-deoxy cellulose and O-ethylamine cellulose; hydroxylated starch, hydroxypropyl starch, hydroxyethyl starch, carrageenans, alginates, and agarose; synthetic polysaccharides such as ficoll and carboxymethylated ficoll; vinyl polymers including poly(acrylic acid), poly(acryl amides), poly(acrylic esters), poly(2-hydroxy ethyl methacrylate), poly(methyl methacrylate), poly(maleic acid), poly (malele anhydride), poly(acrylamide), poly(ethyl-co-vinyl acetate), poly(methaerylic acid), poly(vinylalcohol), poly(vinyl alcohol-co-vinyl chloroacetate), aminated poly(vinyl alcohol), and co block polymers thereof; poly ethylene glycol (PEG) or polypropylene glycol or poly(ethylene oxide-co-propylene oxides) containing polymer backbones including linear, comb-shaped or hyperbranched polymers and dendrimers, including branched PAMAM-dendrimers; poly amino acids including polylysines, polyglutamic acid, polyurethanes, poly(ethylene imines), pluriol; proteins including albumins, immunoglobulins, and virus-like proteins (VLP), and polynucleotides, DNA, PNA, LNA, oligonucleotides and oligonucleotide dendrimer constructs. Also contemplated is the use of mixed polymers, i.e., a polymer comprised of one or more of the above examples including any of the polymers, the co-block polymers and random co-polymers.

Properties of the polymer can be varied, depending on the desired application, to optimize performance. Examples of parameters that may be considered in the choice of a polymer include the length of the polymer and branching of the polymer. Furthermore, the polymer may carry various substituents. The substituents may be chemically protected and/or activated, allowing the polymer to be derivatized further.

9. Linkers

The recognition units, detection units, and adaptor units of the present invention may also comprise one or more linkers. A "linker," as used herein, is a molecule that may help to join other atoms, molecules, or functional groups together through chemical bonds. In the instant applications for example, a linker may serve to join various components of each of the units together, such as probes, nucleic acid analog segments, polymers, and detectable labels.

In some embodiments, the linker also is of sufficient length or size such that the various parts, though chemically attached together, nonetheless remain separated from each other in space, thus minimizing steric clashes. For instance, a linker on a recognition unit may serve to join a probe to a nucleic acid analog segment, while separating them sufficiently to avoid steric clashes. A linker may also serve to separate a polymer from another component of one of the units such as a nucleic acid analog segment, to separate two or more nucleic acid analog segments, or to separate a detectable label from a nucleic acid analog segment, or to separate multiple probes or multiple detectable labels. Linkers may also increase the solubility of the conjugates and may prevent unwanted interactions by shielding the components and may thereby confer a general and significant lower non-specific background for the visualization system.

Reducing the steric hindrance between the various components of the different units of the composition may also improve detection efficiency. For example, certain detection labels show reduced signals when in close proximity to other detection labels. Fluorescent labels, for instance, may become quenched if present in close proximity. Further, reducing steric hindrance increases the binding affinity of the various components for their intended binding partners and decreases the level of the background and the risk of false positive signals.

A person of ordinary skill in the art of molecular conjugation knows numerous linkers. Examples Include 6-aminohexanoic acid, succimidyl 4-(N-malemidomethyl) cylohexane-1-carboxylate (SMCC), homobifunctional linkers such as divinyl sulfone (DVS), glutaric dialdehyde, hexane diisocyanate, dimethylapimidate, 1,5-difluoro-2,4-dinitrobenzene, heterobifunctional linkers like e.g. N-gamma-maleimidobytyroloxy succinimide ester (GMBS), and zero length linkers such as 1-ethyl-3-(3-dimethylaminopropyl)cabodiimide Longer linker molecules based upon polyethylene glycol (PEG) are also available in the art. (See, for example, Discrete PEG (dPEG)™ modification reagents available from Quanta Biodesign, Ltd., Powell, Ohio, or at www.quantablodesiqn.com: PEG-based reagents available from EMD Biosciences, Inc., San Diego, Calif., described in Novabiochem April, 2004, "Product focus: PEG reagents—bifunctional aminoPEG-acid spacers" brochure, available at www.novabiochem.com: and see Baumeister et al., *Biopolymers*, 71: 339 (2003); Kumar & Aldrich, *Org. Lett.*, 5: 613 (2003). (See also, "Chemistry of Protein Conjugation and Cross-Linking" Shan S. Wong CRC Press, Boca Raton, Fla., USA, 1993; "BioConjugate Techniques" Greg T. Hermanson Academic Press, San Diego, Calif., USA, 1996; "Catalog of Polyethylene Glycol and Derivatives for Advanced PEGylation, 2004" Nektar Therapeutics Inc, Huntsville, Ala., USA).

The present invention may also use a long uncharged linker comprising at least two units of the Formula I.

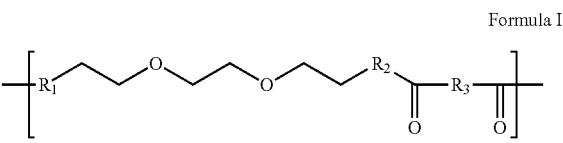

Formula I

In Formula I, $R_1$ and $R_2$ may comprise either NH or O, while $R_3$ may comprise methyl, ethyl, propyl, $CH_2$—O—$CH_2$, and $(CH_2$—O—$CH_2)_2$. For example, in some embodiments of the instant Invention, the linker comprises at least two units of the Formula I wherein $R_1$ and $R_2$ are both NH and $R_3$ is $CH_2$—O—$CH_2$. See the examples that follow and the accompanying International Application entitled "MONOMERIC AND POLYMERIC LINKERS USEFUL FOR CONJUGATING BIOLOGICAL MOLECULES AND OTHER SUBSTANCES" for further description of this linker.

C. Methods of Making Compositions According to the Invention

The recognition units, detection units, and adaptor units according to the invention may comprise, for example, molecules in which the various components such as probes, detection labels, nucleic acid analog segments, linkers, and polymers are covalently attached to form conjugates. As used herein, the terms "conjugate, conjugation" and the like refer to the formation of covalent attachments between various substances, either directly without intervening bonds, or indirectly through at least one intervening bond. Alternatively, in some embodiments, the components of each unit may be attached through stable, non-covalent interactions such as base-pairing, adsorption, intercalation, and similar hydrogen bonding, van der Waals, or hydrophobic interactions, that are sufficiently stable under conditions of use.

Many methods of conjugating molecules are known in the art and can be used to make the various units of the invention. For example, conjugates comprising a linker or polymer according to this invention may be formed by covalently coupling amino groups to conjugated double bonds on a polymer or linker. In one embodiment the polymer is activated with divinylsulfone and mixed with a probe, nucleic acid analog segment, and/or detectable label to form a polymer conjugate. In other embodiments, aldehydes may be used to activate a polymeric backbone. For instance, dextrans may then be mixed with the binding agent and an optional detectable label. Yet another method of preparing polymeric conjugates is by using so called chemo-selective schemes for coupling the components together, e.g., enzymes or other molecules can be derivatized with thiol-reactive maleimide groups before being conjugated to a thiol-modified polymeric carrier or backbone.

In some embodiments no exogenous polymeric backbone is required for attachment of a probe, detectable label, and/or nucleic acid analog segment to one of the instant units. In these embodiments, the components themselves may be activated for conjugation or may be self-polymerizable. For example, a vinyl group may be used to activate the components for conjugation. Polymerization then occurs by addition of a radical, which results in polymerization of the vinyl groups to form a polymeric conjugate. The conjugate thus will contain a poly vinyl backbone or blocks of poly vinyl. Alternatively, active esters of acrylic acid can be used to activate proteins and other molecules. Generation of free radicals can polymerize the derivatized molecules. Small molecule linkers with more than one vinyl group can be further added to help form a polymeric conjugate.

In some embodiments, the components may be organized in the unit with the help of one or more linkers, as described above. Many such linkers are known in the art and available commercially, as described, and the linkers may be activated for attachment to other components of the units according to the invention according to methods available from commercial suppliers or in the literature. See the examples that follow, U.S. Provisional Application Nos. 60/695,408; 60/695,409; and 60/695,410 and the International Application entitled "MONOMERIC AND POLYMERIC LINKERS USEFUL FOR CONJUGATING BIOLOGICAL MOLECULES AND OTHER SUBSTANCES," for examples.

D. Methods

1. General Detection Methods

Some embodiments of the invention comprise methods of detecting a target in a sample comprising:
a) contacting a sample possibly comprising the target with at least one recognition unit comprising at least one probe, such that the probe recognizes the target to form a first complex,
   wherein the recognition unit further comprises at least one nucleic acid analog segment;
b) contacting the first complex of (a) with at least one detection unit comprising at least one nucleic acid analog segment and at least one detectable label,
   wherein at least one nucleic acid analog segment of the recognition unit specifically hybridizes to at least one nucleic acid analog segment of the detection unit to form a second complex, and wherein the nucleic acid analog segments on the recognition unit and the detection unit that hybridize to each other do not specifically hybridize to the probe, detectable label, or target:
c) detecting the second complex of (b); and
d) optionally comparing the signal from the target in the sample with the signal from a reference target or reference sample.

In some embodiments, the detection and/or recognition units may comprise more than one probe, detectable label, nucleic acid analog segment, polymer, or linker. For example, in FIGS. 2 and 4, multiple detectable labels are attached to the detection unit via a polymer.

Figure 2:
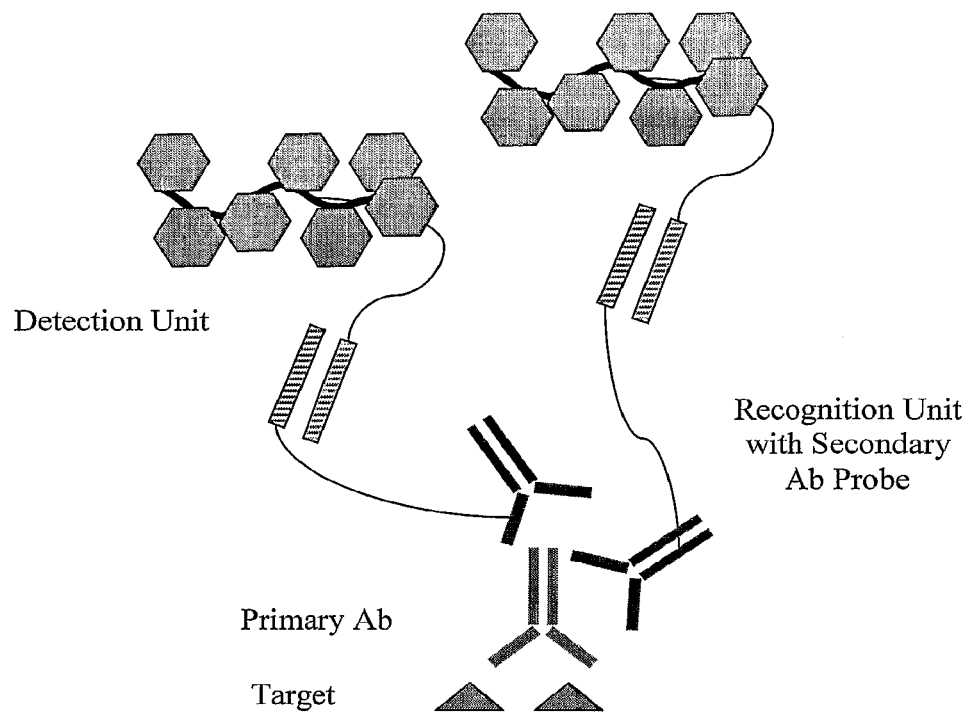
FIG. 2 illustrates an exemplary two-layer method according to the invention in which a target antigen bound to a primary antibody is recognized by a recognition unit comprising a secondary antibody probe. The recognition unit is specifically hybridized to a detection unit via the nucleic acid analog segments on each unit.
Figure 3:
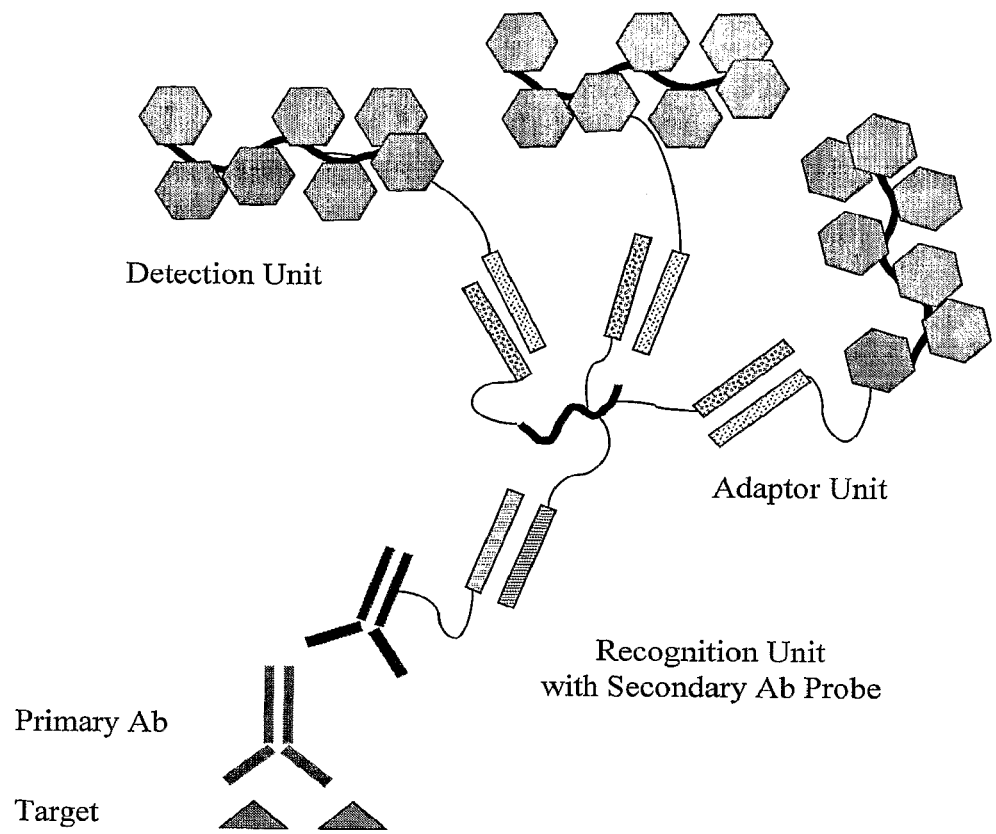
FIG. 3 illustrates an exemplary three-layer method according to the invention wherein a target antigen bound to a primary antibody is recognized by a recognition unit comprising a secondary antibody probe and a nucleic acid analog segment. The recognition unit specifically hybridizes to an adaptor unit comprising nucleic acid analog segments that specifically hybridize to the recognition unit and a detection unit.
Figure 4:
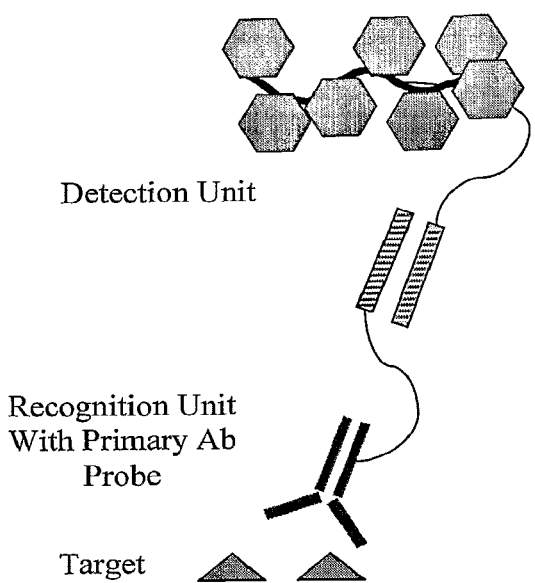
FIG. 4 shows another embodiment according to the invention in which a target antigen is recognized by a recognition unit comprising a primary antibody probe and a nucleic acid analog segment, wherein the nucleic acid analog segment specifically hybridizes to another nucleic acid analog segment on a detection unit.
Figure 5:
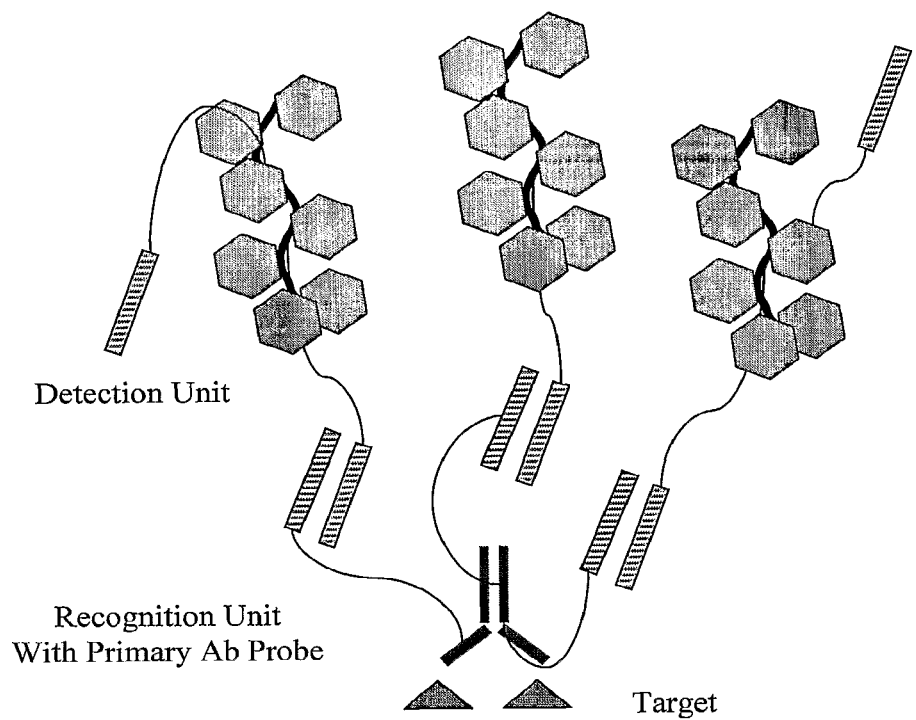
FIG. 5 shows an embodiment wherein a target antigen is recognized by a recognition unit comprising a primary antibody probe and multiple nucleic acid analog segments. Each recognition unit is capable of hybridizing to at least one detection unit.
Figure 6A:
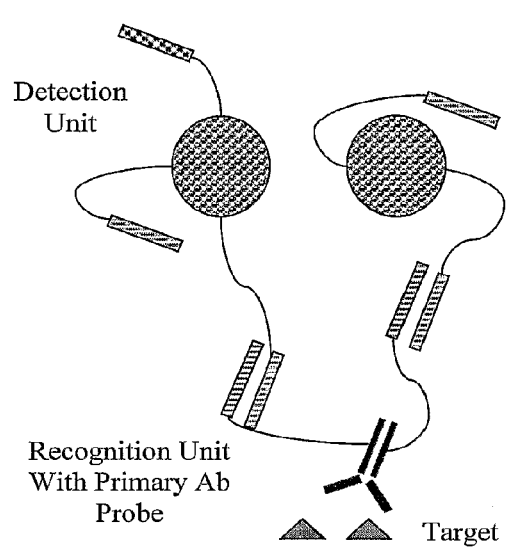
FIGS. 6a and 6b illustrate two methods of enhancing the signal from a target according to the invention.
Figure 6B:
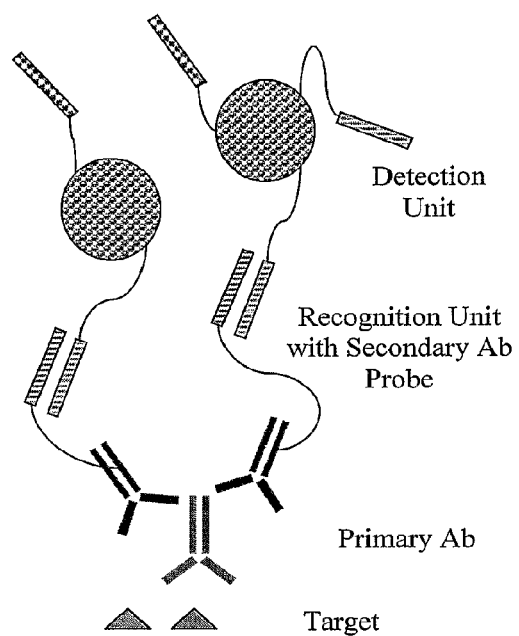

In some embodiments, a recognition unit may comprise a probe that directly binds to the target, as shown in FIG. 4, for example. In other embodiments, the probe may recognize the target by binding to it indirectly, as shown in FIG. 2, in which the probe is a secondary binding agent (e.g. a secondary antibody) that binds to a primary binding agent (e.g. a primary antibody) that in turn directly binds to the target. Such a system may allow for an enhancement of the signal, if, for example, each primary binding agent may be bound to more than one secondary binding agent acting as a probe. If more than one probe recognizes a target, more than one detection unit may become associated with a target, for example. Compare, for example, FIG. 2 to FIG. 4.

In some embodiments of the invention, an optional adaptor unit is used which serves to join the recognition units and detection units. In some embodiments, the invention provides a method of detecting a target in a sample comprising:
a) contacting a sample possibly comprising the target with at least one recognition unit comprising at least one probe and at least one nucleic acid analog segment, such that the probe recognizes the target to form a first complex;
b) contacting the first complex of (a) with at least one adaptor unit comprising at least two nucleic acid analog segments, such that the recognition unit and at least one adaptor unit form a second complex;
c) contacting the second complex of (b) with a detection unit comprising at least one nucleic acid analog segment and at least one detectable label, such that the detection unit recognizes the second complex of (b) and forms a third complex,
   wherein the nucleic acid analog segments comprised on the recognition unit, adaptor unit, and detection unit that specifically hybridize to each other do not specifically hybridize to the probe, detectable label, or target;
d) detecting the third complex of (c); and
e) optionally comparing the signal from the target with the signal from a reference target or reference sample.

The adaptor units may create a third "layer" to the detection system, which may merely connect different recognition and detection units together, while in other embodiments, one or more adaptor units may also serve to further enhance the signal obtained from the target. For example, the adaptor unit may be structured such that it can specifically hybridize to more than one detection unit, thus increasing the number of detection units ultimately joined to a target. See, for example, FIGS. 2 and 3, FIGS. 4 and 5, and FIGS. 7a and 7b. This is useful, for instance, when the amounts of targets are low or when a strong detection signal is desired. In some embodiments, more than one adaptor unit may be used in order to create yet additional layers allowing for further adaptability and amplification. See, for example, FIGS. 9, 10, 11, and 12, each of which use two adaptor units.

Figure 8A:
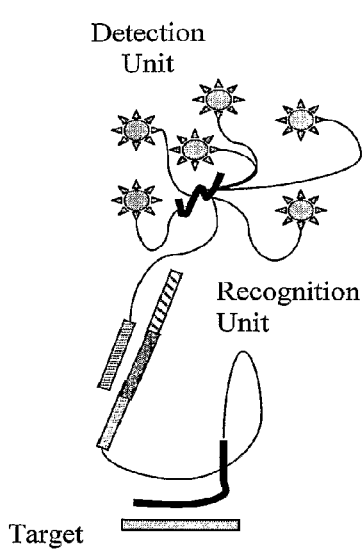
FIGS. 8a and 8b illustrate two other embodiments according to the invention in which the recognition unit comprises several nucleic acid analog segments.
Figure 8B:
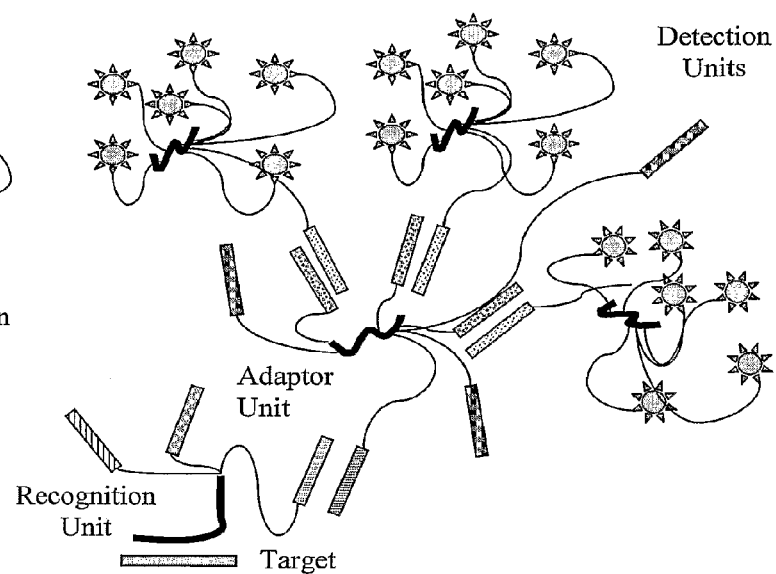
Figure 9:
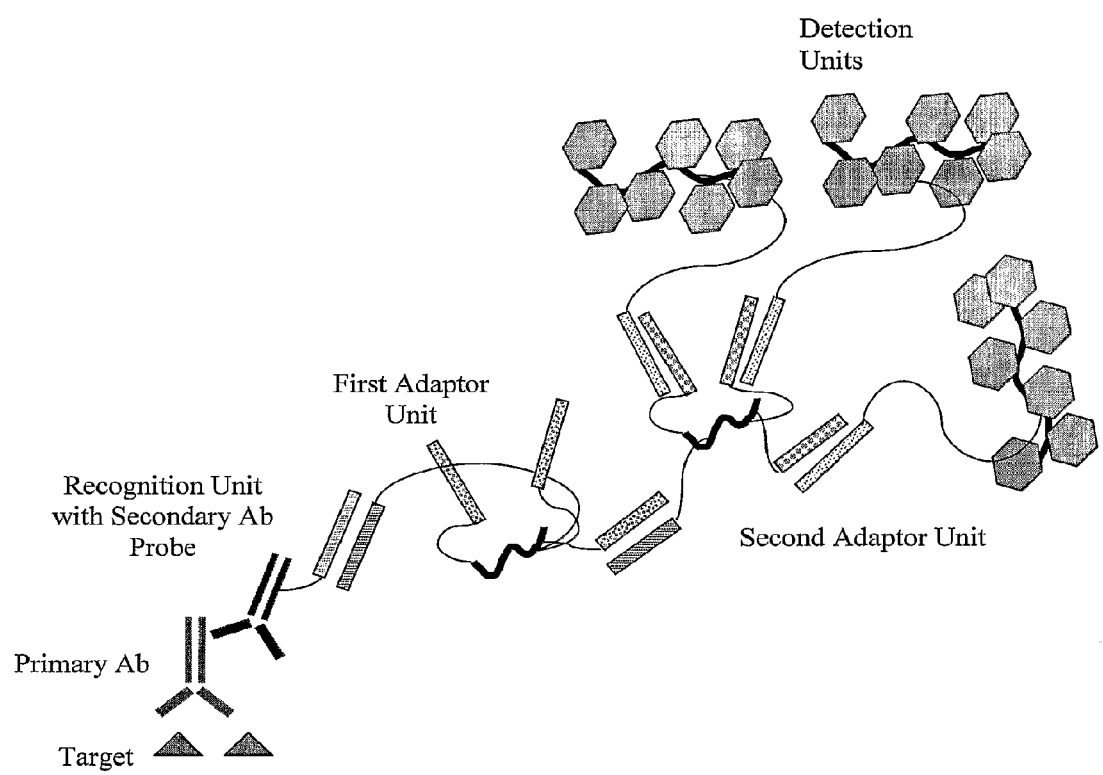
FIG. 9 shows an exemplary multiple-layer system according to the invention comprising two adaptor units, each with multiple nucleic acid analog segments.
Figure 10:
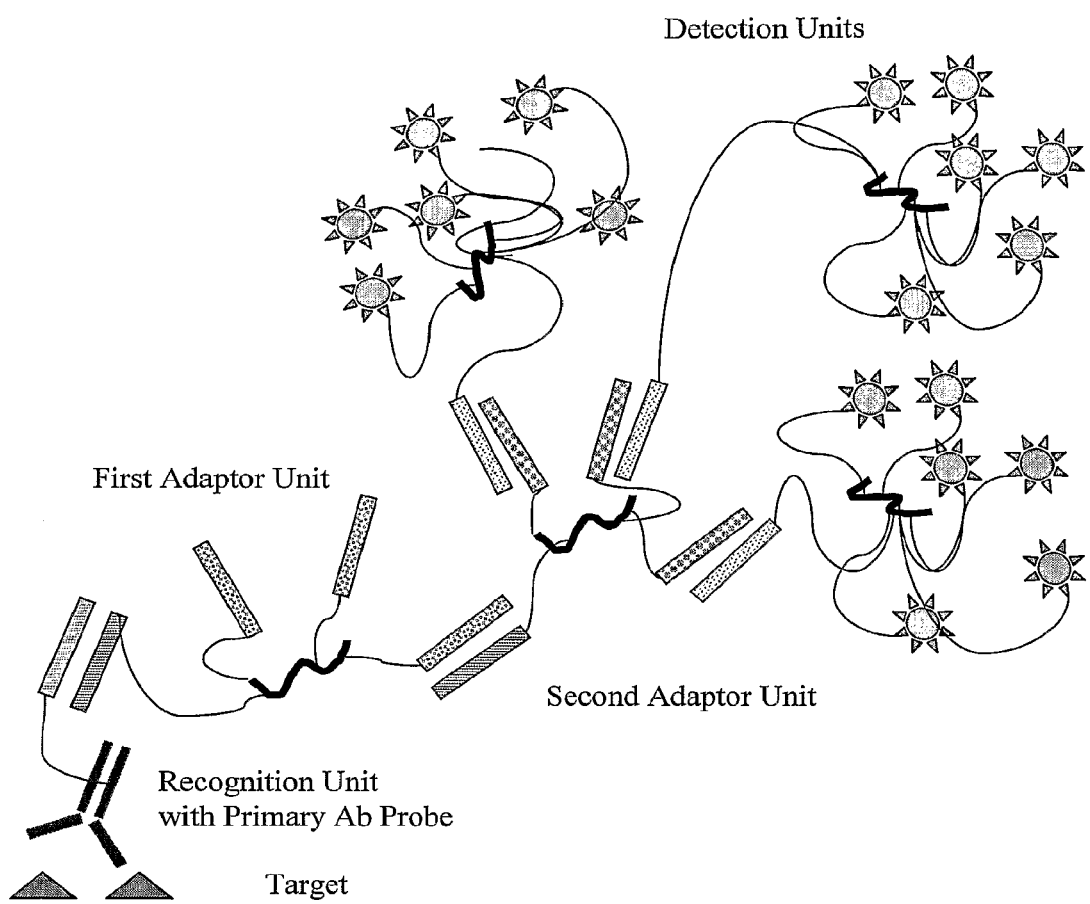
FIG. 10 also shows an exemplary multiple-layer system according to the invention comprising two adaptor units, each with multiple nucleic acid analog segments.
Figure 11:
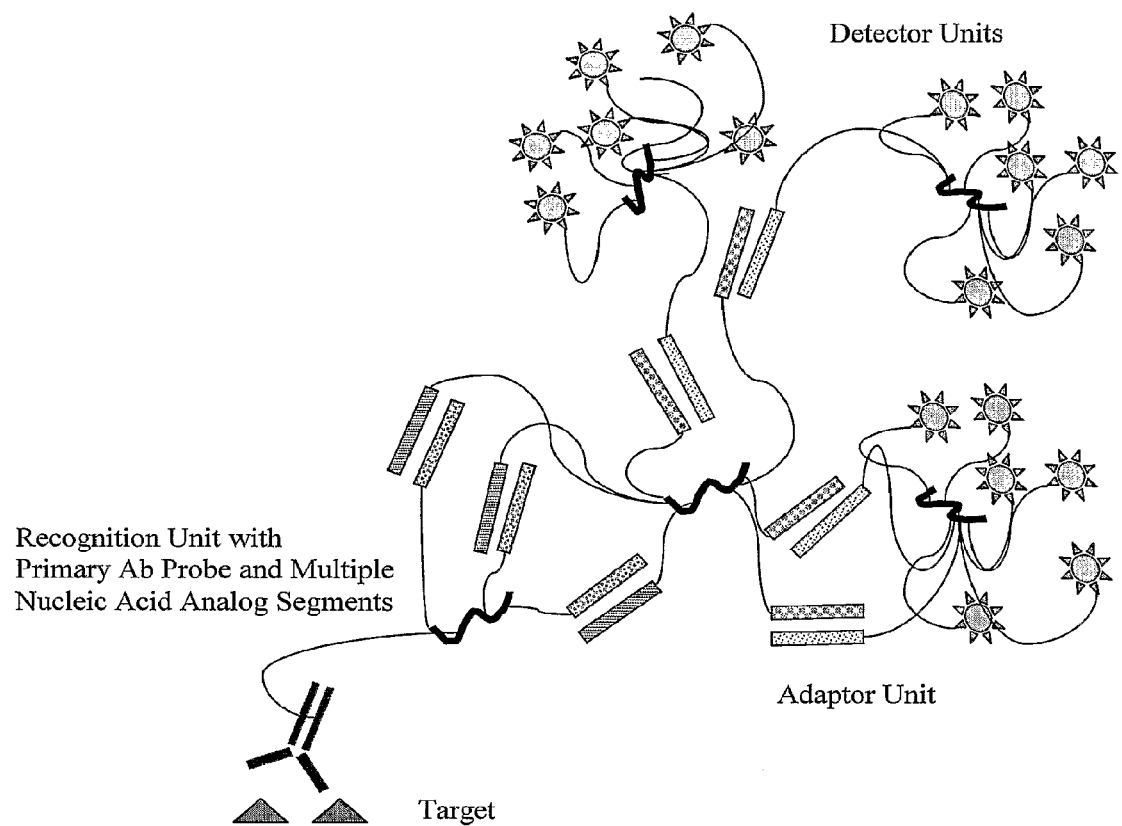
FIG. 11 demonstrates an embodiment according to the invention wherein the recognition unit comprises multiple nucleic acid analog segments, allowing the recognition unit to specifically hybridize to several adaptor units, which in turn, specifically hybridize to several detection units in order to enhance the signal from the target. (Compare FIG. 11 to FIG. 10, which shows an alternative embodiment generating a similar level of signal enhancement using two adaptor units rather than one.)
Figure 12:
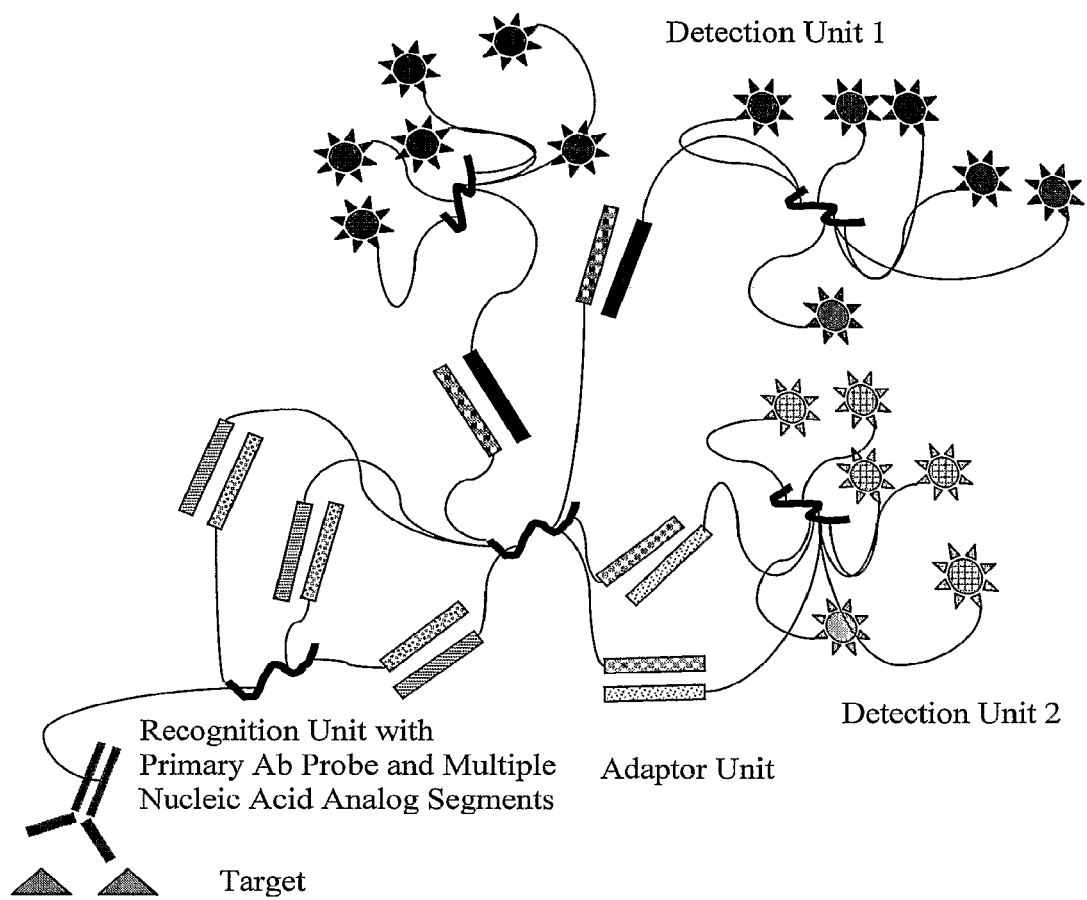
FIG. 12 shows an embodiment according to the invention comprising more than one detection unit, each comprising a different detectable label (differently-shaded flower shapes). In that system, the different nucleic acid analog segments of the adaptor unit specifically hybridize to each of the different detection units.
Figure 13:
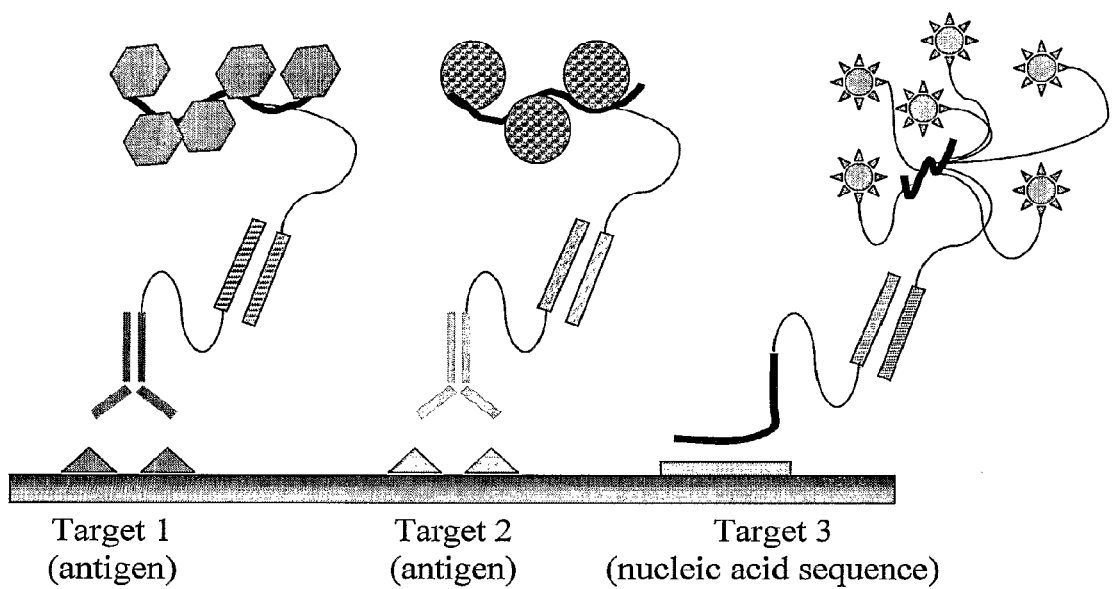
FIG. 13 illustrates an embodiment which may allow for visualization of more than one target in a sample, such as, here, two different proteins and a DNA segment. In this embodiment, three different two-layer systems, each comprising a recognition unit and a detection unit are employed together. Each detection unit carries a different detectable label such that the detectable labels are distinguishable from each other. Each set of recognition unit and detection unit does not cross-react with the other sets or with any other probes or targets in the sample.
Figure 14:
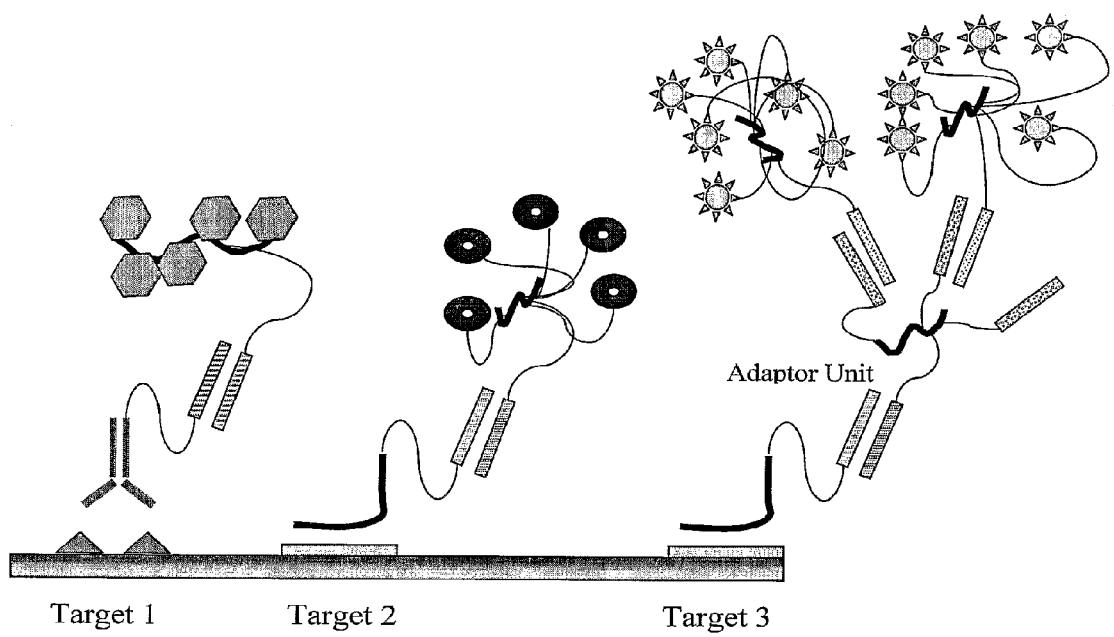
FIG. 14 shows another embodiment according to the invention which may recognize multiple targets in a sample. In this example, an adaptor unit is added to one set of recognition and detection units, for example, to enhance the signal from the third target. Such a system may be employed, for example, to adjust the signal intensity of the third target compared to the other targets in the sample.
Figure 15:
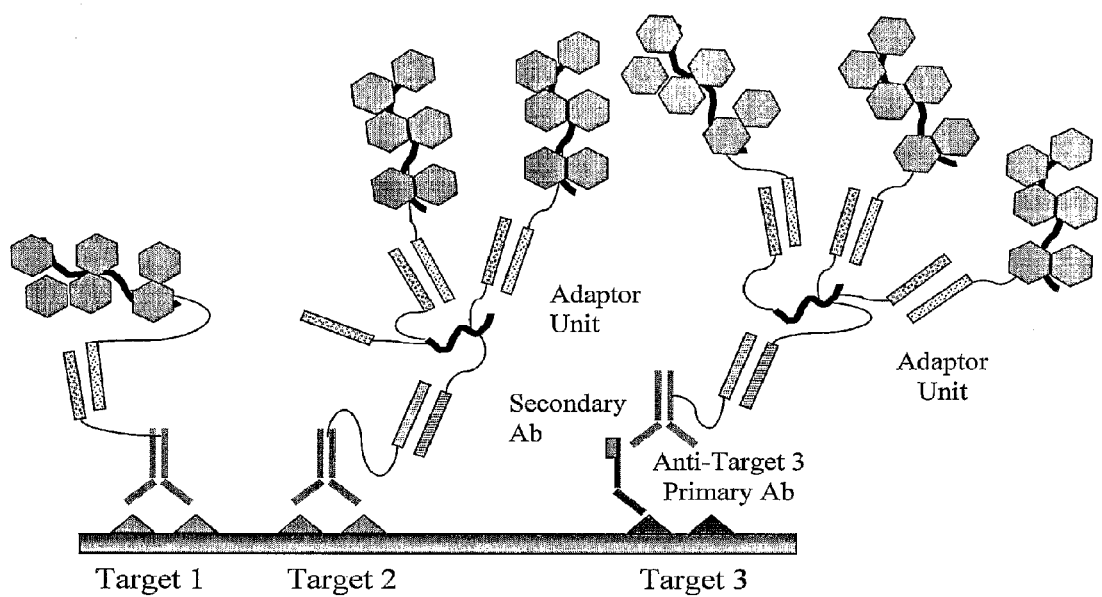
FIG. 15 illustrates an embodiment in which three different targets in a sample are labeled with the same detectable label, but with different recognition units and optional adaptor units.
Figure 16:
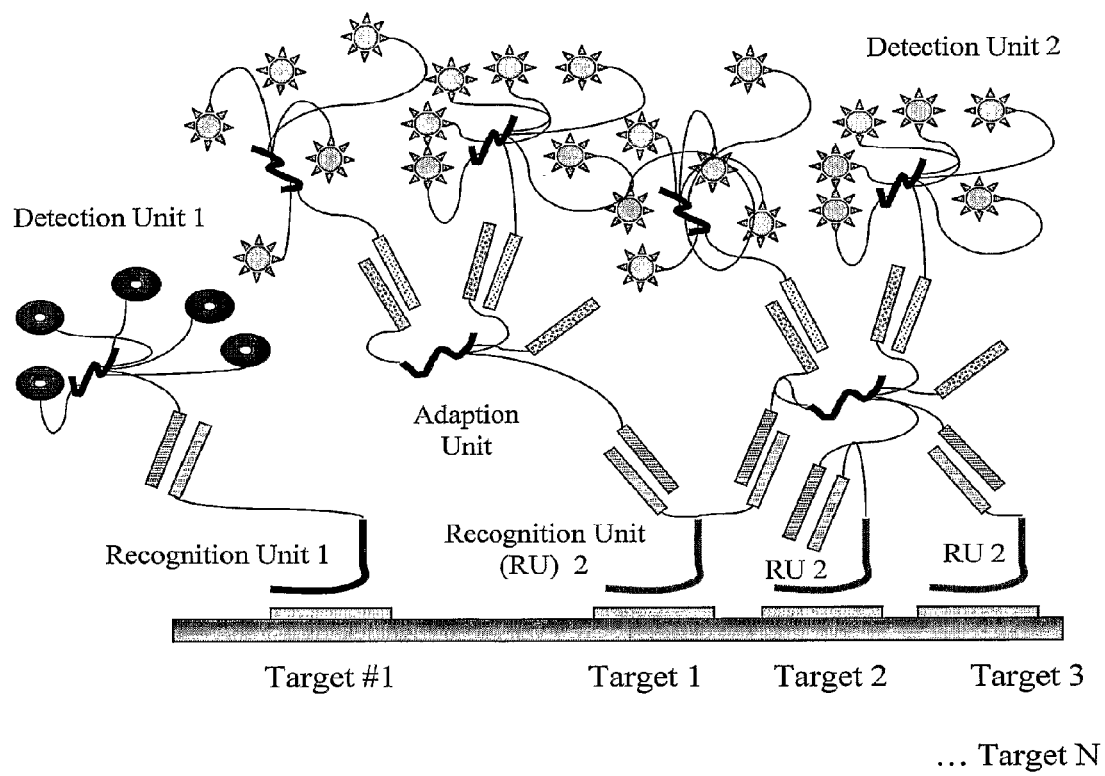
FIG. 16 shows an embodiment according to the invention in which several different nucleic acid targets are detected within the same sample. The two or three-layer systems shown allow for adjustments of the signal intensity from the detectable labels, for example, to compensate for differences in the natural intensity of each label.
Figure 17:
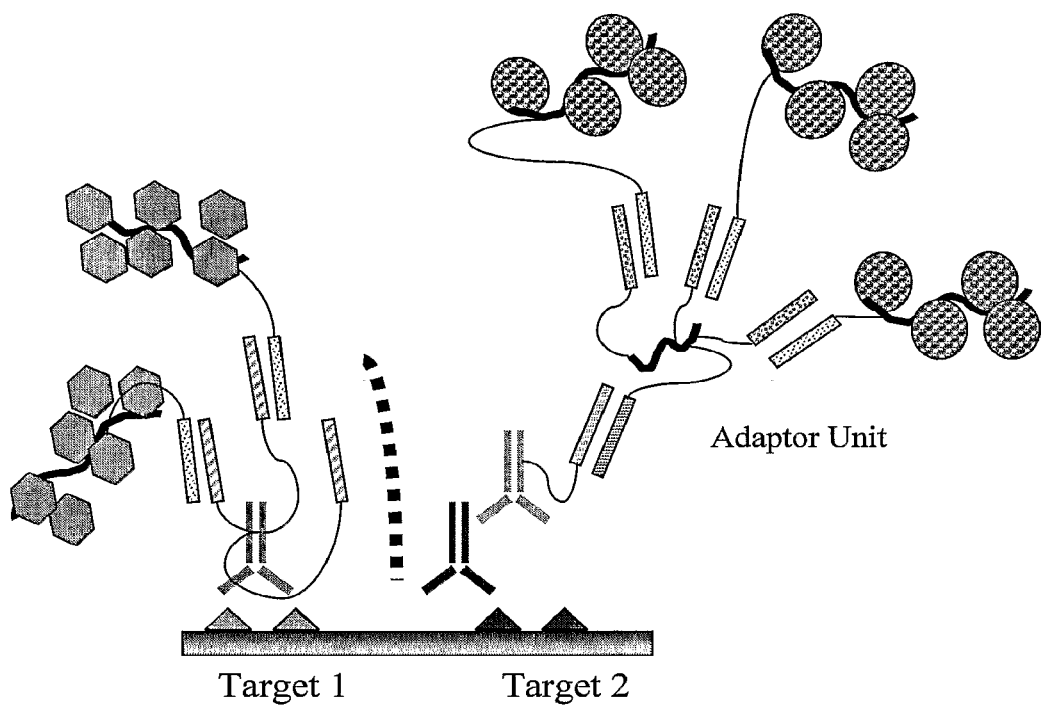
FIG. 17 illustrates an embodiment in which different targets within the same sample are detected using different detectable labels, in each case, using a different method to enhance the signal. For the first target, the recognition unit comprises multiple nucleic acid analog segments, while for the second target, the recognition unit comprises only one nucleic acid analog segment and an adaptor unit comprising multiple nucleic acid analog segments is used instead.

Multiple nucleic acid analog segments and adaptor units may increase the flexibility of the detection methods as a whole. For instance, by using an adaptor unit comprising multiple nucleic acid analog segments, one recognition unit may be able to link to several different detection units. Such a system may be useful, for example, to assess a target present in different samples, in which the samples have different compositions, or, for example, to switch from one type of detectable label to another depending on the sample conditions. For example, in FIG. 8b, an adaptor unit is shown comprising three different nucleic acid analog segments, which may be combined with different sets of detection units and recognition units. In other embodiments, such as shown in FIG. 8a, flexibility may be generated without the use of an adaptor unit, such as including multiple nucleic acid analog segments within the recognition unit, either close together as shown in FIG. 8a, or joined by different linkers, as shown in FIG. 8b. Yet further, multiple probes may also be used, such that a recognition unit binds to more than one type of target.

The thermodynamics and kinetics of the interactions of the different units may also be controlled through the number and sequence of the nucleic acid analog segments as well as through the concentrations of the different units. For instance, the binding strength between the different units may be increased using multiple nucleic acid analog segments. See, for example, FIGS. 10 and 11 in which the adaptor units include multiple nucleic acid analog segments of the same sequence, creating multiple attachments between the different units. See also FIG. 12, in which the second adaptor unit comprises multiple nucleic acid analog segments of two different sequences, allowing for binding to two different detection units, each detection unit linked to an adaptor unit by multiple attachments.

The invention may also be employed to detect more than one target in a sample. In certain embodiments, for example, different targets in the same sample may be detected with different sets of recognition and detection units and different detectable labels. See FIG. 13. For example, cross-reactivity may be avoided using different sets of base-paired nucleic acid analog segments within each of the sets of recognition and detection units. Because of the lack of cross-reactivity that the different specific hybridizations allow, the instant invention allows for methods in which all of the recognition units and detection units are added to the sample at the same time.

In other embodiments, at least one set of target-recognizing and detecting units may further include at least one adaptor unit. See FIG. 14. In some embodiments, the adaptor unit may serve to enhance the signal from one of the sets of recognition and detection units, for instance, to compensate for a weaker recognition by a probe, or for a lower amount of a target. Hence, the adaptor units according to the invention may be used in some assays to even out the intensities of the signals from different targets in the sample.

In yet other embodiments, a flexible system may be generated in which the same set of reagents may be used to detect more than one type of target. For example, in FIG. 15, three different targets are detected using the same detection unit and adaptor unit, but different recognition units. In another example shown in FIG. 16, many different targets in the same sample, such as nucleic acid segments, may be detected using the same detection unit and adaptor unit, but different recognition units each carrying a different probe. Such a system may be useful in detecting targets in an array-type sample, for instance. In preferable embodiments the method comprises steps of adding a mixture of primary binding agents or compositions comprising a mixture of primary binding agents and steps of adding compositions comprising a mixture of detectable labels. In certain embodiments compositions comprising such mixtures may be designed for multi-purpose use, wherein not all binding agents binds to a target or another binding agent. Multi-purpose compositions may for example be useful in methods for analysis of different samples expressing only few of several targets.

In some embodiments of the invention, one or more probes or binding agents or external components present in a sample may be sterically hindered. For example, FIG. 17, left panel, illustrates that the ability of a primary antibody to bind to a target may be reduced by steric hindrance from a conjugated nucleic acid analog segment. Such engineered steric hindrance may reduce non-specific binding or cross-reactivity, thus increasing the sensitivity of a system.

Methods according to the invention may also be used for or in conjunction with methods of diagnosing at least one disease or condition.

Additional applications of the instant methods are described in other International Applications submitted herewith entitled "New Nucleic Acid Base Pairs" and "Monomeric and Polymeric Linkers Useful For Conjugating Biological Molecules and Other Substances," the entire disclosures of which are incorporated herein by reference.

2. Targets

The instant invention can be applied to a variety of targets. Any target which can be recognized by a suitable recognition unit and probe is compatible with the instant invention. In some embodiments, the recognition may be direct, while in other embodiments, the recognition may be indirect, via another binding agent, such as at least one primary, secondary, or higher order binding agent.

In some embodiments, the target comprises a protein, such as a glycoprotein or lipoprotein, phosphoprotein, methylated protein, or a protein fragment, a peptide, or a polypeptide. In other embodiments, the target comprises a nucleic acid segment. In yet other embodiments, the target comprises a nucleic acid analog segment.

In other embodiments, the target may comprise a lipid; a glyco-lipid; a sugar; a polysaccharide; a starch; a salt; an ion; or one of a variety of other organic and Inorganic substances; any of which may be free in solution or bound to another substance. The target may be expressed on the surface of the sample, e.g., such as on a membrane or interface. Alternatively, the target may be contained in the interior of the sample. In the case of a cell sample, for instance, an interior target may comprise a target located within the cell membrane, periplasmic space, cytoplasm, or nucleus, or within an intracellular compartment or organelle.

Targets may also include viral particles, or portions thereof, e.g., a nucleic acid segment or a protein. The viral particle may be a free viral particle, i.e., not associated with any other molecule, or it may be associated with any sample described above. In some embodiments, the target may be an antigen or an antibody.

3. Detection Systems

The instant invention is compatible with many known detection formats and their associated samples. For example, the invention may be used in connection with immunoassays, protein detection assays, or nucleic acid hybridization assays such as: immunohistochemistry (IHC), immunocytochemistry (ICC), in situ hybridization (ISH), flow cytometry, enzyme immuno-assays (EIA), enzyme linked immuno-assays (ELISA), blotting methods (e.g. Western, Southern, and Northern), labeling inside electrophoresis systems or on surfaces or arrays, and precipitation, among others. All of those detection assays are useful in research as well as in the detection and diagnosis of a variety of diseases and conditions, for example.

For example, IHC specifically provides a method of detecting targets in a sample or tissue specimen in situ (see Mokry 1996, ACTA MEDICA 39:129). The overall cellular integrity of the sample is maintained in IHC, thus allowing detection of both the presence and location of the targets of interest. Typically a sample is fixed with formalin, embedded in paraffin and cut into sections for staining and subsequent inspection by light microscopy. Current methods of IHC use either direct labeling or secondary antibody-based or hapten-based labeling. Examples of known IHC systems include, for example, EnVision™ (DakoCytomation), Powervision® (Immunovision, Springdale, Ariz.), the NBA™ kit (Zymed Laboratories Inc., South San Francisco, Calif.), HistoFine® (Nichirei Corp, Tokyo, Japan). The present invention may allow for enhancement of signal or increased flexibility in IHC detection platforms.

IHC, ISH and cytological techniques may be performed in a matrix of tissue, cell and proteins which may be partly cross-linked and very inhomogeneous in nature. Diffusion rates increase with increasing concentrations and increasing temperature, but decrease with molecular weight and molecular size. Therefore, the physical size of the components is of great importance. For instance, large molecules can be excluded from diffusing into parts of the sample whereas small sized components more easily may diffuse in and out of the different compartments of the sample. In some embodiments, the units of the invention may be designed to be of small size and, for example, smaller than an antibody or biotin-streptavidine complex, in order to improve target recognition and detection.

4. Samples

Many types of samples are compatible with the instant invention. Samples may comprise solid and liquid solutions, for example, containing targets in a buffer. Samples may also be derived from living matter taken from any living organism, e.g., an animal, such as mammals (e.g. humans), plants, fungi, archaea, or bacteria. Thus, samples may comprise eukaryotic cells, archaeal cells, or prokaryotic cells. Samples may comprise a cell sample, such as a cell smear or colony, or a tissue specimen derived from a living organism, such as a tissue sample from an organ. They may also comprise a biological fluid, such as an animal-derived fluid, e.g. mammalian plasma, serum, lymph, whole blood, spinal, amniotic, or other fluid. Samples may also comprise other naturally-obtained samples such as soil or water samples, and synthetically derived samples such as chemical or industrial products or solutions, food products, and buffers.

Tissue or cell samples according to the invention may be prepared by a variety of methods known to those of ordinary skill in the art, depending on the type of sample and the assay format. For instance, tissue or cell samples may be fresh or preserved, and may be, for example, in liquid solution, flash-frozen or lyophilized, smeared or dried, embedded, or fixed on slides or other supports. In some embodiments, samples may be prepared and stained using a free-floating technique. In this method a tissue section is brought into contact with different reagents and wash buffers in suspension or freely floating in appropriate containers, for example micro centrifuge tubes, before being mounted on slides for further treatment and examination.

In some embodiments, a tissue section may be mounted on a slide or other support after an incubation with immuno-specific reagents. The remains of the staining process are then conducted after mounting. For example, for microscopic inspection in IHC and ISH, samples may be comprised in a tissue section mounted on a suitable solid support. For the production of photomicrographs, sections comprising samples may be mounted on a glass slide or other planar support, to highlight by selective staining certain morphological indicators of disease states or detection of detectable targets.

In some IHC embodiments, a sample may be taken from an individual, fixed and exposed to, for example, antibodies which specifically bind to the detectable target of interest. Sample processing steps may include, for example, antigen retrieval, exposure to a primary antibody, washing, exposure to a secondary antibody (optionally coupled to a suitable detectable label), washing, and exposure to a tertiary antibody linked to a detectable label. Washing steps may be performed with any suitable buffer or solvent, e.g., phosphate-buffered saline, TRIS-buffered saline, distilled water. The wash buffer may optionally contain a detergent, e.g., TWEEN®20 or NP-40.

IHC samples may include, for instance: (a) preparations comprising un-fixed fresh tissues and/or cells or solution samples (b) fixed and embedded tissue specimens, such as archived material; and (c) frozen tissues or cells. In some embodiments, an IHC staining procedure may comprise steps such as: cutting and trimming tissue, fixation, dehydration, paraffin infiltration, cutting in thin sections, mounting onto glass slides, baking, deparaffination, rehydration, antigen retrieval, blocking steps, applying primary antibody, washing, applying secondary antibody—enzyme conjugate, washing, applying a tertiary antibody conjugated to a polymer and linked with an enzyme, applying a chromogen substrate, washing, counter staining, applying a cover slip and microscopic examination.

ISH samples, for instance, may be taken from an individual and fixed before being exposed to a nucleic acid or nucleic acid analog probe on a recognition unit. In some embodiments, the nucleic acid in the sample may first be denatured to expose the target binding sites. Various counter-stains or paints may further be used in order to locate nucleic acid molecules or chromosomes within an ISH sample.

5. Quantitation of Signals

In some embodiments, the approximate amount of a target in a sample is also determined. For instance, a control target within the sample may be assayed as well as an experimental target. In the case of a nucleic acid target, for example, a chromosomal paint or counter-stain may be used. For instance, if the target is a locus on a larger piece of nucleic acid such as a plasmid or chromosome, the intensity of a contrasting label for the plasmid or chromosome or a neutral locus thereon may be compared to the intensity of the target locus. The intensity of the label from the sample may also be compared to that of a known standard or control sample. Estimating the amount of a detectable target in a sample is helpful, for instance, in a variety of diagnostic tests, and the estimate may be used to plan a course of treatment for a suspected disease or condition. Several commercial densitometry software programs and related instruments are available to quantitate the intensity of a stained target in a sample, such as those available from Fuji Film, Applied Biosystems, and Molecular Dynamics.

6. Methods of Fixing Samples

In some embodiments of this invention, tissue or cell samples may be fixed or embedded. Fixatives may be needed, for example, to preserve cells and tissues in a reproducible and life-like manner. Fixatives may also stabilize cells and tissues, thereby protecting them from the rigors of processing and staining techniques. For example, samples comprising tissue blocks, sections, or smears may be immersed in a fixative fluid, or in the case of smears, dried.

Many methods of fixing and embedding tissue specimens are known, for example, alcohol fixation and formalin-fixation and subsequent paraffin embedding (FFPE). Any suitable fixing agent may be used. Examples include ethanol, acetic acid, picric acid, 2-propanol, 3,3'-diaminobenzidine tetrahydrochloride dihydrate, acetoin (mixture of monomer) and dimer, acrolein, crotonaldehyde (cis+trans), formaldehyde, glutaraldehyde, glyoxal, potassium dichromate, potassium permanganate, osmium tetroxide, paraformaldehyde, mercuric chloride, tolylene-2,4-diisocyanate, trichloroacetic acid, tungstic acid. Other examples include formalin (aqueous formaldehyde) and neutral buffered formalin, glutaraldehyde, carbodiimide, imidates, benzoequinone, osmic acid and osmium tetraoxide. Fresh biopsy specimens, cytological preparations (including touch preparations and blood smears), frozen sections, and tissues for IHC analysis may be fixed in organic solvents, including ethanol, acetic acid, methanol and/or acetone.

7. Increasing the Reactivity and Specificity of Detectable Targets

In some embodiments, it may be helpful to pre-treat the samples to increase the reactivity or accessibility of a detectable target and to reduce nonspecific interactions.

If the target is an antigen, for example, a process called "antigen retrieval" may be used (and which is also known in the art as target retrieval, epitope retrieval, target unmasking, or antigen unmasking). See, e.g., Shi et al., *J Histochem*

Cytochem, 45(3): 327 (1997). Antigen retrieval encompasses a variety of methods including enzymatic digestion with proteolytic enzymes, such as e.g. proteinase, pronase, pepsin, papain, trypsin or neuraminidase. Some embodiments may use heat, e.g. "heat-induced epitope retrieval" or HIER. Heating may involve a microwave irradiation, or a water bath, a steamer, a regular oven, an autoclave, or a pressure cooker in an appropriately pH stabilized buffer, usually containing EDTA, EGTA, Tris-HCl, citrate, urea, glycin-HCl or boric acid. One may add detergents to the HIER buffer to increase the epitope retrieval, or to the dilution media and/or rinsing buffers to lower non-specific binding. In some embodiments, combinations of different antigen retrieval methods may be used.

The antigen retrieval buffer may be aqueous, but may also contain other solvents, including solvents with a boiling point above that of water such as e.g glycerol. This allows for treatment of the tissue at more than 100° C. at normal pressure.

Additionally, in some embodiments, the signal-to-noise ratio may be increased by different physical methods, including application of vacuum, or ultrasound, or freezing and thawing tissue samples before or during incubation of the reagents.

In some embodiments, treatments may be performed to reduce nonspecific binding. For example, carrier proteins, carrier nucleic acid molecules, salts, or detergents may reduce or prevent non-specific binding. Non-specific binding sites may be blocked in some embodiments with inert proteins like, HSA, BSA, ovalbumin, with fetal calf serum or other sera, or with detergents like TWEEN02O, TRITON® X-100, Saponin, BRU®, or PLURONICS®. Alternatively, non-specific binding sites may be blocked with unlabeled competitors for the recognition event between the target and the probe. For example, in the case of a nucleic acid interaction, non-specific binding may be reduced by adding unlabeled competitor nucleic acids or nucleic acid analogs such as digested, total human DNA or salmon sperm DNA, or unlabeled versions of the binding agent. In addition, repetitive sequences may be blocked, for example, using nucleic acids or nucleic acid analogs that specifically recognize those sequences, or sequences derived from a total DNA preparation. Salt, buffer, and temperature conditions may also be modified so as to reduce non-specific binding.

Cross reactivity of different components of the detection methods may be avoided, for example, by using antibodies derived from different species. Furthermore, combinations of e.g. secondary antibodies against primary antibodies and haptens may also be used to avoid unwanted cross reactivity. Alternatively, unwanted cross-reactivity or non-specific binding may be reduced or eliminated by designing sterieally hindered recognition units, adaptor units, or detection units. For instance, a recognition unit may be designed such that the nucleic acid analog segments provide a certain degree of steric hindrance near the probe. In addition, one may remove endogenous biotin binding sites or endogenous enzyme activity (for example phosphatase, catalase or peroxidase) as a step in the staining procedure. Endogenous biotin and peroxidase activity may be removed by treatment with peroxides, while endogenous phosphatase activity may be removed by treatment with levamisole. Heating may destroy endogenous phosphatase and esterase activity.

E. Kits and Instruments

The invention also provides a kit comprising one or more compositions according to the invention. The kit may optionally comprise one or more binding agents, and suitable reagents for, for instance: antigen retrieval, sample dilution, reagent dilution, blocking of non-specific binding, blocking of endogenous enzyme activity, or blocking of repetitive sequences. The kit may optionally also comprise at least one container, instructions for use, and reference targets or samples.

Instruments may be used in various embodiments of the invention. Instruments, capable of performing steps of staining, are useful for carrying out both single as well as multi-staining procedures, and, in particular, useful for detection of multiple targets that frequently requires balancing of the signals emanating from the different detectable labels.

WORKING EXAMPLES

Example 1a

Preparation of Pyrimidinone-monomer

1. In dry equipment 4.6 g of solid Na in small pieces was added to 400 mL ethanol (99.9%), and was dissolved by stirring. Hydroxypyrimidine hydrochloride, 13.2 g, was added and the mixture refluxed for 10 minutes. Then 12.2 mL ethyl-bromoacetate (98%) was added and the mixture refluxed for 1>z hour. The reaction was followed using Thin Layer Chromatography (TLC). The ethanol was evaporated leaving a white compound, which was dissolved in a mixture of 80 mL of 1M NaCltrate (pH 4.5) and 40 mL of 2M NaOH. This solution was extracted four times with 100 mL Dichloromethane (DCM). The DCM phases were pooled and washed with 10 mL NaCltrate/NaOH—mixture. The washed DCM phases were evaporated under reduced pressure and resulted in 17.2 g of crude solid product. This crude solid product was recrystallized with ethylacetate giving a yellow powder. The yield for this step was 11.45 g (63%).

2. The yellow powder, 12.45 g. from above was hydrolyzed by refluxing overnight in a mixture of 36 mL DIPEA, 72 mL water and 72 mL dioxane. The solvent was evaporated and water was removed from the residue by evaporation from toluene. The yield for this step was 100%.

3. OBS. Pyrimidinone acetic acid (10.5 g), 16.8 g PNA-backbone ethylester, 12.3 g DHBT-OH, 19 mL Triethylamine was dissolved in 50 mL N,N-dimethylformamide (DMF). DIPIDIC (11.8 mL) was added and the mixture stirred overnight at room temperature. The product was taken up in 100 mL DCM and extracted three times with 100 mL of dilute aqueous NaHCC>3. The organic phase was extracted twice with a mixture of 80 mL of 1M NaCltrate and 20 mL of 4M HCl. Because TLC showed that some material was in the citrate phase, it was extracted twice with DCM. The organic phases were pooled and evaporated. Because there was a precipitation of urea, the product was dissolved in a DCM, and the urea filtered off. Subsequent evaporation left an orange oil. Purification of the orange oil was performed on a silica column with 10% methanol in DCM. The fractions were collected and evaporated giving a yellow foam. The yield for this step was 7.0 g (26.8%).

4. The yellow foam (8.0 g) was hydrolyzed by reflux overnight in 11 mL DIPEA, 22 mL water, and 22 mL dioxane. The solvent was evaporated and the oil was dehydrated by evaporation from toluene leaving an orange foam. The yield for this step was 100%.

Example 1b

Second Method of Preparing Pyrimidonone Monomer

Step 1. In dry equipment 9.2 g of solid Na in small pieces was dissolved in 400 mL ethanol (99.9%), with stirring.

Hydroxypyrimidine hydrochlorid, 26.5 g, was added, and the mixture was stirred for 10 minutes at 50° C. Then 24.4 mL Ethyl bromoacetate (98%) was added and the mixture stirred at 50° C. for 1 hour. The reaction was followed using Thin Layer Chromatography (TLC).

The ethanol was evaporated leaving a white compound, which was dissolved in 70 mL of water and extracted with 20 mL DCM. Another 30 mL of water was added to the water phase, which was extracted with 3×100 mL DCM. The DCM-phase from the first extraction contains a lot of product, but also some impurities, wherefore this phase was extracted twice with water. These two water phases then were back extracted with DCM.

The combined DCM phases were pooled and washed with 10 mL water. The washed DCM phases were evaporation under reduced pressure and resulted in 25.1 g yellow powder. The yield for this step was 25.1 g=69%. Maldi-T of: 181.7 (calc. 182).

Step 2. 34.86 g yellow powder from above was dissolved in 144 mL 2M NaOH. After stirring 10 minutes at room temperature, the mixture was cooled in an ice bath. Now 72 mL 4 M HCl (cold) was added. The product precipitated. After stirring for 5 minutes, the precipitate was filtered and thoroughly washed with ice water. Drying in a dessicator under reduced pressure left 18.98 g yellow powder. The yield for this step was 18.98 g=64%.

Step 3. Pyrimidinone acetic acid 11.1 g and triethylamine 12.5 mL were dissolved in N,N-dimethylformamide (DMF) 24 ml, HBTU 26.2 g was added plus 6 mL extra DMF. After 2 minutes a solution of PNA-Backbone ethylester 14.7 g dissolved in 15 mL DMF was added. The reaction mixture was stirred at room temperature and followed using TLC. After V/z hour precipitate had formed. This was filtered off.

The product was taken up in 100 mL DCM and extracted with 2×100 mL dilute aqueous NaHC03. Both of the aqueous phases were washed with a little DCM. The organic phases were pooled and evaporated. Evaporation left an orange oil. Purification of the product was done on a silica column with 10-20% methanol in ethylacetate. The fractions were collected and evaporated giving a yellow oil. The oil was dissolved and evaporated twice from ethanol. The yield from this step was 20.68 g=90%.

Step 4. The yellow oil (18.75 g) was dissolved in 368 mL 0.2 M Ba(OH)$_2$. Stirring for 10 minutes before 333 mL 0.221 M H2S04 was added. A precipitation was performed immediately. Filtration through cellite, which was washed with water. The solvent was evaporated. Before the evaporation was at end, the product was centrifuged to get rid of the very rest of the precipitation. Reevaporation of the solvent left a yellow oil. The yield from this step was 13.56 g=78%.

Step 5. To make a test on the P-monomer 3 consecutive P's were coupled to Boc-L300-Lys(Fmoc)-resin, following normal PNA standard procedure. The product was cleaved from the resin and precipitated also following standard procedures: HPPP-L300-Lys(Fmoc). Maldi-T of on the crude product: 6000 (calc. 6000) showing only minor impurities.

Example 2

Preparation of the Thio-guanine Monomer 1. 6-Chloroguanine (4.93 g) and 10.05 g K2CO3 was stirred with 40 mL DMF for 10 minutes at room temperature. The reaction mixture was placed in a water bath at room temperature and 3.55 mL ethyl bromoacetate was added. The mixture was stirred in a water bath until TLC (20% MethanoVDCM) showed that the reaction was finished. The precipitated carbonate was filtered off and washed twice with 10 mL DMF. The solution, which was a little cloudy, was added to 300 ml water, whereby it became clear. On an ice bath the target compound slowly precipitated. After filtration the crystals were washed with cold ethanol and dried in a desiccator. The yield for this step was 3.3 g (44.3%) of ethyl chloroguanine acetate.

2. Ethyl chloroguanine acetate (3.3 g) was dissolved by reflux in 50 mL absolute ethanol. Thiourea (1.08 g) was added. After a refluxing for a short time, precipitate slowly began forming. According to TLC (20% Methanol/DCM) the reaction was finished in 45 minutes. Upon completion, the mixture was cooled on an ice bath. The precipitate was then filtered and dried overnight in a desiccator. The yield for this step was 2.0 g (60%) ethyl thioguanine acetate.

3. Ethyl thioguanine acetate (3.57 g) was dissolved in 42 mL DMF. Benzylbromide (2.46 mL) was then added and the mixture stirred in an oil bath at 45° C. The reaction was followed using TLC (25% MethanoVl/DCM). After 3 hours all basis material was consumed. The step 3 target compound precipitated upon evaporation under reduced pressure and high temperature. The precipitate was recrystallized in absolute ethanol, filtered and then dried in a desiccator. The yield for this step was 3.88 g (82%) of methyl benzyl thioguanine ethylester.

4. Methyl benzyl thioguanine ethylester (5.68 g) was dissolved in 12.4 mL of 2M NaOH and 40 mL THF, and then stirred for 10 minutes. The THF was evaporated by. This was repeated. The material was dissolved in water and then 6.2 mL of 4M HCl was added, whereby the target product precipitated. Filtering and drying in a desiccator. The yield for this step was 4.02 g (77%).

5. The product of step 4 (4.02 g), 3.45 g backboneethylester, 9 mL DMF, 3 mL pyridine, 2.1 mL triethylamine and 7.28 g PyBop were mixed and then stirred at room temperature. After 90 minutes a solid precipitation formed. The product was taken up in 125 mL DCM and 25 mL methanol. This solution was then extracted, first with a mixture of 80 mL of 1M NaCltrate and 20 mL of 4M HCl, and then with 100 mL dilute aqueous NaHC03. Evaporation of the organic phase gave a solid material. The material was dissolved in 175 mL boiling ethanol. The volume of the solution was reduced to about 100 mL by boiling. Upon cooling in an ice bath, the target product precipitate. The crystals were filtered, washed with cold ethanol and then dried in a desiccator. The yield of this step was 6.0 g (86%.)

6. The product of step 5 (6.0 g) was dissolved in 80 mL THF, 7.5 mL 2M NaOH and 25 mL water. The solution became clear after ten minutes of stirring. THF was evaporated. Water (50 mL) was added to the mixture. THF was evaporated. Water (50 mL) was added to the mixture. When the pH was adjusted by the addition of 3.75 mL of 4M HCl, thio-guanine monomer precipitated. It was then filtered, washed with water and dried in a desiccator. The yield for this step was 5.15 g (91%).

Example 3

Preparation of Diaminopurine Acetic Acid Ethyl Ester

1. Diaminopurine (10 g) and 40 g of K$_2$CO$_3$ were added to 85 mL of DMF and stirred for 30 minutes. The mixture was cooled in a water bath to 15° C. Ethyl bromoacetate (3 mL) was added three times with 20 minute intervals between each addition. This mixture was then stirred for 20 minutes at 15° C. The mixture was left in the water bath for another 75 minutes, and the temperature increased to 18° C. The DMF was removed by filtering and the remaining $K_2CO_3$ was added to 100 mL of ethanol and refluxed for 5 minutes. Filtering and repeated reflux of the $K_2CO_3$ in 50 mL ethanol, filtering. The pooled ethanol phases were placed in a freezer, after which crystals formed. These crystals were filtered, washed with cold ethanol, filtered again and then dried in a desiccator overnight. The yield for this step was 12 g (76%).

Example 4

Preparation of $L_{30}$-Linker

A solution of 146 mL of 2,2'-(Ethylenedioxy)bis(ethylamine) (98%) in 360 mL of THF was cooled in an ice bath. Di-tert-butyl dicarbonate (97%) (65 g) in 260 mL THF was added dropwise over one hour. The solvent was evaporated. The remaining oil was dissolved in water and then evaporated off. The oily product was dissolved in 300 mL water, extracted with 300 mL DCM, then washed twice with 150 mL of DCM. The collected organic phase was washed with 50 mL of water before evaporating to about half the volume. The organic phase was then extracted with 400 mL of 1M NaCltrate (pH 4.5), and then extracted again with 50 mL of 1M NaCltrate (pH 4.5). The aqueous phases were washed with 50 mL DCM before cooling on an ice bath. While stirring, 100 mL of 10M NaOH was added to the aqueous washed aqueous phases resulting in pH of 13-14. In a separation funnel the product separated on its own. It was shaken with 300 mL DCM and 50 ml water. The organic phase was evaporated, yielding a white oil. The yield for this step was 48.9 g (65.7%). The product had a predicted molecular formula of $C_{11}H_{24}N_2O_4$ (MW 248.3).

2. Boc-amine (76.2 g) was dissolved in 155 mL pyridine. Diglycolic anhydride (54.0 g) (90%) was added. After stirring for 15 minutes the intermediate product separated out and then 117 mL Acetic Anhydride (min. 98%) was added and the mixture stirred at 95° C. for 1 hour. The solution was then put under reduced pressure and evaporated. Water (117 mL) was added, and the mixture was then stirred for 15 minutes, after which 272 mL of water and 193 mL of DCM were added. The organic layer was extracted twice with 193 mL of 1M [\Ia2CO_3 and then twice with a mixture of 72 mL of 4M HCl and 289 mL of 1M NaCltrate. After each extraction the aqueous phase was washed with a little DCM. The collected organic phase was washed with 150 mL of water. The solvent was evaporated leaving the product as an orange oil. This yield for this step was 100.3 g (0.29 mol) (94%). The product had a predicted molecular formula of $C_{15}H26N_2O_7$ (MW 346.4).

3. The product from step 2 (100.3 g) was dissolved in an equal amount of THF and was then added dropwise to 169.4 mL of 2,2'-(Ethylendioxy)bis(ethylamine) at 60° C. over the period of 1 hour. The amine was distilled from the reaction mixture at 75-80° C. and a pressure of 3×10"[1] mBar. The residue from the distillation was taken up in a mixture of 88 mL of 4M HCl and 350 mL of 1M NaCltrate and then extracted three times with 175 mL of DCM. The aqueous phase was cooled in an ice bath and was cautiously added to 105 mL of 10M NaOH while stirring. In a separation funnel the product slowly separated from the solution. When separated 100 mL of water and 950 mL of DCM were added to the product. Stirring for some minutes before pouring to a separation funnel. The pH in the aqueous phase should be 14. The aqueous phase was extracted four times with 150 mL of DCM. The solvent was evaporated. The oily residue was dehydrated by evaporation from toluene, giving a yellow oil. The yield for this step was 115.48 g (81%). The product had a predicted molecular formula of $C_{21}H_{42}N_4O_9$ (MW 494.6).

4. The Boc-amine (115.48 g) from step 3 was dissolved in 115 mL of pyridine. Diglycolic anhydride (40.6 g) (90%) was added and the mixture stirred for 15 minutes, after which the intermediate product came out. Acetic Anhydride (97 mL) (min. 98%) was added and the mixture stirred at 95° C. for 1 hour. The mixture was then evaporated under reduced pressure. The mixture was then cooled and then 80 mL of water was added. This mixture was stirred for 15 minutes and then 200 mL of water and 150 mL of DCM were added. The organic layer was extracted twice with 150 mL of 1M $Na_2CO_3$ and then twice with a mixture of 53 mL of 4M HCl and 213 mL of 1M NaCltrate. After each extraction the aqueous phase was washed with a little DCM. The collected organic phase was washed with 150 mL of water. The solvent was evaporated. The oily residue was dehydrated by evaporation from toluene, giving a yellow oil. The yield for this step was 125 g (92%). The product had a predicted molecular formula of $C_{25}H_{44}N_4O_{12}$ (MW 592.6), with a mass spectrometry determined molecular weight of 492.5.

Further purifying of the product could be done on a silica column with a gradient from 5-10% methanol in DCM. The yield from the column purification was 69% and produced a white oil.

5. White oil (12.4 g) from step 4 was dissolved in a mixture of 12 mL water and 12 mL 1,4-Dioxane (99%) and was then heated to reflux. DIPEA (6 mL) was added and refluxed for 30 minutes. This mixture was cooled and then evaporated. The oily residue was dehydrated by evaporation from toluene, giving a yellow oil. The product had a predicted molecular formula of $C_{25}H_{46}N4O_{14}$ (MW 610.6).

Example 5

Exemplary Embodiments of PNA Sequences

All are made by PNA standard procedures (see Examples 17 and 18). Table 1.

TABLE 1

| SEQUENCE DESIGNATION | PNA SEQUENCES[1] | N-TERMINAL | C-TERMINAL | MOLECULAR WEIGHT |
|---|---|---|---|---|
| SEQ. AA | TCD-DG$_S$G$_S$-TAC-A | FLU-$_{L30}$- | -LYS(CYS) | 8805 |
| SEQ. AB | U$_S$GU$_S$-DPP-TTG-D | FLU-$_{L30}$- | -LYS(CYS) | 8727 |
| SEQ. AC | CU$_S$G$_S$-G$_S$DD-TU$_S$D-G$_S$DC | FLU-$_{L30}$- | -LYS(CYS) | 9413 |
| SEQ. AD | GTP-TAA-TTP-PAG | FLU-$_{L30}$- | -LYS(CYS) | 9203 |
| SEQ. AE | DG$_S$T-CG$_S$D-DG$_S$G-U$_S$CU$_S$ | FLU-$_{L30}$- | -LYS(CYS) | 9413 |
| SEQ. AF | AGA-CPT-TPG-APT | FLU-$_{L30}$- | -LYS(CYS) | 9187 |
| SEQ. AG | TCD-DI I-TAC-A | FLU-$_{L30}$- | -LYS(CYS) | 8742 |

[1]Flu is fluorescein; T is thiamine; C is cytosine; D is diaminopurine; G$_S$ is thioguanine; A is Adenine; U$_S$ is 2/4-thiouraeil; G is guanine; P is pyrimidone; I is inosine.

Example 6

Three PNAs with the $L_{30}$ Linker with Different Amino Acids at the C-terminal BA: Flu-L$_{30}$-DGT-DTC-GTD-CCG-Lys(Acetyl)

BB: Flu-L$_{30}$-DGT-DTC-GTD-CCG-Lys(Cys)

BC: Flu-L$_{30}$-DGT-DTC-GTD-eCG-Lys(Lys)$_3$

Example 7

Synthesis of Flu-L$_{90}$-Lys(Flu)-L$_{30}$-Lys(Cys)

Using procedure provided in Example 18a, an MBHA-resin was loaded with Boc-Lys(Dde)-OH. Using a peptide synthesizer, amino acids were coupled according to PNA solid phase procedure provided in Example 18d yielding Boc-Lgo-Lys(Fmoc)-L$_3$o-Lys(Dde). The Boc and Fmoc protections groups were removed and the amino groups marked with flourescein using the procedure in Example 18e. Then, the Dde protection group was removed and 0.4 M cysteine was added according to the procedure in Example 18b. The PNA was cleaved from the resin, precipitated with ether and purified on HPLC according to Example 18d. The product was found to have a molecular weight of 3062 using MALDI-TOF mass spectrometry; the calculated molecular weight is 3061.

Example 8

Synthesis of a Conjugate Made from Sequence AA from Example 5, DexVS70, and Flu(10)

Dextran (with a molecular weight of 70 kDa) was activated with divinylsulfone to a degree of 92 reactive groups/dextran polymer; this product is designated DexVS70.

| | |
|---|---|
| 280 µL DexVS70 | 20 nmol |
| 66 µL Flu$_2$Cys | 160 nmol (prepared from Example 7) |
| 25 µL 0.8M NaHCOa pH = 9.5 | |
| 29 µL H$_2$O | |

The above four compounds were mixed. The mixture was placed in a water bath at 30° C. for 16 hours. The mixture was added to 50 nmol of freeze-dried PNA (sequence AA from Example 5). The mixture was placed in a water bath at 30° C. for 30 minutes. The conjugating reaction was quenched with 50 µL of 500 mM cysteine for 30 minutes at 30° C. Purification of the product was performed using FPLC: column SUPERDEX®-200, buffer 10 mM Hepes 100 mM NaCl, method 7 bank 2, Loop 1 mL. Two fractions were collected: one with the product and one with the residue. The relative absorbance Flu$_2$ ($\epsilon_{500nm}$=146000 M$^{-1}$ $\epsilon_{260nm}$=43350 M$^{-1}$) and PNA ($\epsilon_{500nm}$=73000 M$^{-1}$, $\epsilon_{260nm}$=104000 M$^{-1}$) was used to calculate the average conjugation ratio of Flu$_2$, PNA, and DexVS70. The conjugation ratio of Flu$_2$ to DexVS70 was 9.4. The conjugation ratio of PNA (sequence AA) to DexVS70 was 1.2.

Example 9

Synthesis of HRP-DexVS70-Seq. AA

Using the procedure of Example 14, the conjugate HRP-DexVS70-Seq. AA was made. The ratio of HRP to DexVS70 is 12.2; the ratio of Seq. AA to Dex70 is 1.2.

The synthesis of GaM-DexVS70-Seq. AB was performed using the procedure in Example 16 with the following changes as indicated.

Example 10

Synthesis of GaM-DexVS70-Seq. AB

Dextran (molecular weight 70 kDa) is activated with divinylsulfone to a degree of 92 reactive groups/dextran polymer.

| | |
|---|---|
| 105.0 µL DexVS70 | 7.5 nmol |
| 57.0 µL Goat anti mouse Imuno globuline (GAM-Ig) | 15 nmol |
| 8.9 µL M NaCl | |
| 10.6 µL 0.8M NaHC03 (pH = 9.5) | |
| 144.5 µH$_2$O | |

The above five components were mixed and placed in a water bath at 30° C. for 40 minutes. Two hundred and ninety µL were taken out of the mixture and added to 100 nmol of Seq. AB, which was previously dissolved in 80 µL of H$_2$O. Then, 20 µL of 0.8 M NaHCO$_3$ (pH 9.5) was added and the mixture placed in a water bath at 30° C. for 1 hour. Quenching was performed by adding 39 µL of 500 mM cysteine and letting the resultant mixture set for 30 minutes at 30° C.

Purification of the product on FPLC: column SUPERDEX®-200, buffer 10 mM Hepes 100 mM NaCl, method 7 bank 2, Loop 1 mL. Two fractions were collected: one with the product and one with the residue. Relative absorbance PNA(Flu) ($\epsilon_{500nm}$=73000 M$^{-1}$) and GAM ($\epsilon_{278nm}$=213000 M$^{-1}$) (correction factor for PNA at 278 nm is due to the specific PNA and is calculated: 278/500 nm) was used to calculate the average conjugation ratio of PNA, GAM and DexVS70. The ratio of PNA to DexVS70 was 5.3 and the ratio of GaM to DexVS70 was 0.8.

Example 11

Exemplary Embodiments of PNA1-DexVS<<PNA2 Conjugates

TABLE 2

| Conjugate designation | ratio | PNA1 | PNA1 nmol | PNA1 to DexVS | PNA2 | PNA2 nmol | PNA2 to DexVS | DexVS |
|---|---|---|---|---|---|---|---|---|
| Conj. CA | 1:9 | Seq. AA | 12.5 | 1.02 | Seq. AD | 100 | 8.2 | DexVS70 |
| Conj. CB | 1:6 | Seq. AC | 40 | 1.5 | Seq. AB | 200 | 7.4 | DexVS70 |
| Conj. CC | 1:16 | Seq. AC | 13.3 | 0.84 | Seq. AB | 200 | 12.7 | DexVS150 |

TABLE 2-continued

| Conjugate designation | ratio | PNA1 | PNA1 nmol | PNA1 to DexVS | PNA2 | PNA2 nmol | PNA2 to DexVS | DexVS |
|---|---|---|---|---|---|---|---|---|
| Conj. CD | 1.6 | Seq. AC | 40 | 2.3 | Seq. AB | 200 | 11.5 | DexVS150 |

All conjugates were made by standard conjugation procedures of Example 17.

Example 12

Synthesis of Anti-human-BCL2-DexVS70-PNA

Dextran (molecular weight 70 kDa) was activated with divinylsulphone to a degree of 92 reactive groups/dextran polymer, and is designated DexVS70. The antibody Anti-Human-BCL2 is designated AHB.

| | |
|---|---|
| 105 μL DexVS70 | 7.5 nmol |
| 800 μL AHB conc. (2.9 g/L) | 15.1 nmol |
| 25 μL 4M NaCl | |
| 32 μL 0.8M NaHCO$_3$ (pH = 9.5) | |

The above four compounds were mixed and placed in a water bath at 30° C. for 65 minutes. From this mixture, 875 μL was taken out and added to the indicated number of nmol of PNA in the table below; before the addition the PNA had been dissolved in the μL of H$_2$O indicated in the table below. Then the number of μLs of 0.8 M NaHCO$_3$-(pH 9.5) was added according to the table below. The resulting mixture was placed in a water bath at 30° C. for 70 minutes. Quenching was performed by adding 6 mg of solid cysteine (0.05 M) to the mixture and letting it stand for 30 minutes at 30° C.

Purification of the product on FPLC: column SUPERDEX®-200, buffer 10 mM Hepes 100 mM NaCl, method 7 bank 2, Loop 1 mL. Two fractions were collected: one with the product and one with the residue. Relative absorbance PNA(Flu) ($\epsilon_{500nm}$=73000 M$^{-1}$) and AHB ($\epsilon_{278nm}$=213000 M$^{-1}$) (correction factor for PNA at 278 nm is due to the specific PNA and is calculated: 278/500 nm) was used to calculate the average conjugation ratio of PNA, AHB and DexVS70.

Conjugates with different ratios PNA are shown in the following table.

TABLE 3

| Conjugate designation | nmol of PNA added | μL of H$_2$O added | μL of 0.8M NaHCO$_3$ (pH 9.5) added | PNA to DexVS70 | AHB to DexVS70 |
|---|---|---|---|---|---|
| Conj. DA | 100 | 75 | 25 | 9.5 | 1.6 |
| Conj. DB | 33 | 30 | 10 | 2.9 | 1.2 |
| Conj. DC | 67 | 60 | 20 | 5.6 | 1.1 |

Example 13

Solid Phase Synthesis and Purification of Lys(Flu)-L$_{30}$-chr 17:14-L$_{30}$-Lys(Flu)-L$_{90}$-Lys(Flu)-L$_{90}$-Lys(Flu)

All Standard procedures are described in Example 18.

1. An MBHA-resin was loaded with Boc-L$_{30}$-Lys(Fmoc)-L$_{90}$-Lys(Fmoc)-L$_{90}$-Lys(Fmoc) using a standard loading procedure to a loading of 0.084 mmovg.

2. To this resin, Boc-Lys(Fmoe)-L$_{30}$-AAC-GGG-ATA-ACT-GCA-CCT-was coupled using the peptide synthesizer machine following standard PNA solid phase chemistry. Fmoc protection groups were removed and the amino groups were labeled with fluorescein. After cleaving and precipitation the PNA was dissolved in TFA. The precipitate was washed with ether. The precipitate was dissolved in 200 μL NMP To this solution 6 mg Fmoc-Osu was added and dissolved. Next, DIPEA (9 μL) was added and the reaction was followed using MALDI-TOF mass spectrometry. After 30 minutes the reaction was finished and the PNA was precipitated and washed with ether.

HPLC after dissolving the PNA in 30% CH$_3$CN and 10% TFA/H$_2$O gave three pure fractions. The fractions were pooled and lyophilized. The lyophilized PNA was then dissolved in 192 μL NMP. Piperidine (4 μL) and 4 μL DBU was added to this solution which set for 30 minutes. Analysis by MALDI-TOF mass spectrometry gave a molecular weight of 10777.

The precipitate was washed with ether and was then dissolved in 100 μL TFA. The precipitate was washed with ether and then dried using N$_2$ gas.

Example 14

Standard Synthesis of HRP-DexVS70-PNA Conjugate

Dextran (molecular weight 70 kDa) is activated with divinylsulfone to a degree of 92 reactive groups/dextran polymer.

| | |
|---|---|
| 192 μL DexVS70 | 13.7 nmol |
| 255 μL horse radish peroxidase (HRP) | 602 nmol |
| 15 μL 4M NaCl | |
| 19 μL 0.8M NaHC0$_3$ pH = 9.5 | |
| 119 μL H$_2$O | |

The above five components are mixed together placed in a water bath at 30° C. for 16 hours. Five hundred microliters of this mixture are added to 50 nmol PNA, which is previously dissolved in 40 μL H$_2$O. Then, 10 μL of 0.8 M NaHCO$_3$ (pH 9.5) is added. The mixture is then placed in a water bath at 30° C. for 2 hours. Quenching is performed by adding 55 μL of 110 mM cysteine and letting the resultant mixture set for 30 minutes at 30° C.

Purification of the product is performed by FPLC: column SUPERDEX®-200, buffer 10 mM Hepes 100 mM NaCl, method 7 bank 2, Loop 1 mL.

Two fractions are collected: one with the product and one with the residue. Relative absorbance HRP ($\epsilon_{404nm}$=83000 M$^{-1}$, $\epsilon_{500nm}$=9630 M$^{-1}$) and PNA(Flu) ($\epsilon_{500nm}$=73000 M$^{-1}$) is used to calculate the average conjugation ratio of HRP, PNA and DexVS70.

Example 15

Standard Synthesis of GAM-DexVS70-PNA Conjugate

Dextran (molecular weight 70 kDa) is activated with divinylsulfone to a degree of 92 reactive groups/dextran polymer (DexVS70).

| | |
|---|---|
| 105.0 µL DexVS70 | 7.5 nmol |
| 57.0 µL Goat anti mouse Imuno globuline (GAM) | 15 nmol |
| 8.9 µL 4M NaCl | |
| 10.6 µL 0.8M NaHCOa (pH = 9.5) | |
| 144.5 µL H$_2$O | |

The above five components are mixed and placed in a water bath at 30° C. for 40 minutes. Two hundred and ninety µL is taken out of the mixture and added to 50 nmol of PNA, which is previously dissolved in 40 µL of H$_2$O. Then, 10 µL of 0.8 M NaHCO$_3$ (pH 9.5) is added and the mixture placed in a water bath at 30° C. for 1 hour. Quenching is performed by adding 34 µL of 500 mM cysteine and letting the resultant mixture set for 30 minutes at 30° C.

Purification of the product on FPLC: column SUPERDEX®-200, buffer 10 mM Hepes 100 mM NaCl, method 7 bank 2, Loop 1 mL. Two fractions are collected: one with the product and one with the residue. Relative absorbance PNA (Flu) ($\epsilon_{500nm}$=73000 M$^{-1}$) and GAM ($\epsilon_{278nm}$=213000 M$^{-1}$) (correction factor for PNA at 278 nm is due to the specific PNA and is calculated: 278/500 nm) was used to calculate the average conjugation ratio of PNA, GAM and DexVS70.

Example 16

Standard Synthesis of PNA1-DexVS70-PNA2

Dextran (molecular weight 70 kDa) is activated with divinylsulfone to a degree of 92 reactive groups/dextran polymer. PNA1 (100 nmol) is dissolved in 140 µL of DexVS70 (10 nmol). To this mixture 12.5 µL of PNA2 (12.5 nmol) dissolved in H$_2$O is added, and then 30 µL of NaHCO$_3$ (pH 9.5) is added and the solution mixed. The resultant mixture is placed in a water bath at 30° C. for 35 minutes. Quenching was performed by adding 18.3 µL of 500 mM cysteine in Hepes and letting this mixture set for 30 minutes at 30° C.

Purification of the product on FPLC: column SUPERDEX®-200, buffer 10 mM Hepes 100 mM NaCl, method 7 bank 2, Loop 1 mL. Two fractions are collected: one with the product and one with the residue. Relative absorbance PNA (Flu) ($\epsilon_{500nm}$=73000 M$^{-1}$) and the proportion between the two PNA's is used to calculate the average conjugation ratio of PNA, PNA and DexVS70.

Example 17

Synthesis of the Boc-PNA-I(O-Bz)-monomer

6-Benzyloxypurine. Sodiumhydride (60% Dispersion in mineral oil; 3.23 g; 80 mmol) was slowly added to benzyl alcohol (30 ml; 34.7 mmol). After the addition of more benzyl alcohol (10 ml) and 6-chloropurine (5.36 g). The reaction mixture was heated to 100° C. for 4 hours. When the reaction mixture has reached room temperature, water (1 ml) was slowly added. 6-Benzyloxypurine was precipitated by the addition of acetic acid (4.6 ml) and diethylether (550 ml). The precipitate was separated by filtration (11.72 g). Re-crystallization from ether gave (4.78 g; 65.4%). Melting point was 175-177° C. (litt. 170-172° C.)[Ramazaeva N., 1989 #473] 1H-NMR (DMSO-d6): 8.53 (1H, s); 8.39 (1H, s); 7.54-7.35 (5H, m); 5.62 (2H, s).

Methyl (6-(Benzyloxy)purin-9-yl)acetate. 6-Benzyloxypurine (4.18 g; 18.5 mmol) was added to a suspension of potassium carbonate (3.1 g; 22.4 mmol) in DMF (100 ml). After 15 min., bromoacetic acid methyl ester (1.93 ml; 20.4 mmol) was added. The reaction was monitored by TLC in butanokacetic acidiwater 4:1:1. Upon completion, the reaction mixture was partitioned between water (600 ml) and ethyl acetate (600 ml). The organic phase was dried over magnesium sulfate and evaporated to a volume of ~10 ml and precipitated with pet. ether. The two products were separated by column chromatography using ethyl acetate as the solvent. The products were precipitated in pet. ether. Yield: 2.36 g (43%). Melting point: 111.5-115° C. UV $\lambda$max=250 nm (9-alkylated); $\lambda$max=260 nm (7-alkylated). 1H-NMR (DMSO-d6): 8.60 (1H, s); 8.43 (1H, s); 7.6-7.35 (5H, m); 5.69 (2H, s); 5.26 (2H, s); 3.75 (3H, s).

(6-(Benzyloxy)purin-9-yl)acetic acid. Methyl (6-(Benzyloxy)purin-9-yl)acetate (2.10 g; 7.0 mmol) was dissolved in methanol (70 ml) and 0.1 M NaOH (85 ml) is added. After 15 min. the pH of the reaction mixture was lowered by addition of 0.1 M HCl (~80 ml) to pH 3. The precipitate was separated from the mixture by filtration and washed with water and ether. Yield: 1.80 g (90.2%). 1H-NMR (DMSO-d6): 8.55 (1H, s); 8.37 (1H, s); 7.55-7.30 (5H, m); 5.64 (2H, s); 5.09 (2H, s).

N-((6-(Benzyloxy)purin-9-yl)acetyl)-N-(2-Boc-aminoethyl)glycine Ethyl N-(2-Boc-aminoethyl)glycinate (0.285 g; 1.15 mmol), (6-(benzyloxy)purin-9-yl)acetic acid (0.284 g; 1.0 mmol) and 3-hydroxy-1,2,3 benzotriazin-4(3H)-one (0.180; 1.1 mmol) was dissolved in dichlormethane/dimethylformamide 1:1 (10 ml). After addition of dicycloehexylcarbodiimide (0.248 g; 1.2 mmol) the reaction was left over night. The precipitate was removed by filtration. The organic phase was extracted twice with saturated sodium bicarbonate, dried with magnesium sulfate and evaporated to a oil. Column purification on silica using dichloromethane with 0-5% methanol as elutant yields the monomer ester which was dissolved in methanol (10 ml). Then, 0.1 M NaOH (12 ml) was added. After 30 min the reaction was filtered and pH adjusted with saturated KHS04/water (1:3) to 2.7. The water phase was extracted twice with ethyl acetate (2×100 ml). The combined organic phases were dried over magnesium sulfate and evaporated to a volume of 10 ml. Precipitation with pet. ether yielded the monomer (0.15 g; 31%). 1H-NMR (DMSO-d6): 8.51 (1H, s); 8.23 (1H, s); 7.6-7.3 (5H, m); 5.64 (2H, s); 5.31 {ma.)+5.13 (mi.) (2H, s); 4.23 (mi.)+3.98 (ma.) (2H, s); 3.55-3.00 (4H, m); 1.36 (9H, s).

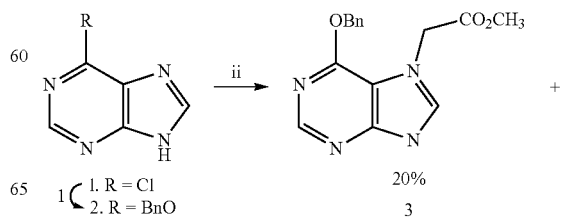

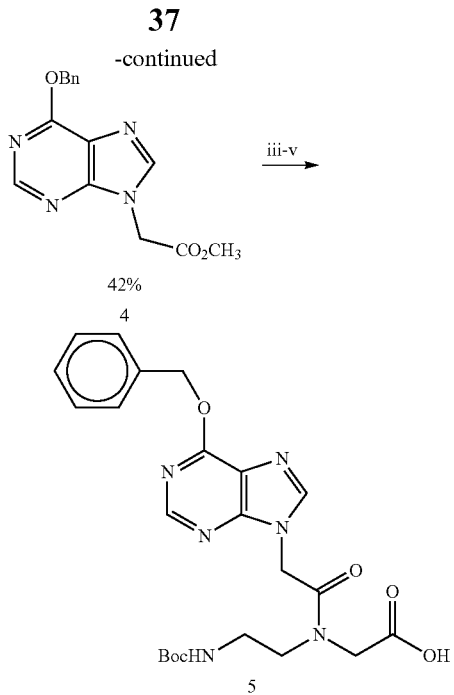

The synthesis of the hypoxanthine PNA monomer, (i) BnOH, NaH (ii) K2C03, BrCH2C02CH3 (iii) OH— (iv) DCC, Dhbt-OH, Boc-aeg-OEt (v) OH—

The Boc-PNA-Diaminopurine-(N-6-Z)-monomer was prepared according to Gerald Haaima, Henrik F. Hansen, Leif Christensen, Otto Dahi and Peter E. Nielsen; *Nucleic Acids Research*, 1997, Vol 25, Issue 22 4639-4643.

The Boc-PNA-2-Thiouracil-(S-4-MeOBz)-monomer was prepared according to Jesper Lohse, Otto Dahl and Peter E. Nielsen; *Proceedings of the National Academy of Science of the United States of America*, 1999, Vol 96, Issue 21, 11804-11808.

The Boc-PNA-Adenine-(Z)-monomer was from PE Biosystems catalog GEN063011.

The Boc-PNA-Cytosine-(Z)-monomer was from PE Biosystems cat. GEN063013.

The Boc-PNA-Guanine-(Z)-monomer was from PE Biosystems cat. GEN063012.

The Boc-PNA-Thymine-monomer was from PE Biosystems cat. GEN063010.

IsoAdenine (2-aminopurine) may be prepared as a PNA-monomer by 9-N alkylation with methylbromoacetate, protection of the amino group with benzylchloroformate, hydrolysis of the methyl ester, carbodiimide mediate coupling to methyl-(2-Boc-aminoethyl)-glycinate, and finally hydrolysis of the methyl ester.

4-thiouracil may be prepared as a PNA-monomer by S-protection with 4-methoxy-benzylchloride, 1-N alkylation with methylbromoacetate, hydrolysis of the methyl ester, carbodiimide mediate coupling to methyl-(2-Boe-aminoethyl)-glycinate, and finally hydrolysis of the methyl ester.

Thiocytosine may be prepared as a PNA monomer by treating the Boc-PNA-eytosine(Z)-monomer methyl ester with Lawessons reagent, followed by hydrolysis of the methyl ester.

A number of halogenated bases are commercially available, and may be converted to PNA monomers analogously to the non-halogenated bases. These include the guanine analog 8-bromo-guanine, the adenine analogs 8-bromo-adenine and 2-fluoro-adenine, the isoadenine analog 2-amino-6-ehloro-purine, the 4-thiouracil analog 5-fluoro-4-thio-uracil, and the 2-thiouraeil analog 5-chloro-2-thiouracil.

Boc-PNA-Uracil monomers were first described in "Uracil og 5-bromouracil I PNA," a bachelor project by Kristine Kilsa Jensen, Kobenhavns Universitet 1992.

Example 18

Miscellaneous Standard Procedures a. Loading of resins. P-methyl-BHA-resin (3 g) is loaded with Boc-Lys(Fmoc)-OH 15 mmoVg resin. The lysine is dissolved in NMP and activated with 0.95 equivalents (eq.) HATU and 2 eq. DIPEA. After loading the resin, it is capped by adding a solution of $(Ac)_2O/NMP/pyridine$ (at a ratio of 1/2/2) and letting it set for at least 1 hour or until Kaiser test was negative. After washing with DCM, the resin is dried in a dessicator. Quantitative Kaiser test typically gives a loading of 0.084 mmol/g.

b. Amino Acid Couplings. The Boc protection group is removed from the resin with TFA/m-cresol (at a ratio of 95/5) 2×5 min. The resin is then washed with DCM, pyridine and DMF before coupling with the amino acid, which is dissolved in NMP in a concentration between 0.2 and 0.4 M and activated with 0.95 eq. of HATU and 2 eq of DIPEA for 2 minutes. The coupling is complete when the Kaiser test is negative. Capping occurring by exposing the resin for 3 minutes to $(Ac)_2O/pyridine/NMP$ (at a ratio of 1/2/2). The resin is then washed with DMF and DCM c. $Boc-L_{300}-Lys(Fmoc)$-resin. To the loaded Boc-Lys (Fmoe)-resin, $L_3o$-Linker in a concentration of 0.26 M was coupled using standard amino acid coupling procedure. This was done 10 times giving $Boc-L_3oo-Lys(Fmoc)$-resin.

d. PNA solid phase. On a peptide synthesizer (ABI 433A, Applied Biosystems) PNA monomers are coupled to the resin using standard procedures for amino acid coupling and standard PNA chemistry. Then the resin is handled in a glass vial to remove protections groups and to label with either other amino acids or fluorophores.

Removal of the indicated protection groups is achieved with the following conditions:

Boc: TFA/m-cresol (at a ratio of 95/5) 2×5 min.
Fmoc: 20% piperidine in DMF 2×5 min.
Dde: 3% hydrazine in DMF 2×5 min.

When the synthesis is finished, the PNA is cleaved from the resin with TFA/TFMSA/m-eresol/thioanisol (at a ratio of 6/2/1/1). The PNA is then precipitated with ether and purified on HPLC, MALDI-TOF mass spectrometry is used to determine the molecular weight of the product.

e. Labeling with fluorescein. 5(6)-carboxy fluorescein is dissolved in NMP to a concentration of 0.2 M. Activation is performed with 0.9 eq. HATU and 1 eq. DIPEA for 2 min before coupling for at least 2×20 min or until the Kaiser test is negative.

Example 19

PNA with Positive and Negative Loadings

In order to make better conjugations at one time we tried to give the PNA a loading. Both PNA's were made by PNA standard procedures (See Example 18), 1. $Flu-L_3o-Glu-TCA-AGG-TAC-A-Glu-L_3oo-Lys(Cys)$ Glu=glutamate has negative loadings and for the easiness the PNA is designated-A4

2. $Flu-L_{30}-Lys(Me)2-TGT-ACC-TTG-A-Lys(Me)2-L_{33}o-Lys(cys)$

Lys(Me)$_2$=Boc-Lys(Me)$_2$—OH has positive loadings and the PNA is designated+T+

TABLE 4

| name | number | HRP | GaM | equiv. | HRP/ Dex | GaM/Dex | PNA/ Dex |
|---|---|---|---|---|---|---|---|
| −A4− | D 13041 | D 13050 | | 9 | 12.3 | | 0.13 |
| −A4− | D 13041 | | D 13060 | 7 | | 0.94 | 0.66 |
| +T4+ | D 13042 | D 13058 | | 9 | 13.5 | | 0.19 |
| +T4+ | D 13042 | | D 13056 | 7 | | 1.42 | 0.45 |

As it is shown in the scheme, PNAs with loading are not good at coupling.

Example 20

Target Detection: Procedures Used in the Examples Below

1. Fixation of Biological Samples

Tonsil tissue samples were fixed in neutral buffered formalin, NBF (10 mM NaH$_2$PO$_4$/Na$_2$HPO$_4$, pH 7.0), 145 mM NaCl, and 4% formaldehyde (all obtained from Merck, Whitehouse Station, N.J.). The samples were incubated overnight in a ventilated laboratory hood at room temperature.

2. Sample Dehydration and Paraffin Embedding

The tissue samples were placed in a marked plastic histocapsule (Sakura, Japan). Dehydration was performed by sequential incubation in 70% ethanol twice for 45 min, 96% ethanol twice for 45 min, 99% ethanol twice for 45 min, and xylene twice for 45 min. The samples were subsequently transferred to melted paraffin (melting point 56-58° C.) (Merck, Whitehouse Station, N.J.) and incubated overnight (12-16 hours) at 60° C. The paraffin-infiltrated samples were transferred to fresh warm paraffin and incubated for an additional 60 min prior to paraffin embedding in a cast (Sekura, Japan). The samples were cooled to form the final paraffin blocks. The marked paraffin blocks containing the embedded tissue samples were stored at room temperature in the dark.

3. Cutting, Mounting and Deparaffination of Embedded Samples

The paraffin blocks were cut and optionally also mounted in a microtome (0355 model RM2065, Feather S35 knives, set at 5.0 micrometer; Leica, Bannockbum, Ill.). The first few millimeters were cut and discarded. Paraffin sections 4-6 micrometers thick were then cut and collected at room temperature. The sections were gently stretched on a 45-60° C. hot water bath before being mounted onto marked microscope glass slides (SUPERFROST® Plus; Fisher, Medford, Mass.), two tissue sections per slide. The slides were then dried and baked in an oven at 60° C. The slides were deparaffinated by incubating twice in xylene for 5 min±2 min twice, then in 96% ethanol for 2 min+/−30 sec, then twice in 70% ethanol for 2 min+/−30 sec, and then once in Tris-buffered saline with TWEEN® (called herein TBST) for 5 min. TBST comprises 50 mM Tris adjusted to pH 7.6 with HCl; 150 mM NaCl; 0.05% TWEEN20. The slides were deparaffinated by subsequently incubation in xylene twice for 5 min±2 min, 96% ethanol twice for 2 min+/−30 sec and 70% ethanol twice for 2 min+/−30 sec. The slides were immersed in deionized water and left for 1 to 5 min.

4. Endogenous Peroxidase Blocking

Samples were incubated with a 3% hydrogen peroxide solution for 5 min. to quench endogenous peroxidase activity, followed by washing in deionized water for 1 to 5 min.

5. Antigen Retrieval by Microwave Oven

Antigens in the sample were retrieved by immersing the slides in a container containing Antigen Retrieval Solution, pH 6.0 (DakoCytomation code No. K5204 Vial 7 or optional code No. K5205 Vial 7). The container was closed with a perforated lid and placed in the middle of a microwave oven and left boiling for 10 min. The container was removed from the oven and allowed to cool at room temperature for 20 min. The samples were rinsed in deionized water.

6. Antigen Retrieval by Water Bath Incubation

Antigens in the sample were retrieved by immersing the slides in a beaker containing Antigen Retrieval Solution, pH 6.0 (DakoCytomation code No. K5204 Vial 7 or optional code No. K5205 Vial 7). The samples were incubated for 40 min in a water bath at 95-100° C. The beaker was removed from the water bath and allowed to cool at room temperature for 20 min. The samples were rinsed in deionized water.

7. Water-repellent Barrier to Liquids by DakoCytomation Pen

To ensure good coverage of reagent on the tissue sample, the area on the slide with tissue was encircled with a silicone rubber barrier using DakoCytomation Pen (DakoCytomation code No. 2002). The slides were transferred to a rack and placed in a beaker containing Tris-buffered saline with TWEEN® (called herein TBST) and left for 5 min. TBST comprises 50 mM Tris adjusted to pH 7.6 with HCl; 150 mM NaCl; 0.05% TWEEN®20.

8. Application of a Primary Antibody

Monoclonal Mouse anti-Human Cytokeratin (DakoCytomation code No. M3515) diluted 1:900 in ChemMate® Antibody Diluent (DakoCytomation code No.S2022) was applied on the tissue samples and incubated for 30 min in a humid chamber at ambient temperature. The slides were individually rinsed and then washed in TBST for 5 min.

9. Application of Three Primary Antibodies

Monoclonal Mouse Anti-Human Cytokeratin (DakoCytomation code No. M3515) diluted 1:300, 1:900 and 1:1600; monoclonal Mouse Anti-Human CD20cy (DakoCytomation code No. M0755) diluted 1:2000, 1:8000 and 1:14000; and monoclonal Mouse Anti-Human Ki-67 Antigen (DakoCytomation code No. M7240) diluted 1:400, 1:1200 and 1:2400 were used. The antibodies were diluted in ChemMate™ Antibody Diluent (DakoCytomation code No. S2022), applied on the tissue samples, and incubated for 30 min in a humid chamber at ambient temperature. The slides were individually rinsed and washed in TBST for 5 min.

10. Application of an Antibody/Dextran/PNA1 Conjugate Recognition Unit

Antibody/Dextran/PNA1 conjugate recognition unit is also called "PNA1 conjugate" in the examples that follow. The PNA1 conjugate comprises 70,0000 molecular weight dextran. Table 5 summarizes PNA1 conjugates based on a secondary antibody: goat anti-mouse Ig, called herein GAM (DakoCytomation code No. Z0420). Table 6 summarizes PNA1 conjugates based on a primary antibody: mouse anti-human BCL2 oncoprotein, such as Clone 124 (DakoCytomation code No. M0887). The primary antibody was protein A-purified prior to conjugation. The conjugates were diluted in BBA (50 mM Tris adjusted to pH 7.6 with HCl; 150 mM NaCl; 2% BSA; 0.02% bronidox; 2.44 mM 4-aminoantipyrin) and were applied on the tissue sample in a range of dilutions, then incubated for 30 min in a humid chamber at ambient temperature. The slides were individually rinsed and washed in TBST for 5 min.

TABLE 5

PNA1 conjugates useful in indirect recognition of targets: GAM/Dextran/PNA1

| Conjugate No. | Sequence | µM Dex | GAM/ Dex | PNA1/ Dex |
|---|---|---|---|---|
| D14120 | AGACPTTPGDPT | 1.25 | 1.1 | 4.3 |
| D14102 | GTP TAA TTP PAG | 1.02 | 1.0 | 9.1 |
| D14096 | GTP TAD TTP PAG | 1.15 | 1.4 | 4.2 |
| D14083 | $U_SGU_S$ DPP TTG D | 0.87 | 0.8 | 5.3 |
| D13171 | $U_SGU_S$ DPP TTG D | 1.21 | 1.0 | 7.5 |
| D13161 | TTGAPPTTAG | 2.11 | 1.1 | 6.0 |
| D13150 | TGT APP TTGA | 2.20 | 1.1 | 4.2 |
| D13102 | TGT ACC TTGA | 2.53 | 1.1 | 2.5 |
| D12102 | TGT ACC TTGA | 2.50 | 1.3 | 4.5 |

TABLE 6

PNA1 conjugates for direct recognition of targets: anti-BCL2/Dextran/PNA1

| Conjugate No. | Sequence | µM Dex | Ab/ Dex | PNA1/ Dex |
|---|---|---|---|---|
| D14128 | $U_SGU_S$ DPP TTG D | 0.8 | 1.1 | 5.6 |
| D14126 | $U_SGU_S$ DPP TTG D | 1.0 | 1.2 | 2.9 |
| D14122 | $U_SGU_S$ DPP TTG D | 1.1 | 1.6 | 9.5 |

In the above tables, the letters A, C, G, U, and T, stand for the natural bases adenine, cytosine, guanine, uracil, and thymine. P stands for pyrimidinone, D for 2,6-diaminopurine, and $U_s$ for 2-thiouracil.

11. Fixation of PNAt-conjugate with 1% glutardialdehyde

The samples were washed in deionized water for 30 sec. Then, 1% glutardialdehyde (Merck Art. No. 820603), called herein GA, diluted in 22 mM calcium phosphate buffer, pH 7.2, was applied, and the samples were incubated for 10 min in a humid chamber at ambient temperature. The samples were washed in deionized water for 30 sec and in TBST for 5 min.

12. Application of a $PNA^1$-$PNA^2$/Dextran Coniuaate Adaptor Unit $PNA^1$-$PNA^2$/Dextran conjugate is also called "$PNA^1$-$PNA^2$" in the following examples. Table 7 summarizes the compositions of $PNA^1$-$PNA^2$ conjugates. $PNA^1$ is complementary to the PNA1 conjugate, and $PNA^2$ is complementary to the PNA2 conjugates D14079 and D13155 described in step 13 below. The sequence of $PNA^1$ is $CU_SG_S$ $G_S$DD $TU_S$D $G_S$DC and the sequence of $PNA^2$ is $U_SGU_S$DPP TTG D, in which $U_s$ stands for 2-thio-uracil, $G_s$ stands for 2-amino-6-thioxopunne, D stands for diaminopurine, and P stands for pyrimidinone. The conjugates, diluted in BBA, were applied to the tissue samples in a range of dilutions, and the samples were then incubated for 30 min in a humid chamber at ambient temperature. The samples were individually rinsed and washed in TBST for 5 min. When testing a $PNA^1$-$PNA^2$ conjugate, fixed concentrations of 0.08 µM PNA1 and 0.05 µM PNA2 were used.

TABLE 7

$PNA^1$-$PNA^2$/Dextran conjugates

| Conjugate No. | Molecular weight of dextran | $PNA^1$/dex | $PNA^2$/dex | µM $PNA^1$ |
|---|---|---|---|---|
| D14119 | 150.000 | 2.3 | 11.5 | 4.2 |
| D14106 | 150.000 | 0.8 | 12.7 | 1.3 |
| D14104 | 70.000 | 1.5 | 7.5 | 3.9 |

13. Application of Horse Radish Peroxidase Dextran/PNA2 Conjugate Detection Unit Horse Radish Peroxidase (HRP)/Dextran/PNA2 conjugates are also called "PNA2 conjugate" in the examples that follow, and are listed in table 8. The PNA2 conjugates comprise 70.000 Da molecular weight dextran. The conjugates diluted in BBA were applied to the tissue samples in a range of dilutions, and samples were incubated for 30 min in a humid chamber at ambient temperature. The samples were individually rinsed and washed twice in TBST for 5 min.

TABLE 8

PNA2 conjugates: HRP/Dextran/PNA2

| Conjugate No. | Sequence | µM PNA | HRP/ Dex | PNA2/ Dex |
|---|---|---|---|---|
| D14133 | TCD DII TAG A | 1.6 | 14.0 | 1.0 |
| D14114 | $DG_ST$ $CG_SD$ $DG_SG$ $U_SCU_S$ | 3.9 | 11.4 | 2.1 |
| D14110 | DGT $CG_SD$ $DG_SG$ $U_SCU_S$ | 3.0 | 12.6 | 1.6 |
| D14089 | $CU_SG_S$ $G_S$DD $TU_S$D $G_S$DC | 2.1 | 14.1 | 1.5 |
| D14086 | $U_SCG_S$ $G_S$DD $TU_S$D GDC | 1.9 | 11.0 | 1.0 |
| D14079 | TCD $DG_SG_S$ TAC A | 1.9 | 12.2 | 1.2 |
| D13159 | CTA $AG_SGs$ TCA A | 1.9 | 12.9 | 1.3 |
| D13155 | TCD $DG_SGs$ TAC A | 2.4 | 12.7 | 1.6 |
| D13148 | TCA $AG_SG_S$ TAC A | 1.9 | 11.6 | 0.8 |
| D13122 | CTA AGG TCA A | 3.2 | 13.0 | 2.1 |
| D13108 | GTG TGT GT | 4.3 | 12.0 | 2.3 |
| D13106 | TCA AGG TAC A | 2.6 | 12.4 | 1.3 |
| D12120 | TCD DGG TAC A | 1.0 | 18.3 | 0.6 |
| D12094 | TCA AGG TAC A | 3.0 | 14.6 | 0.9 |

In table 8, in addition to the nucleobase letter schemes provided for Tables 5-7, I stands for inosine.

14. Application of Diaminobenzidine Chromogenic Substrate Solution

The diaminobenzidine chromogenic substrate solution, DAB+(DakoCytomation code No. K3468) was applied on the tissue samples, and the samples were incubated for 10 min in a humid chamber at ambient temperature. The samples were washed with deionized water for 5 min.

15. Counterstaining with Hematoxylin

The tissue samples were immersed in Mayers Hematoxylin (Bie & Bemtsen Code No. LAB00254) for 3 min, rinsed in tap water for 5 min, and finally rinsed with deionized water.

16. Cover Slipping

Cover slips were applied to the tissue samples using the aqueous mounting media, Faramount (DakoCytomation code No. S3025)

17. Evaluation of the Performance

The tissue staining was examined in a bright field microscope at 10×, 20× or 40×magnification. Both the specific and the non-specific staining intensity were described with a score-system using the range 0 to 3+ with 0.5+ score interval. ChemMate™ EnVision™ Detection kit Rabbit/Mouse (DakoCytomation code No. K5007 bottle A) was used as a reference, and was included in all experiments for testing in parallel with the PNA conjugates. K5007 was used according to manufacturer's instructions. The antibodies were used in the following dilutions: M3515 at 1:900, M0755 at 1:8000, and M7240 at 1:1200. The staining intensity of the K5007 reference using the primary antibody M3515 diluted 1:900 was set to 2+ in order to compare and assess the staining result of the PNA conjugate tested. If the reference deviated more than ±0.5, the test was repeated.

In the examples, the various visualization system combinations of the invention were tested on routine tissue samples. The staining performance was compared with a reference visualization system, using EnVision™ and a very dilute antibody from DakoCytomation. The practical dynamic range of quantitative IHC may be narrow, and e.g. strongly stained (+3) tissues are not easy to compare with respect to intensity. Therefore, on purpose, the staining intensity of the reference system was adjusted to be approximately +2. This was done in order to better monitor and compare differences in staining intensity with the system of the Invention.

Example 21

Protocol for Fast Evaluation of Non-specific Binding of PNA2 Conjugates

The protocol allowed for a quick test of PNA2 conjugates for nonspecific staining. Tonsil tissues were taken through the steps 1-5, 7, 13-14, 15 (in which the slides were immersed in a bath of Hematoxylin Mayer for 1 min.), and 16-17, above. The conjugates to be tested were diluted to the final concentrations 0.05 µM and 0.2 µM. As references, two PNA2 conjugates were used in the final concentration 0.05 µM. The first reference, for example, PNA2, D13108, was known to give non-specific nuclear staining, and so was used as a positive control. The second reference, for example, PNA2, D13155, was known not to give any non-specific nuclear staining, and was used as a negative control. In general, 250 µL of each reagent was applied unless otherwise specified.
Protocol for Test of a PNA Pair with One Antibody.

Tonsil tissues were taken through the steps 1-4, 6-8, 10, 11, and 13-17 above. Step 11 was left out for the tonsils not fixed with 1% GA. In general, 250 µL of each reagent was applied unless otherwise specified.
Protocol for test of 3-Layer PNA conlugates Tonsil tissues were taken through the steps 1-4, 6-8, and 10-17 above. Step 11 was left out for the tonsils not fixed with 1% GA. In general, 250 µL of each reagent was applied unless otherwise specified.
Protocol for Test of a PNA Pair with 3 Antibodies Tonsil tissues were taken through the steps 1-4,6,7,9-11, and 13-17 above. Step 11 was left out for the tonsils not fixed with 1% GA. A further negative control, mouse IgG1 (Dako-Cytomation code No. X0931) diluted 1:300 in S2022 was included the protocol for the PNA conjugates. In general, 250 µL of each reagent was applied unless otherwise specified.

Example 22

Testing and Selection of PNA Pairs

Conjugates comprising example PNA segments were tested for their ability to specifically hybridize according to the invention. Tonsil tissues were taken through the steps 1-4, 6-8, 10 and 13-17 above. K5007 was included as a reference to secure the level of the staining. The concentration of the conjugates was 0.08 µM for PNA1 and 0.05 µM for PNA2.

The results listed in Tables 9 and 10 show the staining intensities for a representative number of PNA pairs tested. The PNA pairs did not demonstrate any non-specific binding. The specific staining, in general, was directly proportional to the number of hydrogen bonds involved in the base-pairing. It was important that each PNA did not interact with itself. Substitution of T (thymine) with $U_s$ (2-thiouracil) in some PNAs could prevent such intra-PNA interactions. The unspecific staining intensity was increased by substituting an A with a D. On the other hand, we also observed that replacement of one G (guanine) with $G_s$ (2-amino-6-thioxopurine) in the same PNA could circumvent the unspecific binding introduced by D. For instance, the staining of the PNA1 conjugate D14102 was improved by substituting the D in D14096 with an A in D14102. As is apparent from Table 9, this small change resulted in an increase of the specific staining score by 1+.

TABLE 9

| PNA1 | PNA2 | Specific staining intensity | Non-specific staining intensity |
|---|---|---|---|
| D13161 | D13159 | 2 | 0 |
| D14083 | D14079 | 2.5 | 0 |
| D14096 | D14089 | 1.5 | 0 |
| D14102 | D14089 | 2.5 | 0 |
| D14120 | D14114 | 1.5 | 0 |

Example 23

The effect of base substitution on PNA-speeifle Binding Intensities

The PNA pair D13102-D13106 was used as a starting point for further investigation of introducing base substitutions in either PNA1 or PNA2 conjugates. Tonsil tissues were taken through the steps 1-4, 6-8, 10 and 13-17. Each of the three different PNA1 conjugates was tested with each of the three different PNA2 conjugates. The concentration of the conjugates used was 0.08 µM for PNA1 and 0.05 µM for PNA2.

TABLE 10

| PNA2: | D13106 | D13148 | D13155 |
|---|---|---|---|
| PNA1: | TCA AGG TAC A | TCA AG$_s$G$_s$ TAC A | TCD DG$_s$G$_s$ TAC A |
| D13102<br>TGT ACC<br>TTG A | 2.5 | 0 | 2 |
| D13150<br>TGT APP<br>TTG A | 2.5 | 0.5 | 3 |
| D13171<br>U$_s$GU$_s$ DPP<br>TTG D | 3 | 2.5 | 3 |

Table 10 shows the effect of base substitutions on the specific binding between paired PNA variants. No non-specific binding was observed. D131Q2 tested with D13106 gave a specific staining of 2.5+. Replacement of 2 G's with 2 $G_s$'s (D13148) resulted in the abolishment of specific staining, but by introducing 2 D's instead of 2 A's (D13155) achieved a specific staining of 2+. When the 2 C's in D13102 were replaced with 2 P's (D13150) and tested with D13106, the specific staining was unchanged at 2.5+, despite the lower number of hydrogen bonds as compared to the PNA-pair D13102-D13106. Test of D13150 with D13148 resulted in a reduced specific staining of 0.5+, whereas specific staining to 3+ was observed for the D13150-D13155 pair. The replacement in D13150 of 2 A's with 2 D's and of 2 T's with 2 $U_s$'s (D13171) resulted in improved specific binding compared to D13106. This modified PNA1 was now able to bind specifically to D13148 with a score of 2.5+, and also bound to D13155.

This experiment clearly demonstrates the use of PNA pairs in the present invention. Furthermore, it shows the ability of fine tuning the specific binding by introducing base substitutions using either natural as well as non-natural bases.

Example 24

Test of Cross Reactivity

The two PNA-pairs, D13150-D13155 and D13161-D13159, were tested for cross-reactivity. Tonsil tissues were taken through the steps 1-4, 6-8, 10, and 13-17. The concentration of conjugates used was 0.16 µM for PNA1 and 0.1 µM for PNA2.

As apparent from Table 11, PNA1 D13150 did not cross react with PNA2 D13159, but PNA1 D13161 cross reacted with PNA2 D13155. We therefore excluded the PNA pair D13161-D13159 due to the cross-reaction between D13161 and D13155. No non-specific staining was observed.

TABLE 11

Test of specific binding and cross reactivity

| PNA1: | PNA2: | |
|---|---|---|
| | D13155 | D13159 |
| D13150 | 2.0 | 0 |
| D13161 | 1 | 1.5 |

Example 25

Test of Cross Reactivity

Three PNA-pairs, D14083-014079, D14102-D14089 and D14120-014114 were tested for cross-reactivity. Tonsil tissues were taken through the steps 1-4, 6-8, 10, and 13-17. The concentration of the conjugates used was 0.08 µM for PNA1 and 0.05 µM for PNA2.

The PNA conjugates listed in Table 12 only bound to their complementary partner and did not cross react to any of the other PNA conjugates tested. No non-specific staining was observed. See Table 12 below.

TABLE 12

Test of specific binding and cross reactivity

| PNA1: | PNA2: | | |
|---|---|---|---|
| | D14079 | D14089 | D14114 |
| D14083 | 1.5 | 0 | 0 |
| D14102 | 0 | 1 | 0 |
| D14120 | 0 | 0 | 1.5 |

Example 26

Two PNA pairs, D14083-D14079 and D14096-D14089, were tested at different PNA2 concentrations for the purpose of determining the optimal, concentration of PNA2 conjugates. The concentrations used were 0.08 µM for PNA1 conjugates and 0.025; 0.05; 0.1 and 0.2 µM for PNA2 conjugates.

Tonsil tissues were taken through the steps 1-4, 6-8, 10, and 13-17. The optimal concentration of the PNA2 conjugate was 100 nM, See Table 13 below.

TABLE 13

Determination of PNA2 conjugate concentration.

| | 1% GA fixation of | | Specific staining | | | |
|---|---|---|---|---|---|---|
| PNA1 | PNA1 | PNA2 | 0.025 µM | 0.05 µM | 0.1 µM | 0.2 µM |
| D14083 | − | D14079 | 1.5 | 2 | 3 | 2.5 |
| D14096 | − | D14089 | 0.5 | 1 | 2 | 1.5 |

Tonsil tissues were taken through the steps 1-4, 6-8, 10, 11, and 13-17. Step 11 was omitted for tissues not fixed with 1% GA.

Fixation of PNA1 conjugates with 1% GA resulted in a stronger specific staining than without fixation and the optimal concentration of the PNA2 conjugate was now determined to be 50 nM. See Table 14 below.

TABLE 14

Effect of 1% GA fixation on the determination of PNA2 conjugate concentration.

| | 1% GA fixation of | | Specific staining | | | |
|---|---|---|---|---|---|---|
| PNA1 | PNA1 | PNA2 | 0.025 µM | 0.05 µM | 0.1 µM | 0.2 µM |
| D14088 | − | D14079 | 2 | 2 | 2.5 | 2.5 |
| D14083 | + | D14079 | 2.5 | 8 | 2.5 | 3 |

Example 27

2-Layer Versus 3-Layer PNA Systems

This example shows the results of using a 3-layer PNA system employing a PNA$^1$-PNA$^2$/Dextran conjugate adaptor unit to link the PNA1 and PNA2 conjugates together. Tonsil tissues were taken through the steps 1-4, 6-8, and 10-17. Step 11 was omitted for tissues not to be fixed with 1% GA. The concentration of the conjugates used was 0.08 µM for PNA1, 0.1 µM (calculated based on PNA$^1$) for PNA$^1$-PNA$^2$ and 0.05 µM for PNA2.

Table 15 shows that a 3-layer system resulted in a stronger specific staining intensity in comparison with a 2-layer system. No non-specific staining was observed.

TABLE 15

Improvement of staining intensity by using 3 layers

| PNA1 | 1% GA fixation of PNA1 | PNA-PNA | PNA2 | Specific staining intensity |
|---|---|---|---|---|
| D14096 | + | D14104 | D14079 | 2 |
| D14096 | − | D14104 | D14079 | 2 |
| D14096 | − | — | D14089 | 1 |

The introduction of a fixation step after the application of PNA1 resulted in an increase in specific staining. The specific staining was increased with 1+ score in the 3-layer system as shown in Table 16. Surprisingly no nonspecific staining was observed despite the use of a multi-layer PNA-system.

TABLE 16

Improvement of specific staining in a 3-layer system by fixation

| PNA1 | 1% GA fixation of PNA1 | PNA-PNA | PNA2 | Specific staining intensity |
|---|---|---|---|---|
| D14102 | + | D14119 | D14079 | 3 |
| D14102 | + | D14106 | D14079 | 3 |
| D14102 | + | D14104 | D14079 | 3 |
| D14102 | − | D14119 | D14079 | 2 |
| D14102 | − | D14106 | D14079 | 2 |
| D14102 | − | D14104 | D14079 | 2 |

Example 28

Test of 3-Layer PNA Systems Using Different PNA$^1$-PNA$^2$ Concentrations in the Presence or Absence of Fixation Tonsil tissues were taken through the steps 1-4, 6-8, and 10-17 above. Step 11 was left out for the tonsil tissues, which were not going to be fixed with 1% GA. The concentration of the conjugates in the table was 0.08 µM for PNA1, 0.025, 0.05, 0.1 and 0.2 µM for PNA$^1$-PNA$^2$ (based on [PNA$^1$]), and 0.05 µM for PNA2.

Fixation of PNA1 increased the specific staining intensity with 0.5+ to 1+ score.

TABLE 17

The effect of using different PNA$^1$-PNA$^2$ concentrations.

| PNAs | 1% GA | Specific staining intensity at various PNA$^1$-PNA$^2$ concentration | | | |
|---|---|---|---|---|---|
| | | 0.025 µM | 0.05 µM | 0.1 µM | 0.2 µM |
| D14102 D14119 D14079 | + | 2.5 | 2.5 | 3 | 3 |
| | − | 2 | 2 | 2 | 2 |
| D14096 D14104 D14079 | + | 1.5 | 2 | 2 | 3 |
| | − | 1 | 1.5 | 2 | 2.5 |

Example 29

Effect of Using Different Concentrations of Glutardialdehyde (GA) for Fixation of PNA1

A 2-layer PNA test system was employed to study the effect of using different concentrations of GA. Tonsil tissues were taken through the steps 1-4, 68, 10, 11 and 13-17. In step 11, the concentration of GA used was 0.1%, 0.3% and 1.0% respectively. The PNA pair, D14083-D14079, was used at concentrations of 0.08 µM for PNA1 and 0.05 µM for PNA2. After fixation of PNA1 conjugates, the tissues were processed with one of three treatments listed in Table 18.

The specific staining in the 2-layer PNA system was improved when the PNA1 conjugate was fixed with at least 0.3% GA, even when the tissues were boiled in target retrieval buffer in microwave oven for 10 min. This shows the possibility of including a strong cross linking step to the procedure. The cross linking allows a harsh treatment with no sacrifice to the staining result.

TABLE 18

Staining intensity at different Glutardialdehyde (GA) concentration.

| Treatment after GA-fixation of PNA1 | Specific staining intensity | | |
|---|---|---|---|
| | 0.1% GA | 0.3% GA | 1.0% GA |
| Wash in TBST at RT for 20 min. | 1.5 | 1.5 | 1.5 |
| Wash in TBST at 65° C. for 10 min. | 1.0 | 1.5 | 1.5 |
| Target retrieval (K5204) in MW oven for 10 min. | 1.0 | 1.5 | 1.5 |

Example 30

Comparison of a PNA-based Detection System with an EnVision™ Based Detection System Tonsil tissues were taken through the steps 1-4,6,7,9-10, and 13-17. The concentration of the conjugates was 0.08 µM for PNA1, D12102 and 0.05 µM for PNA2, D12094. A negative Ig control, mouse IgG1 (DakoCytomation code No. X0931) diluted 1:300 in S2022 was included in the protocol for PNA conjugates. The EnVision™-based detection system, K5007, was used in parallel with the PNA based detection system.

The specific staining intensities obtained for the three antibodies tested and visualized with either the D12102-D12094 PNA-pair or K5007 are shown in Table 19. The PNA based system showed in general a stronger specific staining in comparison with the reference K5007.

TABLE 19

Comparison between two indirect detection systems.

| Primary antibody | Dilution of primary antibody | Specific staining intensity | |
|---|---|---|---|
| | | PNA based detection system | EnVision ™-based detection system |
| M3515 | 1:300 | 3 | — |
| | 1:900 | 2.5 | 2 |
| | 1:1600 | 1.5 | — |
| M7240 | 1:400 | 3 | — |
| | 1:1200 | 2.5 | 2 |
| | 1:2400 | 1.5 | — |
| M0755 | 1:2000 | 3 | — |
| | 1:8000 | 2.5 | 2 |
| | 1:14000 | 1.5 | — |
| X0931 | 1:300 | 0 | 0 |

Example 31

Recognition of a Conjugated Primary Antibody by Another Detection System

Tonsil tissues were taken through the steps 1-4,6,7,10, 11, 1S and 14-17 above. 20 µL of PNA1, respectively D14122 and D14128 (0.08 and 0.3 µM) were applied. Slides were cover slipped during incubation with PNA1. Then 200 µL PNA2, D14079 (0.1 µM) was applied. Samples were incubated with K5007 GaM:HRP complex for 30 min in parallel with PNA2 conjugates in step 13. As a further control and for comparison, tonsil tissues were taken through steps 1-4 and 6-8 using uncomplexed anti-BCL2, M0887, diluted 1:100 to a concentration of 0.015 μM in S2022 as primary antibody, and visualized by incubation with K5007 GaMrHRP complex for 30 min. as an alternative to the PNA2 conjugates in step 13. These slides were then taken through steps 14-17.

Table 20 summarizes the staining results. When preparing PNA conjugates with multiple PNAs, here illustrated by PNA1, the PNAs remained accessible for hybridization to complementary PNAs comprised in components further comprising dextran and enzymes. Conjugates comprising more PNA did not necessarily show improved specific staining. Instead, the amount of staining peaked and then fell as the PNA to dextran ratio increased. For example, samples incubated with D14126 scored 1.0+, those with D14128 scored 2.5+, and those with D14122 scored 2.0+. Thus, D14128, with a PNA:Dextran ratio of about six, gave a stronger signal than both D14122 with a PNA:Dex ratio of about nine as well as D14126 with a PNA:Dex ratio of about three. When preparing PNA conjugates with multiple PNAs, here Illustrated by PNA1, the PNAs remained accessible for hybridization to complementary PNAs comprised in components further comprising dextran and enzymes.

This experiment also illustrates that the conjugation of multiple PNAs to an antibody may reduce the recognition of the antibody by a secondary antibody¡enzyme complex. Samples treated with anti-BCL2 antibody conjugated with PNA1 resulted in specific staining intensities of 2.5+ with PNA2 and 1.5+ with K5007 respectively. Samples treated with free anti-BCL2 and K5007 showed a 3+ score. The signal obtained with K5007 decreased with the number of PNA in the PNA1 conjugate.

TABLE 20

Significance of the amount of PNA in PNA1 conjugates on specific staining intensity.

| | PNA/dextran | Specific staining intensity with PNA2, D14079 | Specific staining intensity with K5007 |
|---|---|---|---|
| PNA1, D14126 0.3 μM | 2.9 | 1.0 | — |
| PNA1, D14128 0.3 μM | 5.6 | 2.5 | 1.5 |
| PNA1, D14128 0.08 μM | 5.6 | 0.5 | 1.0 |
| PNA1, D14122 0.3 μM | 9.5 | 2 | 1.5 |
| PNA1, D14122 0.08 μM | 9.5 | 0.5 | 0 |
| Unconjugated, M0887 | — | — | 3.0 |

Example 32

Test of Non-specific Binding Due to PNA2 Conjugates

Tonsil tissues were taken through the steps 1-5,7,13 and 14-17 above. The PNA2 conjugates tested are listed in Table 21. Replacing 2 D's in D12120 with 2 A's (D13106) reduced the non-specific staining from 3+ to 1+ (at 0.05 μM PNA2). When 2 G's in D13106 were replaced with 2 $G_s$'s (D13148), the non-specific staining was reduced from 1+ to 0. Reintroducing 2 D's in D13155 instead of 2 A's (D13148) increased the non-specific staining from 1.5+ to 2.0+(at 0.2 μM PNA). Both D12120 and D13155 had 2 D's in the sequence, but the nonspecific staining in D13155 did not reach the same level as in D12120, probably due to the 2 $G_s$'s in D13155. The same effect of non-natural bases was seen when comparing D12120 with D14133: the non-specific staining in D14133 did not reach the same level as in D12120, this time probably due to 2 inosines (I)'s in D14133. The replacement of 2 G's in D13122 with 2 G,'s (D13159) reduced the non-specific staining from 3+ to 0 (at a PNA concentration of 0.2 μM). Substitution of 1 G in D14110 with 1 Gs (D14089), reduced the non-specific staining from 1+ to 0. Equally, 1 G in D14086 was replaced with 1 $G_s$ (D14089), resulting in a reduction of the non-specific staining from 3+ to 0 (at a PNA concentration of 0.2 μM).

The non-specific background staining generated by the PNA2 conjugates could be subtly fine tuned, and ultimately completely eliminated, by base substitution using both natural as well as non-natural bases. The level of background correlated directly to the DNA/RNA affinity of the PNAs of the conjugates. This was surprising, as the conjugates have a molecular weight around 500 kDa, and the changes in the PNAs necessary to bring about strongly reduced background in some cases were as little as one D to A substitution (thus removing one potentially hydrogen bonding amino group) or one G to $G_s$ substitution (introducing a single carbonyl to thiocarbonyl change).

TABLE 21

Non-specific staining intensities of due to PNA2 conjugates.

| | Non-specific staining intensity | | |
|---|---|---|---|
| PNA2 | 0.2 μM PNA2 | 0.05 μM PNA2 | Sequence |
| D12120 | 3 | 3 | TCD DGG TAC A |
| D13106 | 2.5 | 1 | TCA AGG TAC A |
| D13148 | 1.5 | 0 | TCA $AG_SG_S$ TAC A |
| D13155 | 2 | 0 | TCD $DG_SG_S$ TAC A |
| D14133 | 0.5 | 0 | TCD DH TAC A |
| D13122 | 3 | 2 | CTA AGG TCA A |
| D13159 | 0 | 0 | CTA $AG_SG_S$ TCA A |
| D14086 | 3 | 2.5 | $U_SCG_S$ $G_SDDTU_S$DGDC |
| D14089 | 0 | 0 | $CU_SG_S$ $G_SDD$ $TU_SD$ $G_SDC$ |
| D14110 | 1 | 0 | DGT $CG_SD$ $DG_SG$ $U_SCU_S$ |
| D14114 | 0 | 0 | $DG_ST$ $CG_SD$ $DG_SG$ $U_SCU_S$ |

Example 33

Use of Fluorescein as a Molecular Label

Tonsil tissues were taken through the steps 1-4, 6-8, 10, and 13 (PNA2 was conjugated with fluorescein) and 16 (the slides were mounted with Vectashield containing DAPI). The concentration used for the conjugates was 0.08 μM for PNA1, D13171 and 0.02, 0.05, 0.1, and 0.2 μM for PNA2, D14008 (TCD $DG_SG_S$TAC A). The slides were evaluated using a fluorescence microscope at 40× and 100× magnifications.

The specific staining was satisfactory. This experiment demonstrated the possibility of making PNA-fluorescein conjugates and illustrated the application of the present invention with a fluorescein as detectable label.

Example 34

Test of a PNA Pair with 10 Antibodies

A multi-block containing tissue from mammalian carcinoma, kidney, colon and two tonsils was taken through the steps 3-4, 6-8, 10, 13-17. In step 8, ten different primary antibodies and a negative control mouse IgG1 were used. (See table 22.) The concentration of the conjugates used was 0.08 µM for PNA1, D12102 and 0.05 µM for PNA2, D12094. Visualization of primary reagents by the K5007 detection kit was performed in parallel according to the manufacturer's instructions. Two primary antibodies targeting membranous targets were used: Monoclonal Mouse Anti-Human CD20cy (DakoCytomation code No. M0755) and Monoclonal Mouse Anti-Human Epithelial Membrane Antigen (DakoCytomation code No. M0613). Five primary antibodies targeting cytoplasmic targets were used: Monoclonal Mouse Anti-Human Cytokeratin (DakoCytomation code No. M3515), Monoclonal Mouse Anti-Human Desmin (DakoCytomation code No. M0760), Monoclonal Mouse Anti-Human CD68 (DakoCytomation code No. M0876), Monoclonal Mouse Anti-Human BCL2 (DakoCytomation code No. 0887) and Monoclonal Mouse Anti-Human CD45 LCA (DakoCytomation code No. M0701). Three primary antibodies targeting nuclear targets were used: Monoclonal Mouse Anti-Human Estrogen Receptor (DakoCytomation code No. M7047), Monoclonal Mouse Anti-Human Ki-67 Antigen (DakoCytomation code No. M7240) and Monoclonal Mouse Anti-Human p27 (DakoCytomation code No. M7203). The primary antibodies, all products from DakoCytomation, were diluted in S2022 as indicated in Table 22.

This example shows the extended use of the PNA system employing several primary antibodies. Furthermore, in the majority of cases using the 10 primary antibodies, visualization by the PNA based detection system demonstrated an improved staining as compared to the reference K5007.

TABLE 22

Comparison of the PNA based detection system with EnVision ™

| Primary Antibody | Antibody Dilution | Specific staining intensity | |
|---|---|---|---|
| | | The PNA system | The K5007 reference |
| M3515 | 1:900 | 2 | 1.5 |
| M0876 | 1:800 | 2 | 2 |
| M0887 | 1:500 | 2 | 2 |
| M0760 | 1:1200 | 1.5 | 1.5 |
| M0701 | 1:1600 | 3 | 2 |
| M0755 | 1:8000 | 1.5 | 1.5 |
| M0613 | 1:6400 | 2.5 | 1.5 |
| M7047 | 1:200 | 3 | 2.5 |
| M7240 | 1:1200 | 2 | 1.5 |
| M7203 | 1:400 | 2.5 | 1.5 |

Example 35

Standard Synthesis of AP-DexVS70-PNA Conjugate

Alkaline Phosphatase ("AP") (from Calf intestine, EIA grade) was dialyzed overnight against 2 mM HEPES, pH 7.2; 0.1 M NaCl; 0.02 mM $ZnCl_2$. Dextran (molecular weight 70 kDa) was activated with divinylsulfone to a degree of 92 reactive groups per dextran polymer (DexVS70).

The three components below were mixed together and placed in a water bath at 40°C. for 30 minutes.

| 192.0 µL DexVS70 | 13.7 nmol |
|---|---|
| 41.0 µL PNA | 41 nmol PNA dissolved in $H_2O$ |
| 6.0 µL 1M $NaHCO_3$ | |

108.0 µL of the DexVS70-PNA conjugate was taken out and added to a mixture of:

| 160.0 µL AP | 43.4 nmol |
|---|---|
| 7.7 µL 1M $NaHCO_3$ | |
| 30.6 µL 20 mM Hepes, pH 7.2; 1M NaCl; 50 mM $MgCl_2$; | |
| 1 mM $ZnCl_2$ | |

The mixture was placed in a water bath at 40° C. for 3 hours. Quenching was performed by adding 30.6 µL of 0.1 M ethanolamine and letting the mixture stand for 30 minutes in water bath at 40° C. The product was purified on FPLC with: Column Superdex-200, buffer: 2 mM HEPES, pH 7.2; 0.1 M NaCl; 5 mM $MgCl_2$; 0.1 mM $ZnCl_2$. Two fractions were collected, one with the product and one with the residue.

In comparison to the experiment described above, another conjugate was made with extended conjugation time. The three components below were mixed together and placed in a water bath at 40° C. for 30 minutes.

| 192.0 µL DexVS70 | 13.7 nmol |
|---|---|
| 41.0 µL PNA | 41 nmol PNA dissolved in $H_2O$ |
| 6.0 µL 1M $NaHCO_3$ | |

108.0 µL of the DexVS70-PNA conjugate was taken out and added to a mixture of:

| 160.0 µL AP | 43.4 nmol |
|---|---|
| 7.7 µL 1M $NaHCO_3$ | |
| 30.6 µL 20 mM Hepes, pH 7.2; 1M NaCl; 50 mM $MgCl_2$; | |
| 1 mM $ZnCl_2$ | |

The mixture was placed in a water bath at 40° C. for 5 hours. Quenching was performed by adding 30.6 µL 0.1 M Ethanolamine and letting the mixture stand for 30 minutes in water bath at 40° C. Purification of the product on FPLC: Column Superdex-200, buffer: 2 mM Hepes, pH 7.2; 0.1 M NaCl; 5 mM $MgCl_2$; 0.1 mM $ZnCl_2$. Two fractions were collected: One with the product and one with the residue.

Relative absorbance PNA(Flu) ($\epsilon_{500nm}$=73000$M^{-1}$) and AP($\epsilon_{278nm}$=140000$M^{-1}$. Corrected for absorbance from PNA at 278 nm, this correction factor is due to the specific PNA and it is calculated: 278/500 nm) was used to calculate the average conjugation ratio of PNA, AP and DexVS70

AP-DexVS70-PNA, 3 hrs:

PNA/DexVS70:1.8

AP/DexVS70:1.8

AP-DexVS70-PNA, 5 hrs:

PNA/DexVS70:2.0

AP/DexVS70:2.4

Due to these results, it is recommended to follow a procedure in which the conjugation time (AP+DexVS70-PNA) is 5 hours.

Example 36

Synthesis and IHC Testing of an Antibody-PNA Conjugate

Part A. Testing Different Ratios of Linker to Antibody

Materials: Antibody: CD 45 dialized overnight against 0.01 M Hepes 0.1 M NaCl pH=7.2. SMCC: Succinimidyl-4 (N-maleimidomethy!) cyclohexan-1-carboxylate molw. 334.33. PNA: Acetyl-$L_{30}$-GTP-TAA-TTP-PAG-$L_{150}$-Lys (Cys)

Test 1

10 nmol CD45 was dissolved in 161 µL 0.01 M Hepes 0.1 M NaCl pH=7.2. 250 nmol SMCC was dissolved in 8 µL NMP. The above components were mixed and placed in a water bath at 30° C. for 60 minutes. The mixture was purified on a mini-prep column (Sephadex G-25) with 0.01 M Hepes 0.1 M NaCl pH=7.2 as eluent. Fractions of 0.3 mL. By measuring absorbance at 278 nm three fractions containing the product (58%) were identified. These three fractions were added to 100 nmol of a lyophilised PNA. Then 1 µL 5% Di-Sodium-EDTA/water was added and the solution was mixed until dissolved and placed in a water bath at 30° C. for 30 minutes. Quenching was performed by adding 2 mg of Cysteine. Water bath 30° C. for 30 minutes.

The product was purified on FPLC: Column SUPERDEX®-75, Buffer 0.01 M Hepes 0.1 M NaCl pH 7.2. The fraction with the product was collected. Relative absorbance between PNA ($\epsilon_{260nm}$) and antibody ($\epsilon_{278nm}$) was used to calculate the average conjugation ratio of PNA and antibody. PNA/CD45:5.2. Yield 39% based on antibody.

Test 2

10 nmol CD45 was dissolved in 161 µL 0.01 IVI Hepes 0.1 M NaCl pH=7.2. 150 nmol SMCC was dissolved in 5 µL NMP. The above components were mixed and placed in a water bath at 30° C. for 60 minutes. The mixture was purified on a mini-prep column (SEPHADEX® G-25) with 0.01 M Hepes 0.1 M NaCl pH=7.2 as eluent Fractions of 0.3 mL. By measuring absorbance at 278 nm three fractions containing the product (74%) were Identified.

These three fractions were added to 100 nmol of a lyophilized PNA. Then 1 µL 5% Di-Sodium-EDTA/water was added and the solution was mixed until dissolved and placed in a water bath at 30° C. for 30 minutes. Quenching was performed by adding 2 mg of cysteine. Water bath 30° C. for 30 minutes.

The product was purified on FPLC: Column Superdex-75, Buffer 0.01 M Hepes 0.1 M NaCl pH 7.2. The fraction with the product was collected. Relative absorbance between PNA ($\epsilon_{260nm}$) and antibody ($\epsilon_{278nm}$) was used to calculate the average conjugation ratio of PNA and antibody. PNA/CD45:3.4. Yield 55% based on antibody.

IHC Test of Conjugates

A later IHC test showed that PNA/CD45 in Test 2 gave a higher score than the one in Test 1. This brought us to the conclusion that the ratio between CD45/SMCC/PNA should be 10/150/100.

Part B. Test of Different Conjugation Times—Antibody and Linker

Materials: Antibody: GAM (goat-anti-mouse) dialysed overnight against 0.1 M NaCl. SMCC: Succinimidyl-4(N-maieimidomethyl)cyclohexan-1-carboxylate moiw. 334.33. Flu-Link: Flu-$L_{90}$-Lys(Flu)-$L_{30}$-Lys(Cys)

Test 1

20 nmol GAM was dissolved in 402 µL 0.01 M Hepes 0.1 M NaCl pH=7.2. 400 nmol SMCC dissolved in 13 µL NMP. The above components were mixed and placed in a water bath at 3.0° C. for 1 hour. 207 µL of the mixture was purified on a mini-prep column (SEPHADEX® G-25) with 0.01 M Hepes 0.1 M NaCl pH=7.2 as eluent. Fractions of 0.3 mL were taken. By measuring absorbance at 278 nm, three fractions containing the product (79%) were identified. These three fractions were added to 200 nmol of a lyophilized Flu-Link. Then 1 µL 5% di-sodium-EDTA/water was added and the solution was mixed until dissolved and placed in a water bath at 30° C. overnight. Quenching was performed by adding 2 mg of Cysteine. Water bath 30° C. for 30 minutes.

The product was purified on FPLC: Column SUPERDEX®-75, Buffer 0.01 M Hepes 0.1 M NaCl pH 7.2. The fraction with the product was collected. Relative absorbance between Flu-Link (s498 nm) and antibody ($s_2$78 nm) was used to calculate the average conjugation ratio of PNA and antibody. Flu-Link/GAM: 7.1. Yield 55% based on antibody.

Test 2

20 nmol GAM was diluted with 402 µL 0.01 M Hepes 0.1 M NaCl pH=7.2, 400 nmol SMCC was dissolved in 13 µL NMP. The above components were mixed and placed in a water bath at 30° C. for 2 hours. The rest of the synthesis and purification was done in exactly the same procedure as for 1 hour. There was a 64% yield of GAM/SMCC before adding the Flu-Link. Flu-Link/GAM: 8.7. Yield 33% based on antibody.

Part C. Test of Different Conjugation Times—Fluorophore and Linker

Materials: Antibody: GAM dialysed overnight against 0.1 M NaCl. SMCC: Succinimidyl-4(N-maleimidomethyl)cyclohexan-1-carboxylate molw. 334.33. Flu-Link: Flu-$L_{90}$-Lys(Flu)-$L_{30}$-Lys(Cys)

Test 1

20 nmol GAM was dissolved 378 µL 0.01 M Hepes 0.1 M NaCl pH=7.2. 400 nmol SMCC was dissolved in 13 µL NMP. The above components were mixed and placed in a water bath at 30° C. for 1 hour. The mixture was divided in two and purified on two mini-prep columns (SEPHADEX® G-25) with 0.01 M Hepes 0.1 M NaCl pH=7.2 as eluent. Fractions of 0.3 mL were taken. By measuring absorbance at 278 nm, three fractions from each column containing the product (76% in all) were identified. These six fractions were pooled, divided in two, and each added to 200 nmol of a lyophilized Flu-Link. Then 1 µL 5% di-sodium-EDTA/water was added and the solution was mixed until dissolved and placed in a water bath at 30° C., one for 30 minutes, the other for 60 minutes. Quenching was performed by adding 2 mg of cysteine. Water bath 30° C. for 30 minutes.

The product was purified on FPLC: Column SUPERDEXe-75, Buffer 0.01 M Hepes 0.1 M NaCl pH 7.2. The fractions with the product from each purification were collected. Relative absorbance between Flu-Link ($\epsilon_{498nm}$) and antibody ($\epsilon_{278nm}$) was used to calculate the average conjugation ratio of PNA and antibody. 30 minutes conjugation Flu-Link/GAM: 7.0 Yield 55% based on antibody. 60 minutes conjugation Flu-Link/GAM: 6.9 Yield 52% based on antibody. The above results show that 30 minutes conjugation between GAM/SMCC and Flu-Link is sufficient.

Example 37

Additional Teats of 2 and 3 Layer Visualization Systems

Primary mouse antibody M7240 (Dako) targeting MIB-1 was diluted to final 1:150 in S2022 buffer (Dako) and applied on a multi tissue section. Following 10 minutes incubation at RT the section was washed 5 minutes using 10× diluted S3006 buffer (Dako).

Goat-anti-mouse secondary antibody conjugated with dextran and a first PNA sequence (GaM-dex-PNA1 (218-117)) was diluted to final concentration of 0.08 jj,M (based on dextran) in BP-HEPES-buffer (1.5% BSA, 3% PEG, 0.15M NaCl, 10 mM HEPES, pH 7.2) and was applied to the section. Following 10 minutes incubation at room temperature (RT), the section was washed 5 minutes using 10× diluted S3006 (Dako). The sections were rinsed in deionized water. Following 10 minutes incubation in 0.5% glutaraldehyde at RT, the sections were rinsed in deionized water and washed 5 minutes using 10× diluted S3006 (Dako).

An adaptor unit comprising dextran coupled to two different PNA sequences, one complementary to PNA1 above (PNA2) and another not complementary to PNA1 (PNA3), called PNA2-dex-PNA3 (218-057) was diluted to a final concentration of 0.05 µM (dextran) in BP-HEPES-buffer (1.5% BSA, 3% PEG, 0.15M NaCl, 10 mM HEPES, pH 7.2) and was applied to the section. Following 10 minutes incubation at RT, the section was washed 5 minutes using 10× diluted S3006 (Dako). Next, a conjugate of a PNA4, complementary to PNA5 above, dextran, and the detectable label alkaline phosphatase (PNA4-dex-AP (209-177)) was diluted to final concentration of 0.05 µM (dextran) in BAP-HEPES-buffer (1.5% BSA, 3% PEG, 0.15M NaCl, 0.05% 4-aminoantipyrin, 10 mM HEPES, pH 7.2), and was applied. Following 10 minutes incubation at RT, the sections were washed 5 minutes using 10× diluted S3006 (Dako).

Permanent Red working solution (an aqueous Tris buffer with naphthol-phosphate and a diazonium dye; K0640 Dako) was prepared and then applied. Following 10 minutes incubation, the section was washed 5 minutes using 10× diluted S3006 (Dako). Finally the sections were counter stained 5 minutes using haematoxyiin S3301 (Dako), rinsed in deionzed water, washed 3 minutes in wash buffer, and mounted in Faramount S3025 (Dako). Result: MIB-1=1+/0.5+.

Example 38

Primary rabbit antibody A0452 (Dako) targeting CD3 was diluted to final 1:100 in S2022 (Dako) and applied on a multi tissue section. Following 10 minutes incubation at RT the sections were washed 5 minutes using 10× diluted S3006 (Dako).

Then, a goat-anti-rabbit secondary antibody coupled to dextran and a first PNA sequence, PNA2a (GaR-dex-Alexander (209-127)) was diluted to final concentration of 0.08 µM (dextran) in BP-HEPES-buffer (1.5% BSA, 3% PEG, 0.15M NaCl, 10 mM HEPES, pH 7.2) and was applied. Following 10 minutes incubation at RT the sections were washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

Next, a complementary PNA coupled to dextran and detectable label alkaline phosphatase (AP) (PNA2b-dex-AP (209-177) was diluted to final concentration of 0.05 µM (dextran) in BAP-HEPES-buffer (1.5% BSA, 3% PEG, 0.15M NaCl, 0.05% 4-aminoantipyrin, 10 mM HEPES, pH 7.2) and was applied. Following 10 minutes incubation at RT the section was washed 5 minutes using 10× diluted S3006 (Dako).

Permanent Red working solution (K0640 Dako) was prepared and was applied. Following 10 minutes incubation the sections were washed 5 minutes using 10× diluted S3006 (Dako). Finally the sections were counter stained 5 minutes using haematoxylin S3301 (Dako), rinsed in deionized water, washed 3 minutes in wash buffer, and mounted in Faramount S3025 (Dako). Result: CD3 specific staining=1.5+ compared to non-specific background staining of 1+. The order of detection affects the staining result.

Example 39

Detecting Two Targets in a Sample

General Procedural Note: Before conducting the detection experiment on formalin-fixed, paraffin-embedded (FPPE) tissue sections, the specimen should be deparaffinized (dewaxed), rehydrated, and blocked for endogenous peroxidase activity. Some specimens should be subjected to target retrieval using heat or enzyme digestion. Following target retrieval, the specimens should be rinsed gently with wash buffer.

Part A. Two-layer Detection Experiment Using Secondary Antibody Probes

In this experiment, a mouse primary antibody was used as a primary binding agent for a specific target in a tissue sample. That antibody was then recognized by a goat-anti-mouse-dextran-PNA conjugate recognition unit. A different primary antibody, a rabbit antibody, was used as a primary binding agent for a different target in the sample. That antibody was recognized by a goat-anti-rabbit-dextran-PNA recognition unit. One reaction was visualized by a PNA-dextran-HRP (horse-radish peroxidase) detection unit and the other reaction was visualized by a PNA-dextran-AP (alkaline phosphatase) detection unit. PNA sequences 1 and 2 and sequences 3 and 4, respectively, specifically hybridize to each other.

Primary mouse antibody M3515 (Dako) targeting Cytokeratin and primary rabbit antibody Z0311 (Dako) targeting S100 were diluted 1:50 and 1:100 in S2022 buffer (Dako), respectively. The antibodies were applied simultaneously on multi tissue sections. Following 10 minutes incubation at RT the sections were washed 5 minutes using 10× diluted S3006 buffer (Dako). Goat-anti-mouse-dextran-PNA1 (GaM-dex-PNA1) and goat-anti-rabbit-dextran-PNA3 (GaR-dex-PNA3) were both diluted to a final concentration of 0.08 µM (dextran) in BP-HEPES-buffer (1.5% BSA, 3% PEG, 0.15M NaCl, 10 mM HEPES, pH 7.2). The two conjugates were applied simultaneously on the sections. Following 10 minutes incubation at room temperature (RT), the sections were washed 5 minutes using 10× diluted S3006 (Dako). The sections were rinsed in deionized water.

The samples were then incubated for 10 minutes in 0.5% glutaraldehyde at RT and then rinsed in deionized water and washed 5 minutes using 10× diluted S3006 (Dako). PNA2-dex-HRP and PNA4-dex-AP were both diluted to final concentration of 0.05 µM (dextran) in BAP-HEPES-buffer (1.5% BSA, 3% PEG, 0.15M NaCl, 0.05% 4-aminoantipyrin, 10 mM HEPES, pH 7.2). The two conjugates were applied simultaneously on the sections. Following 10 minutes incubation at RT the sections were washed 5 minutes using 10× diluted S3006 (Dako). Permanent Red working solution (K0640 Dako) and DAB+ working solution (an aqueous imidazole buffer with hydrogen peroxide and DAB; K3468 Dako) were prepared.

The reactions were detected with one of the following methods. Detection method 1: Permanent Red working solution was applied. Following 10 minutes incubation the sections were washed 5 minutes using 10× diluted S3006

(Dako). Then DAB+ working solution was applied and following 10 minutes incubation the sections were washed 5 minutes using deionized water. Finally the sections were counter stained 5 minutes using haematoxylin S3301 (Dako), rinsed in deionized water, washed 3 minutes in wash buffer, and mounted in Faramount S3025 (Dako).

Detection method 2: DAB+ working solution was applied. Following 10 minutes incubation the sections were washed 5 minutes using 10× diluted S3006 (Dako). Then Permanent Red working solution was applied and following 10 minutes incubation the sections were washed 5 minutes using deionized water. Finally the sections were counter stained 5 minutes using haematoxylin S3301 (Dako), rinsed in deionized water, washed 3 minutes in wash buffer, and mounted in Faramount S3025 (Dako).

Result: Cytokeratin=HRP=3+ specific staining and 0 background staining, S100=AP=3+ specific staining and 0 background staining. The order of detection affects the staining result. If detection method 1 is used then Permanent Red dominates. If detection method 2 is used then DAB+ dominates.

Part B. Two-layer Detection Experiment Using Antibodies as Probes

Primary mouse antibody M3515 (Dako) targeting Cytokeratin and primary rabbit antibody Z0311 (Dako) targeting S100 were diluted to final 1:50 and 1:400 in S2022 (Dako), respectively. The antibody mixture was applied on multitissue sections. Following 10 minutes incubation at RT the sections were washed 5 minutes using 10× diluted S3006 (Dako). GaM-dex-PNA1 (209-149) and GaR-dex-PNA2 (209-127) were both diluted to final concentration of 0.08 µM (dextran) in BP-HEPES-buffer (1.5% BSA, 3% PEG, 0.15M NaCl, 10 mM HEPES, pH 7.2). The two conjugates were applied simultaneously on the sections.

Following 10 minutes incubation at RT the sections were washed 5 minutes using 10× diluted S3006 (Dako). The sections were rinsed in deionized water. Following 10 minutes incubation in 1% glutaraldehyde at RT the sections were rinsed in deionized water and washed 5 minutes using 10× diluted S3006 (Dako). PNA2-dex-HRP (209-157) and PNA4-dex-AP (209-177) were both diluted to final concentration of 0.05 nM/dex in BAP-HEPES-buffer (1.5% BSA, 3% PEG, 0.15M NaCl, 0.05% 4-aminoantipyrin, 10 mM HEPES, pH 7.2). The two conjugates were applied simultaneously on the sections. Following 10 minutes incubation at RT the sections were washed 5 minutes using 10× diluted S3006 (Dako). Permanent Red working solution (K0640 Dako) and DAB+ working solution (K3468 Dako) were prepared.

The reactions were detected with one of the following methods. Detection method 1: Permanent Red working solution was applied. Following 10 minutes incubation the sections were washed 5 minutes using 10× diluted S3006 (Dako). Then DAB+ working solution was applied and following 10 minutes incubation the sections were washed 5 minutes using deionized water. Finally the sections were counter stained 5 minutes using haematoxylin S3301 (Dako), rinsed in deionized water, washed 3 minutes in wash buffer, and mounted in Faramount S3025 (Dako).

Detection method 2: DAB+ working solution was applied. Following 10 minutes incubation the sections were washed 5 minutes using 10× diluted S3006 (Dako). Then Permanent Red working solution was applied and following 10 minutes incubation the sections were washed 5 minutes using deionized water. Finally the sections were counter stained 5 minutes using haematoxylin S3301 (Dako), rinsed in deionized water, washed 3 minutes in wash buffer, and mounted in Faramount S3025 (Dako).

Result: Using detection method 1: Cytokeratin=HRP=2.5+ specific staining and 0 background staining, S100=AP=2.5+ specific staining and 0 background staining. Using detection method 2: Cytokeratin=HRP=3+ specific staining and 0.5+ background staining, S100=AP=3+ specific staining and 0 background staining. The order of detection affects the staining result.

Example 40

Further 2 and 3 Layer Systems for Detection of Multiple Targets Part A. Combined Two and Three-Layer System In this example, a mouse antibody primary binding agent was recognized by a GaM-dex-PNA1 and a rabbit antibody primary binding agent was recognized by GaR-dex-PNA2. One reaction was detected by a PNA-dex-Enzyme1 conjugate and the other by a PNA-dex-PNA adaptor unit and then a PNA-dex-Enzyme2 conjugate. PNA1 recognizes PNA2 while PNA3 recognizes PNA4. The enzymes used were HRP and AP, bringing along respectively a brown and red end-product within the same tissue section. The PNA-dex-PNA adaptor unit adds a third layer to the detection system.

Primary mouse antibody M7240 (Dako) targeting MIB-1 and primary rabbit antibody A0452 (Dako) targeting CD3 were diluted to final 1:150 and 1:100 in S2022 (Dako), respectively. The antibody mixture was applied on multi tissue sections. Following 10 minutes incubation at RT the sections were washed 5 minutes using 10× diluted S3006 (Dako).

GaM-dex-PNA1 (218-117) and GaR-dex-PNA3 (209-127) were both diluted to final concentration of 0.08 µM (dextran) in BP-HEPES-buffer (1.5% BSA, 3% PEG, 0.15M NaCl, 10 mM HEPES, pH 7.2). The two conjugates were applied simultaneously on the sections. Following 10 minutes incubation at RT the sections were washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

PNA4-dex-HRP (218-021) was diluted to final concentration of 0.05 µM (dextran) in BAP-HEPES-buffer (1.5% BSA, 3% PEG, 0.15M NaCl, 0.05% 4-aminoantipyrin, 10 mM HEPES, pH 7.2) and applied on the sections. Following 10 minutes incubation at RT the sections were washed 5 minutes using 10× diluted S3006 (Dako). PNA2-dex-PNA3 (218-057) amplification unit was diluted to final concentration of 0.05 µM (dextran) in BP-HEPES-buffer (1.5% BSA, 3% PEG, 0.15M NaCl, 10 mM HEPES, pH 7.2) and applied on the sections. Following 10 minutes incubation at RT the sections were washed 5 minutes using 10× diluted S3006 (Dako). PNA4-dex-AP (209-177) was diluted to final concentration of 0.05 µM/dex in BAP-HEPES-buffer (1.5% BSA, 3% PEG, 0.15M NaCl, 0.05% 4-aminoantipyrin, 10 mM HEPES, pH 7.2) and applied on the sections. Following 10 minutes incubation at RT the sections were washed 5 minutes using 10× diluted S3006 (Dako). Permanent Red working solution (K0640 Dako) and DAB+ working solution (K3468 Dako) were prepared.

The reactions were detected with one of the following methods. Detection method 1: Permanent Red working solution was applied. Following 10 minutes incubation the sections were washed 5 minutes using 10× diluted S3006

(Dako). Then DAB+ working solution was applied and following 10 minutes incubation the sections were washed 5 minutes using deionized water. Finally the sections were counter stained 5 minutes using haematoxylin S3301 (Dako), rinsed in deionized water, washed 3 minutes in wash buffer, and mounted in Faramount S3025 (Dako).

Detection method 2: DAB+ working solution was applied. Following 10 minutes incubation the sections were washed 5 minutes using 10× diluted S3006 (Dako). Then Permanent Red working solution was applied and following 10 minutes incubation the sections were washed 5 minutes using deionized water. Finally the sections were counter stained 5 minutes using haematoxylin S3301 (Dako), rinsed in deionized water, washed 3 minutes in wash buffer, and mounted in Faramount S3025 (Dako).

Result: CD3=2-layer experiment=HRP=3+ specific and 0 background staining, MIB-1=3-layer experiment=AP=2+ specific and 1.5+ background staining. The order of detection affects the staining result.

Part B.

Primary mouse antibody M7240 (Dako) targeting MIB-1 and primary rabbit antibody A0452 (Dako) targeting CD3 were diluted to final 1:150 and 1:100 in S2022 (Dako), respectively. The antibody mixture was applied on multi tissue sections. Following 10 minutes incubation at RT the sections were washed 5 minutes using 10× diluted S3006 (Dako).

GaM-dex-PNA1 (218-117) and GaR-dex-PNA3 (209-127) were both diluted to final concentration of 0.08 µM (dextran) in BP-HEPES-buffer (1.5% BSA, 3% PEG, 0.15M NaCl, 10 mM HEPES, pH 7.2). The two conjugates were applied simultaneously on the sections. Following 10 minutes incubation at RT the sections were washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

PNA4-dex-AP (209-177) was diluted to final concentration of 0.05 p.M (dextran) in BAP-HEPES-buffer (1.5% BSA, 3% PEG, 0.15M NaCl, 0.05% 4-aminoantipyrin, 10 mM HEPES, pH 7.2) and applied on the sections. Following 10 minutes incubation at RT the sections were washed 5 minutes using 10× diluted S3006 (Dako). PNA2-dex-PNA3 (218-057) was diluted to final concentration of O.OSjiM (dextran) in BP-HEPES-buffer (1.5% BSA, 3% PEG, 0.15M NaCl, 10 mM$_N$ HEPES, pH 7.2) and applied on the sections. Following 10 minutes incubation at RT the sections were washed 5 minutes using 10× diluted S3006 (Dako).

PNA4-dex-HRP (218-021) was diluted to final concentration of 0.05 µM (dextran) in BAP-HEPES-buffer (1.5% BSA, 3% PEG, 0.15M NaCl, 0.05% 4-aminoantipyrin, 10 mM HEPES, pH 7.2) and applied on the sections. Following 10 minutes incubation at RT the sections were washed 5 minutes using 10× diluted S3006 (Dako).

Permanent Red working solution (K0640 Dako) and DAB+ working solution (K3468 Dako) were prepared. The reactions were detected with one of the following methods. Detection method 1: Permanent Red working solution was applied. Following 10 minutes incubation the sections were washed 5 minutes using 10× diluted S3006 (Dako). Then DAB+ working solution was applied and following 10 minutes incubation the sections were washed 5 minutes using deionized water. Finally the sections were counter stained 5 minutes using haematoxylin S3301 (Dako), rinsed in deionzed water, washed 3 minutes in wash buffer, and mounted in Faramount S3025 (Dako).

Detection method 2: DAB+ working solution was applied. Following 10 minutes incubation the sections were washed 5 minutes using 10× diluted S3006 (Dako). Then Permanent Red working solution was applied and following 10 minutes incubation the sections were washed 5 minutes using deionized water. Finally the sections were counter stained 5 minutes using haematoxylin S3301 (Dako), rinsed in deionized water, washed 3 minutes in wash buffer, and mounted in Faramount S3025 (Dako).

Result: Using detection method 1: CD3=2-layer experiment=AP=2+ specific and 0 non-specific, background staining, MIB-1=3-layer experiment=HRP=1.5+ specific and 0 background staining. Using detection method 2: CD3=2-layer experiment=AP=3+ specific and 1.5+ nonspecific staining, MIB-1=3-layer experiment=HRP=1.5+ specific and 1+ background staining. The order of detection affects the staining result.

Example 41

Further Multi-target Detection Experiment

This example presents a 2-layer detection of two targets in which mouse-Ab-dex-PNA is recognized by PNA-dex-Enzyme1 and rabbit-Ab-dex-PNA is recognized by PNA-dex-Enzyme2. The enzymes are HRP and AP bringing along respectively a brown and red end-product within the same tissue section. As in preceding examples, PNA1 and 2 specifically hybridize, as do PNA3 and 4.

CD3-dex-PNA1 (D16043) and MIB-1-dex-PNA2 (218-097) were both diluted to final concentration of 0.1 µM (dextran) in BP-HEPES-buffer (1.5% BSA, 3% PEG, 0.15M NaCl, 10 mM HEPES, pH 7.2). The two conjugates were applied simultaneously on the sections. Following 10 minutes incubation at RT the sections were washed 5 minutes using 10× diluted S3006 (Dako).

PNA2-dex-HRP (209-141) and PNA4-dex-AP (209-177) were diluted to final concentration of 0.2 µM (dextran) and 0.05 µM (dextran) in BAP-HEPES-buffer (1.5% BSA, 3% PEG, 0.15M NaCl, 0.05% 4-aminoantipyrin, 10 mM HEPES, pH 7.2), respectively. The two conjugates were applied simultaneously on the sections. Following 10 minutes incubation at RT the sections were washed 5 minutes using 10× diluted S3006 (Dako). Permanent Red working solution (K0640 Dako) and DAB+ working solution (K3468 Dako) were prepared.

The reactions were detected with one of the following methods. Detection method 1: Permanent Red working solution was applied. Following 10 minutes incubation the sections were washed 5 minutes using 10× diluted S3006 (Dako). Then DAB+ working solution was applied and following 10 minutes incubation the sections were washed 5 minutes using deionized water. Finally the sections were counter stained 5 minutes using haematoxylin S3301 (Dako), rinsed in deionzed water, washed 3 minutes in wash buffer, and mounted in Faramount S3025 (Dako).

Detection method 2: DAB+ working solution was applied. Following 10 minutes incubation the sections were washed 5 minutes using 10× diluted S3006 (Dako). Then Permanent Red working solution was applied and following 10 minutes incubation the sections were washed 5 minutes using deionized water. Finally the sections were counter stained 5 minutes using haematoxylin S3301 (Dako), rinsed in deionzed water, washed 3 minutes in wash buffer, and mounted in Faramount S3025 (Dako).

Result: Using detection method 1: CD3=HRP=2+ specific and 0 nonspecific, background staining, MIB-1=AP=3+ specific and 0 background staining. Using detection method 2: CD3=HRP=2+ specific and 0.5+ background staining, MIB-1=AP=2.5+ specific and 0 background staining. The order of detection affects the staining result.

Example 42

3-Layer Detection System for Detecting MIB-1 Primary Mouse Antibody

Aim. To show that the MIB-1 primary mouse antibody can be detected in a 3-layer system.

Experimental Steps: Primary mouse antibody M7240 (Dako) targeting MIB-1 was diluted to a final 1:150 in S2022 buffer (Dako) and applied on a multi tissue section. Following 10 minutes incubation at RT the section was washed 5 minutes using 10× diluted S3006 (Dako). GaM-dex-PNA1 was diluted to a final concentration of 0.08 p.M (dextran) in BP-HEPES-buffer (1.5% BSA, 3% PEG, 0.15M NaCl, 10 mM HEPES, pH 7.2) and was applied. Following 10 minutes incubation at RT the section was washed 5 minutes using 10× diluted S3006 buffer (Dako). The sections were rinsed in deionized water.

Following 10 minutes incubation in 0.5% glutaraldehyde at RT the sections were rinsed in deionized water and washed 5 minutes using 10× diluted S3006 (Dako). PNA2-dex-PNA3 was diluted to a final concentration of 0.05 µM (dextran) in BP-HEPES-buffer (1.5% BSA, 3% PEG, 0.15M NaCl, 10 mM HEPES, pH 7.2) and was applied. (PNA2 hybridizes to PNA1 while PNA3 hybridizes to PNA4.) Following 10 minutes incubation at RT the section was washed 5 minutes using 10× diluted S3006 (Dako).

PNA4-dex-HRP was diluted to final concentration of 0.05 µM (dextran) in BAP-HEPES-buffer (1.5% BSA, 3% PEG, 0.15M NaCl, 0.05% 4-aminoantipyrin, 10 mM HEPES, pH 7.2) and was applied. Following 10 minutes incubation at RT the sections were washed 5 minutes using 10× diluted S3006 (Dako).

Prepared DAB+ working solution (Dako K3468) was applied. Following 10 minutes incubation the sections were washed 5 minutes deionized water. Finally the sections were counter stained 5 minutes using haematoxylin S3301 (Dako), rinsed in deionized water, washed 3 minutes in wash buffer, and mounted in Faramount S3025 (Dako).

Result: The brown end product of the HRP reaction visualize the specific nuclear MIB-1 staining of proliferating cells. Staining intensity score 2.5+ and background score 1+.

Example 43

2-Layer IHC Detection Test Comparing Orientation of PNA Hybridization

Aim: To use 2-layer HRP detection to test and compare GaM-dex-PNA1+PNA2-dex-HRP and GaM-dex-PNA2+PNA1-dex-HRP.

| Unit No. GaM-dex-PNA | Unit No. PNA-dex-HRP | Specific score | Background score |
|---|---|---|---|
| 218-117 | 209-141 | 1.5+ | 0 |
| 218-163 | 218-121 | 0.5+ | 0 |

Experimental Steps: Primary mouse antibody M3515 (Dako) targeting CK was diluted to final 1:200 in S2022 (Dako) and applied on a multi tissue section. Following 10 minutes incubation at RT the section was washed 5 minutes using 10× diluted S3006 (Dako). GaM-dex-PNA (218-117 or 218-163) was diluted to final concentration of 0.08 µM/dex in BP-HEPES-buffer (1.5% BSA, 3% PEG, 0.15M NaCl, 10 mM HEPES, pH 7.2) and was applied. Following 10 minutes incubation at RT the section was washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

PNA-dex-HRP (209-141 or 218-121) was diluted to final concentration of 0.05 |uM/dex in BAP-HEPES-buffer (1.5% BSA, 3% PEG, 0.15M NaCl, 0.05% 4-aminoantipyrin, 10 mM HEPES, pH 7.2) and was applied. Following 10 minutes incubation at RT the sections were washed 5 minutes using 10× diluted S3006 (Dako).

Prepared DAB+ working solution (Dako K3468) was applied. Following 10 minutes incubation the sections were washed 5 minutes deionized water. Finally the sections were counter stained 5 minutes using haematoxylin S3301 (Dako), rinsed in deionzed water, washed 3 minutes in wash buffer, and mounted in Faramount S3025 (Dako).

Result: The brown end product of the HRP reaction visualize the specific cytokeratin staining of epithelia cells and show that performance depend on which one of the PNA sequences from a PNA pair were used when composing the recognition and detection unit.

Example 44

2-Layer IHC Testing of Recognition Units with Different Linker Length

Aim To use 2-layer HRP detection to test and compare recognition units with different linker length (L150, L300, L540).

| Unit No. | Linker length | Specific score | Background score |
|---|---|---|---|
| 209-033 | L150 | 2.5+ | 1+ |
| 209-029 | L300 | 2.5+ | 1+ |
| 195-147 | L540 | 2+ | 0 |

Experimental Steps: Primary mouse antibody M3515 (Dako) targeting CK was diluted to final 1:200 in S2022 (Dako) and applied on a multi tissue section. Following 10 minutes incubation at RT the section was washed 5 minutes using 10× diluted S3006 (Dako).

GaM-dex-PNA1 (209-033, 209-029, or 195-147) was diluted to a final concentration of 0.08 µM/dex in BP-HEPES-buffer (1.5% BSA, 3% PEG, 0.15M NaCl, 10 mM HEPES, pH 7.2) and was applied. Following 10 minutes incubation at RT the section was washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

PNA2-dex-HRP (209-041) was diluted to final concentration of 0.05 p.M/dex in BAP-HEPES-buffer (1.5% BSA, 3% PEG, 0.15M NaCl, 0.05% 4-aminoantipyrin, 10 mM HEPES, pH 7.2) and was applied. Following 10 minutes incubation at RT the sections were washed 5 minutes using 10× diluted S3006 (Dako).

Prepared DAB+ working solution (Dako K3468) was applied. Following 10 minutes incubation the sections were washed 5 minutes deionized water. Finally the sections were counter stained 5 minutes using haematoxylin S3301 (Dako), rinsed in deionized water, washed 3 minutes in wash buffer, and mounted in Faramount S3025 (Dako).

Result: The brown end product of the HRP reaction visualize the specific cytokeratin staining of epithelia cells and show no significant difference in performance when comparing recognition units having different linker length.

Example 45

2-Layer IHC Testing of Recognition Units with Different Dextran Size

Aim: To use 2-layer HRP detection to test and compare recognition units with different dextran size (dex70 and dex150).

| Unit No. | Dextran size | Specific score | Background score |
|---|---|---|---|
| 195-147 | Dex70 | 2+ | 0 |
| 195-151 | Dex150 | 2+ | 1+ |

Experimental Steps: Primary mouse antibody M3515 (Dako) targeting CK was diluted to final 1:200 in S2022 (Dako) and applied on a multi tissue section. Following 10 minutes incubation at RT the section was washed 5 minutes using 10× diluted S3006 (Dako).

GaM-dex-PNA1 (195-147 or 195-151) was diluted to final concentration of 0.08 μM/dex in BP-HEPES-buffer (1.5% BSA, 3% PEG, 0.15M NaCl, 10 mM HEPES, pH 7.2) and was applied. Following 10 minutes incubation at RT the section was washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

PNA2-dex-HRP (209-041) diluted to final concentration of 0.05 μM/dex in BAP-HEPES-buffer (1.5% BSA, 3% PEG, 0.15M NaCl, 0.05% 4-aminoantipyrin, 10 mM HEPES, pH 7.2) was applied. Following 10 minutes incubation at RT the sections were washed 5 minutes using 10× diluted S3006 (Dako).

Prepared DAB+ working solution (Dako K3468) was applied. Following 10 minutes incubation the sections were washed 5 minutes deionized water. Finally the sections were counter stained 5 minutes using haematoxylin S3301 (Dako), rinsed in deionzed water, washed 3 minutes in wash buffer, and mounted in Faramount S3025 (Dako).

Result: The brown end product of the HRP reaction visualize the specific cytokeratin staining of epithelia cells and show no significant difference in performance when comparing recognition units having different dextran size.

Example 46

2-Layer IHC Testing of Recognition Units with Different Number of Linker-PNA Attached Aim: To use 2-layer HRP detection to test and compare detection units with different number of PNA per dextran (0.8 PNA/dex and 1.5 PNA/dex).

| Unit No. | PNA/dex | Specific score | Background score |
|---|---|---|---|
| 195-051 | 0.8 | 3+ | 0.5+ |
| D15008 | 1.5 | 3+ | 0.5+ |

Experimental Steps: Primary mouse antibody M3515 (Dako) targeting CK was diluted to final 1:200 in S2022 (Dako) and applied on a multi tissue section. Following 10 minutes incubation at RT the section was washed 5 minutes using 10× diluted S3006 (Dako).

GaM-dex-PNA1 (195-047) diluted to final concentration of 0.08 μM/dex in BP-HEPES-buffer (1.5% BSA, 3% PEG, 0.15M NaCl, 10 mM HEPES, pH 7.2) was applied. Following 10 minutes incubation at RT the section was washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

PNA2-dex-HRP (195-051 or D15008) diluted to final concentration of 0.05 μM/dex in BAP-HEPES-buffer (1.5% BSA, 3% PEG, 0.15M NaCl, 0.05% 4-aminoantipyrin, 10 mM HEPES, pH 7.2) was applied. Following 10 minutes incubation at RT the sections were washed 5 minutes using 10× diluted S3006 (Dako).

Prepared DAB+ working solution (Dako K3468) was applied. Following 10 minutes incubation the sections were washed 5 minutes deionized water. Finally the sections were counter stained 5 minutes using haematoxylin S3301 (Dako), rinsed in deionzed water, washed 3 minutes in wash buffer, and mounted in Faramount S3025 (Dako).

Result: The brown end product of the HRP reaction visualize the specific cytokeratin staining of epithelia cells and show no significant difference in performance when comparing detection units having different number of PNA/dex.

Example 47

2-Layer IHC Testing Comparing Recognition and Detection Unitshaving "Linker-PNA" or "Linker-PNA-linker Tail" Attached Aim: To use 2-layer HRP detection to test and compare recognition and detection units having PNA sequences without and with "linker tail".

| Unit No. GaM-dex-PNA | tail | Unit No. PNA-dex-HRP | tail | Specific score | Background score |
|---|---|---|---|---|---|
| 218-113 | No | 218-021 | No | 3+ | 1+ |
| D16074 | Yes | 218-021 | No | 3+ | 0.5+ |
| 218-113 | No | D16076 | Yes | 3+ | 0.5+ |
| D16074 | Yes | D16076 | Yes | 4+ | 1.5+ |

Experimental Steps: Primary mouse antibody M3515 (Dako) targeting CK was diluted to final 1:200 in S2022 (Dako) and applied on a multi tissue section. Following 10 minutes incubation at RT the section was washed 5 minutes using 10× diluted S3006 (Dako). GaM-dex-PNA (218-113 or D16074) diluted to final concentration of 0.08 jˆM/dex in BP-HEPES-buffer (1.5% BSA, 3% PEG, 0.15M NaCl, 10 mM HEPES, pH 7.2) was applied. Following 10 minutes incubation at RT the section was washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

PNA-dex-HRP (218-021 or D16076) diluted to final concentration of 0.05 p.M/dex in BAP-HEPES-buffer (1.5% BSA, 3% PEG, 0.15M NaCl, 0.05% 4-aminoantipyrin, 10 mM HEPES, pH 7.2) was applied. Following 10 minutes incubation at RT the sections were washed 5 minutes using 10× diluted S3006 (Dako).

Prepared DAB+ working solution (Dako K3468) was applied. Following 10 minutes incubation the sections were washed 5 minutes deionized water. Finally the sections were counter stained 5 minutes using haematoxylin S3301 (Dako), rinsed in deionzed water, washed 3 minutes in wash buffer, and mounted in Faramount S3025 (Dako).

Result: The brown end product of the HRP reaction visualize the specific cytokeratin staining of epithelia cells and show that performance depend on the presence of a "linker tail" on the PNA sequence. A "linker-tail" on the PNA sequence may influence both specific score and background score.

Example 48

2-Layer IHC Testing Comparing Recognition and Detection Units Having "Linker-PNA" or "Linker-PNA-charge" Attached Aim: To use 2-layer HRP detection to test and compare recognition and detection units having PNA sequences without and with charge.

| Unit No. GaM-dex-PNA | charge | Unit No. PNA-dex-HRP | charge | Specific score | Background score |
|---|---|---|---|---|---|
| D15078 | No | D15069 | No | 0.5+ | 0 |
| 209-149 | Yes | 209-157 | Yes | 3+ | 1+ |

Experimental Steps: Primary mouse antibody M3515 (Dako) targeting CK was diluted to final 1:200 in S2022 (Dako) and applied on a multi tissue section. Following 10 minutes incubation at RT the section was washed 5 minutes using 10× diluted S3006 (Dako).

GaM-dex-PNA (D15078 or 209-149) diluted to final concentration of 0.08 ^iM/dex in BP-HEPES-buffer (1.5% BSA, 3% PEG, 0.15M NaCl, 10 mM HEPES, pH 7.2) was applied. Following 10 minutes incubation at RT the section was washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

PNA-dex-HRP (D15069 or 209-157) diluted to final concentration of 0.05 µM/dex in BAP-HEPES-buffer (1.5% BSA, 3% PEG, 0.15M NaCl, 0.05% 4-aminoantipyrin, 10 mM HEPES, pH 7.2) was applied. Following 10 minutes incubation at RT the sections were washed 5 minutes using 10× diluted S3006 (Dako).

Prepared DAB+ working solution (Dako K3468) was applied. Following 10 minutes incubation the sections were washed 5 minutes deionized water. Finally the sections were counter stained 5 minutes using haematoxylin S3301 (Dako), rinsed in deionzed water, washed 3 minutes in wash buffer, and mounted in Faramount S3025 (Dako).

Result: The brown end product of the HRP reaction visualize the specific cytokeratin staining of epithelia cells and show that performance depend on the presence of charge on the PNA sequence. Charge on the PNA sequences within a PNA pair may influence both specific score and background score.

Example 49

Method of Synthesizing Mono and 2,4-diamino-pyrimidine-5-Yl PNA Monomers 2,4-diamino-pyrimidine-5-yl may be introduced Into DNA-oligomers by methods known in the art (e.g. S. A. Benner et al., *Nucleic Acid Research* 24(7): 1308-1313 (1996)). A corresponding PNA oligomer is prepared by chlorinating pyrimidine-5-acetic acid to yield 2-chloro-pyrimidine-5-acetic acid, 4-chloro-pyrimidine-5-acetic acid, and 2,4-dichloro-pyrimidine-5-acetie acid. Separation of isomers, followed by high temperature and pressure treatment with ammonia, gives the three corresponding amino-pyrimidine derivatives (see FIG. 20). The amino-pyrimidine derivatives are separated and amino-protected, then coupled to a protected PNA backbone ester. Ester hydrolysis results in PNA monomers for production of PNA oligomers containing 2-amino; 4-amino; and/or 2,4-diamino pyrimidine-5-yl bases.

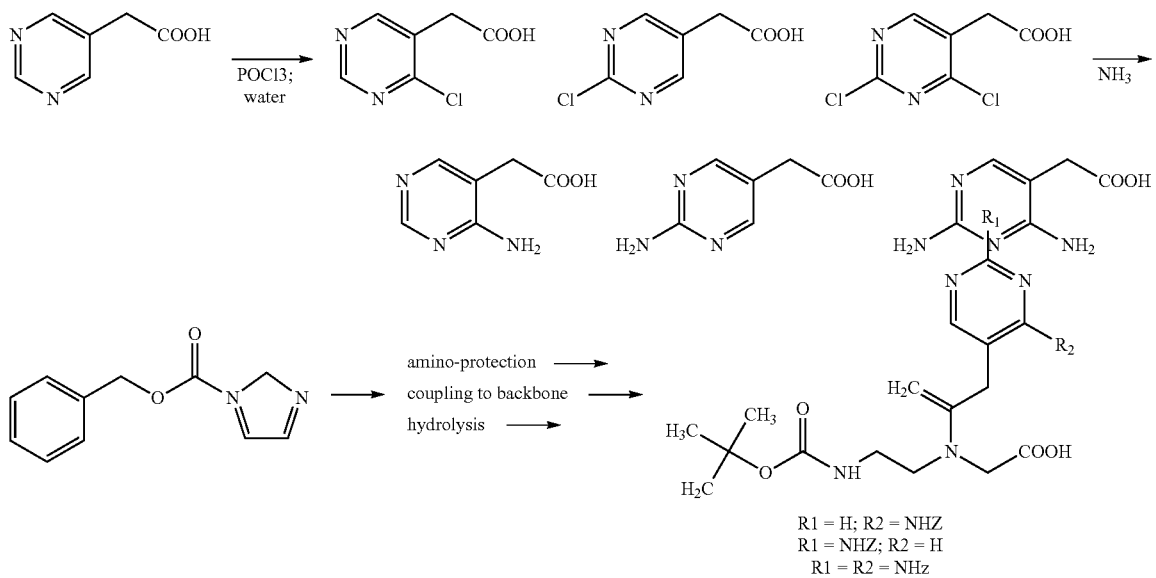

Example 50

Synthesis of Xanthine and Thio-xanthine-coupled PNA Monomers

Xanthine, 2-thio-xanthine, and 6-thio-xanthine are commercially available, for instance, from ScienceLab.com. Further, S. A. Benner et al., *Nucleic Acid Research* 24(7): 1308-1313 (1996) teaches the preparation of a xanthosine-DNA monomer, including a less acidic and preferable 7-deaza analog, and notes the preferred protection of both oxygens during solid phase synthesis.

Xanthine PNA-monomers, as well as 2-thio and 6-thio xanthine monomers, are prepared by:

1. Protecting both oxygens or both oxygen and sulphur with appropriate protection groups such as (possibly substituted) benzyl.
2. Alkylating at N-9 with ethyl bromacetate. (Separating N-7 alkylated byproduct.)
3. Hydrolyzing the ethyl ester.
4. HBTU or Carbodiimide-mediated coupling of the nucleobase-acids to 2-Boe-aminoethyl-ethylglycinate.
5. Hydrolyzing the resulting monomer ester to the monomer free acid.
6. The resulting monomers may be used in Merrifield solid phase synthesis of xanthine, 2-thio-xanthine and 6-thio-xanthine-containing PNAs

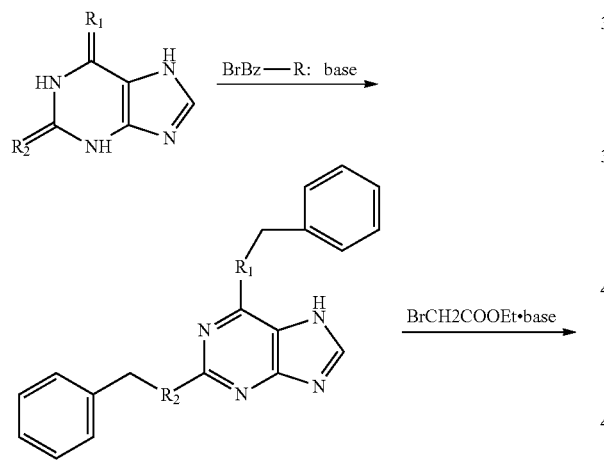

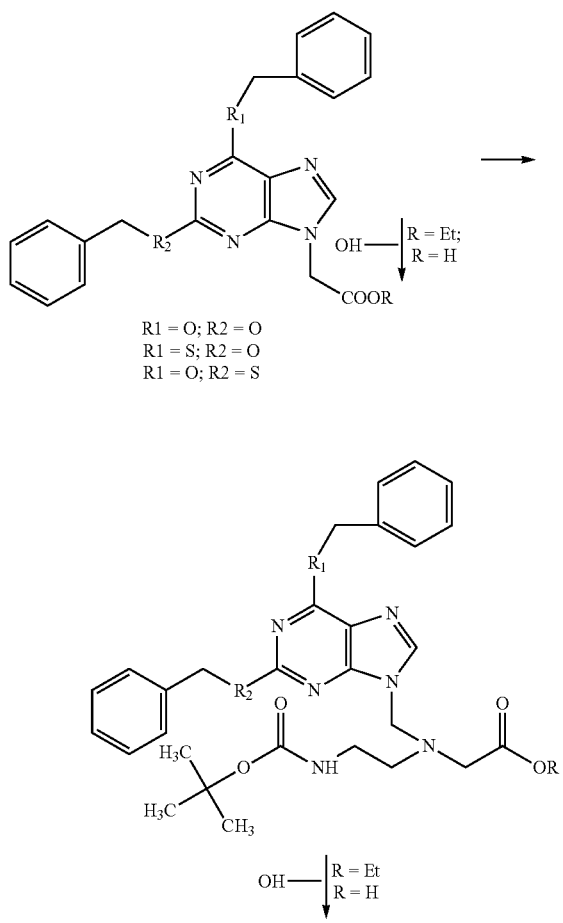

Yet other embodiments of the invention will be apparent to those skilled in the art from consideration of the specification and practice of the invention disclosed herein. It is intended that the specification and examples be considered as exemplary only.

---

What is claimed is:

1. A composition comprising at least one recognition unit and at least one detection unit wherein:
   a) each unit independently comprises at least one nucleic acid analog segment, wherein each nucleic acid analog segment comprises a peptide-nucleic acid backbone;
   b) at least one nucleic acid analog segment of the recognition unit specifically hybridizes to at least one nucleic acid analog segment of the detection unit through base-pairing that comprises one or more 6-thioguanine:2-oxopyrimidine base pairs;
   c) the recognition unit further comprises at least one probe which recognizes at least one target in a sample; and
   d) the detection unit further comprises at least one detectable label;
      wherein each of the nucleic acid analog segments on the recognition unit that specifically hybridizes to at least one of the nucleic acid analog segments on the detection unit does not specifically hybridize or bind to the probe, does not specifically hybridize or bind to the detectable label, and does not specifically hybridize or bind to the target; and
      wherein each of the detection units does not specifically hybridize or bind to the probe, does not specifically hybridize or bind to the detectable label, and does not specifically hybridize or bind to the target.

2. The composition according to claim 1 wherein the sample is an immunohistochemistry sample.

3. The composition according to claim 1, wherein the recognition unit and the detection unit each comprise at least two nucleic acid analog segments.

4. The composition according to claim 3, wherein each of the two nucleic acid analog segments present on the same unit comprise different nucleobase sequences.

5. The composition according to claim 1, wherein at least one nucleic acid analog segment on the recognition unit is capable of specifically hybridizing to at least two different nucleic acid analog segments on the detection unit and/or at least one nucleic acid analog segment of the detection unit is capable of hybridizing to at least two different nucleic acid analog segments on the recognition unit.

6. The composition according to claim 1, wherein the probe recognizes the target indirectly by binding to a primary, secondary, or tertiary binding agent.

7. The composition according to claim 6, wherein the probe is chosen from a primary antibody, a secondary antibody, or a fragment thereof.

8. The composition according to claim 1, wherein at least one unit further comprises at least one polymer.

9. The composition according to claim 8, wherein the polymer is dextran.

10. The composition according to claim 1, wherein at least one unit further comprises at least one linker.

11. The composition according to claim 10, wherein the linker is chosen from a molecule comprising polyethylene glycol and a molecule comprising at least two units according to the Formula I:

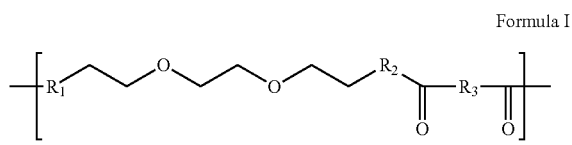

Formula I wherein $R_1$ is NH or O, $R_2$ is NH or O, and $R_3$ is selected from the group consisting of methyl, ethyl, propyl, $CH_2$—O—$CH_2$, and $(CH_2$—O—$CH_2)_2$.

12. A kit comprising the composition according to claim 1, and one or more reference samples, one or more reagents to detect the detectable label, one or more buffers, one or more reagents to reduce non-specific binding, or one or more reagents for antigen retrieval.

13. A composition comprising at least one recognition unit, at least one detection unit, and at least one adaptor unit, wherein:
   a) each unit comprises at least one nucleic acid analog segment, wherein each nucleic acid analog segment comprises a peptide-nucleic acid backbone;
   b) at least one nucleic acid analog segment of the recognition unit specifically hybridizes to at least one nucleic acid analog segment of the adaptor unit and at least one nucleic acid analog segment of the adaptor unit specifically hybridizes to at least one nucleic acid analog segment of the detection unit, wherein at least one of the specific hybridization of the recognition unit to the adaptor unit or the specific hybridization of the adaptor unit to the detection unit is through bas-pairing that comprises one or more 6-thioguanine:2-oxopyrimidine base pairs;
   c) the recognition unit further comprises at least one probe which recognizes at least one target in a sample; and
   d) the detection unit further comprises at least one detectable label;
   wherein each of the nucleic acid analog segments on a recognition unit that specifically hybridizes to at least one nucleic acid analog segment on an adaptor unit does not specifically hybridize or bind to the probe, detectable label, or target;
   wherein each detection unit does not specifically hybridize to the recognition unit, does not specifically hybridize or bind to the probe, does not specifically hybridize or bind to the detectable label, and does not specifically hybridize or bind to the target; and
   wherein each adaptor unit does not specifically hybridize or bind to the probe, does not specifically hybridize or bind to the detectable label, and does not specifically hybridize or bind to the target.

14. The composition according to claim 13 wherein the sample is an immunohistochemistry sample.

15. The composition according to claim 13, wherein each unit comprises at least two nucleic acid analog segments.

16. The composition according to claim 15, wherein each of the two nucleic acid analog segments present on the same unit comprise different nucleobase sequences.

17. The composition according to claim 13, wherein the recognition unit comprises at least two nucleic acid analog segments that specifically hybridize to at least two nucleic acid analog segments of the adaptor unit.

18. The composition according to claim 13, wherein at least one nucleic acid analog segment on the recognition unit is capable of specifically hybridizing to at least two different nucleic acid analog segments on the adapter unit, at least one nucleic acid analog segment on the adaptor unit is capable of specifically hybridizing to at least two different nucleic acid analog segments on the recognition unit and/or at least two different nucleic acid analog segments on the detection unit, and/or at least one nucleic acid analog segment on the detection unit is capable of specifically hybridizing to at least two different nucleic acid analog segments on the adaptor unit.

19. The composition according to claim 13, wherein the probe recognizes the target indirectly by binding to a primary, secondary, or tertiary binding agent.

20. The composition according to claim 19, wherein the probe is chosen from a primary antibody, a secondary antibody, or a fragment thereof.

21. The composition according to claim 13, wherein at least one unit further comprises at least one polymer.

22. The composition according to claim 21, wherein the polymer is dextran.

23. The composition according to claim 13, wherein at least one unit further comprises at least one linker.

24. The composition according to claim 23, wherein the linker is chosen from a molecule comprising polyethylene glycol and a molecule comprising at least two units according to the Formula I:

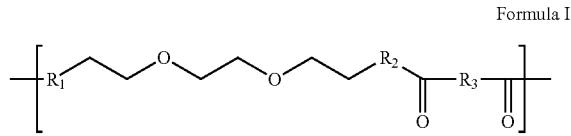

Formula I wherein $R_1$ is NH or O, $R_2$ is NH or O, and $R_3$ is selected from the group consisting of methyl, ethyl, propyl, $CH_2$—O—$CH_2$, and $(CH_2$—O—$CH_2)_2$.

25. The composition according to claim 13, comprising an adaptor unit comprising at least four nucleic acid analog segments, wherein
   a) a first nucleic acid analog segment of the adaptor unit specifically hybridizes to a nucleic acid analog segment of the recognition unit;
   b) the second, third, and fourth nucleic acid analog segments of the adaptor unit specifically hybridize to at least one nucleic acid analog segment of a detection unit or a further adaptor unit; and
   c) the nucleic acid analog segments on the recognition unit, detection unit, or adaptor unit that specifically hybridize to other nucleic acid analog segments on the recognition unit, detection unit, or adaptor unit do not specifically hybridize or bind to the probe, do not specifically hybridize or bind to the detectable label, and do not specifically hybridize or bind to the target.

26. A kit comprising the composition according to claim 13, one or more reference samples, one or more reagents to detect the detectable label, one or more buffers, one or more reagents to reduce non-specific binding, or one or more reagents for antigen retrieval.

* * * * *

SEQUENCE LISTING

```
<160> NUMBER OF SEQ ID NOS: 22

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (3)..(4)
<223> OTHER INFORMATION: Diaminopurine
<220> FEATURE:
<221> NAME/KEY: modified_base
<222> LOCATION: (5)..(6)
<223> OTHER INFORMATION: Thioguanine
```

<400> SEQUENCE: 1 tcnnnntaca                                                                                          10

<210> SEQ ID NO 2
<211> LENGTH: 10
<212> TYPE: DNA
<213> ORGANISM: Artificial Sequence
<220> FEATURE:
<223> OTHER INFORMATION: Description of Combined DNA/RNA Molecule:
      Synthetic PNA sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (1)
<223> OTHER INFORMATION: 2/4-thiouracil
<220> FEATURE:
<221> NAME/KEY: modified_base
<222> LOCATION: (3)
<223> OTHER INFORMATION: 2/4-thiouracil
<220> FEATURE:
<221> NAME/KEY: modified_base
<222> LOCATION: (4)
<223> OTHER INFORMATION: Diaminopurine
<220> FEATURE:
<221> NAME/KEY: modified_base
<222> LOCATION: (5)..(6)
<223> OTHER INFORMATION: Pyrimidone
<220> FEATURE:
<221> NAME/KEY: modified_base
<222> LOCATION: (10)
<223> OTHER INFORMATION: Diaminopurine

<400> SEQUENCE: 2 ngnnnnttgn                                                                                          10

<210> SEQ ID NO 3
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic PNA sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (2)
<223> OTHER INFORMATION: 2/4-thiouracil
<220> FEATURE:
<221> NAME/KEY: modified_base
<222> LOCATION: (3)..(4)
<223> OTHER INFORMATION: Thioguanine
<220> FEATURE:
<221> NAME/KEY: modified_base
<222> LOCATION: (5)..(6)
<223> OTHER INFORMATION: Diaminopurine
<220> FEATURE:
<221> NAME/KEY: modified_base
<222> LOCATION: (8)
<223> OTHER INFORMATION: 2/4-thiouracil
<220> FEATURE:
<221> NAME/KEY: modified_base
<222> LOCATION: (9)
<223> OTHER INFORMATION: Diaminopurine
<220> FEATURE:
<221> NAME/KEY: modified_base
<222> LOCATION: (10)
<223> OTHER INFORMATION: Thioguanine
<220> FEATURE:
<221> NAME/KEY: modified_base
<222> LOCATION: (11)
<223> OTHER INFORMATION: Diaminopurine -continued

```
<400> SEQUENCE: 3
cnnnnntnnn nc                                                           12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (3)
<223> OTHER INFORMATION: Pyrimidone
<220> FEATURE:
<221> NAME/KEY: modified_base
<222> LOCATION: (9)..(10)
<223> OTHER INFORMATION: Pyrimidone

<400> SEQUENCE: 4
gtntaattnn ag                                                           12

<210> SEQ ID NO 5
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic PNA sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (1)
<223> OTHER INFORMATION: Diaminopurine
<220> FEATURE:
<221> NAME/KEY: modified_base
<222> LOCATION: (2)
<223> OTHER INFORMATION: Thioguanine
<220> FEATURE:
<221> NAME/KEY: modified_base
<222> LOCATION: (5)
<223> OTHER INFORMATION: Thioguanine
<220> FEATURE:
<221> NAME/KEY: modified_base
<222> LOCATION: (6)..(7)
<223> OTHER INFORMATION: Diaminopurine
<220> FEATURE:
<221> NAME/KEY: modified_base
<222> LOCATION: (8)
<223> OTHER INFORMATION: Thioguanine
<220> FEATURE:
<221> NAME/KEY: modified_base
<222> LOCATION: (10)
<223> OTHER INFORMATION: 2/4-thiouracil
<220> FEATURE:
<221> NAME/KEY: modified_base
<222> LOCATION: (12)
<223> OTHER INFORMATION: 2/4-thiouracil

<400> SEQUENCE: 5
nntcnnnngn cn                                                           12

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
```

```
<221> NAME/KEY: modified_base
<222> LOCATION: (5)
<223> OTHER INFORMATION: Pyrimidone
<220> FEATURE:
<221> NAME/KEY: modified_base
<222> LOCATION: (8)
<223> OTHER INFORMATION: Pyrimidone
<220> FEATURE:
<221> NAME/KEY: modified_base
<222> LOCATION: (11)
<223> OTHER INFORMATION: Pyrimidone

<400> SEQUENCE: 6
agacnttnga nt                                                         12

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (3)..(4)
<223> OTHER INFORMATION: Diaminopurine
<220> FEATURE:
<221> NAME/KEY: modified_base
<222> LOCATION: (5)..(6)
<223> OTHER INFORMATION: Inosine

<400> SEQUENCE: 7 tcnnntaca                                                             10

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (1)
<223> OTHER INFORMATION: Diaminopurine
<220> FEATURE:
<221> NAME/KEY: modified_base
<222> LOCATION: (4)
<223> OTHER INFORMATION: Diaminopurine
<220> FEATURE:
<221> NAME/KEY: modified_base
<222> LOCATION: (9)
<223> OTHER INFORMATION: Diaminopurine

<400> SEQUENCE: 8
ngtntcgtnc cg                                                         12

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      PNA sequence

<400> SEQUENCE: 9
aacgggataa ctgcacct                                                   18

<210> SEQ ID NO 10
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      PNA sequence

<400> SEQUENCE: 10
tcaaggtaca                                                              10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA sequence

<400> SEQUENCE: 11
tgtaccttga                                                              10

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (5)
<223> OTHER INFORMATION: Pyrimidone
<220> FEATURE:
<221> NAME/KEY: modified_base
<222> LOCATION: (8)
<223> OTHER INFORMATION: Pyrimidone
<220> FEATURE:
<221> NAME/KEY: modified_base
<222> LOCATION: (10)
<223> OTHER INFORMATION: Diamionpurine
<220> FEATURE:
<221> NAME/KEY: modified_base
<222> LOCATION: (11)
<223> OTHER INFORMATION: Pyrimidone

<400> SEQUENCE: 12
agacnttngn nt                                                           12

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (3)
<223> OTHER INFORMATION: Pyrimidone
<220> FEATURE:
<221> NAME/KEY: modified_base
<222> LOCATION: (6)
<223> OTHER INFORMATION: Diaminopurine
<220> FEATURE:
<221> NAME/KEY: modified_base
<222> LOCATION: (9)..(10)
<223> OTHER INFORMATION: Pyrimidone

<400> SEQUENCE: 13
gtntanttnn ag                                                           12

<210> SEQ ID NO 14
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (5)..(6)
<223> OTHER INFORMATION: Pyrimidone

<400> SEQUENCE: 14 ttgannttag                                                          10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (5)..(6)
<223> OTHER INFORMATION: Pyrimidone

<400> SEQUENCE: 15 tgtannttga                                                          10

<210> SEQ ID NO 16
<211> LENGTH: 10
<212> TYPE: DNA
<213> ORGANISM: Artificial Sequence
<220> FEATURE:
<223> OTHER INFORMATION: Description of Combined DNA/RNA Molecule:
      Synthetic PNA sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (1)
<223> OTHER INFORMATION: 2/4-thiouracil
<220> FEATURE:
<221> NAME/KEY: modified_base
<222> LOCATION: (3)
<223> OTHER INFORMATION: 2/4-thiouracil
<220> FEATURE:
<221> NAME/KEY: modified_base
<222> LOCATION: (4)
<223> OTHER INFORMATION: Diaminopurine
<220> FEATURE:
<221> NAME/KEY: modified_base
<222> LOCATION: (5)..(6)
<223> OTHER INFORMATION: Pyrimidone
<220> FEATURE:
<221> NAME/KEY: modified_base
<222> LOCATION: (10)
<223> OTHER INFORMATION: Diaminopurine

<400> SEQUENCE: 16 ngnnnnttgn                                                          10

<210> SEQ ID NO 17
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic PNA sequence
<220> FEATURE:
<223> OTHER INFORMATION: Description of Artificial Sequence: Synthetic
      PNA sequence
<220> FEATURE:
```

<221> NAME/KEY: modified_base
<222> LOCATION: (1)
<223> OTHER INFORMATION: Diaminopurine
<220> FEATURE:
<221> NAME/KEY: modified_base
<222> LOCATION: (5)
<223> OTHER INFORMATION: Thioguanine
<220> FEATURE:
<221> NAME/KEY: modified_base
<222> LOCATION: (6)..(7)
<223> OTHER INFORMATION: Diaminopurine
<220> FEATURE:
<221> NAME/KEY: modified_base
<222> LOCATION: (8)
<223> OTHER INFORMATION: Thioguanine
<220> FEATURE:
<221> NAME/KEY: modified_base
<222> LOCATION: (10)
<223> OTHER INFORMATION: 2/4-thiouracil
<220> FEATURE:
<221> NAME/KEY: modified_base
<222> LOCATION: (12)
<223> OTHER INFORMATION: 2/4-thiouracil

<400> SEQUENCE: 17
ngtcnnnngn cn                                                          12

<210> SEQ ID NO 18
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic PNA sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (1)
<223> OTHER INFORMATION: 2/4-thiouracil
<220> FEATURE:
<221> NAME/KEY: modified_base
<222> LOCATION: (3)..(4)
<223> OTHER INFORMATION: Thioguanine
<220> FEATURE:
<221> NAME/KEY: modified_base
<222> LOCATION: (5)..(6)
<223> OTHER INFORMATION: Diaminopurine
<220> FEATURE:
<221> NAME/KEY: modified_base
<222> LOCATION: (8)
<223> OTHER INFORMATION: 2/4-thiouracil
<220> FEATURE:
<221> NAME/KEY: modified_base
<222> LOCATION: (9)
<223> OTHER INFORMATION: Diaminopurine
<220> FEATURE:
<221> NAME/KEY: modified_base
<222> LOCATION: (11)
<223> OTHER INFORMATION: Diamionpurine

<400> SEQUENCE: 18
ncnnnntnng nc                                                          12

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (5)..(6)

-continued

```
<223> OTHER INFORMATION: Thioguanine

<400> SEQUENCE: 19 ctaanntcaa                                                              10

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (5)..(6)
<223> OTHER INFORMATION: Thioguanine

<400> SEQUENCE: 20 tcaanntaca                                                              10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA sequence

<400> SEQUENCE: 21
ctaaggtcaa                                                              10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (3)..(4)
<223> OTHER INFORMATION: Diaminopurine

<400> SEQUENCE: 22 tcnnggtaca                                                              10
```